US009587024B2

(12) United States Patent
Clemmons et al.

(10) Patent No.: US 9,587,024 B2
(45) Date of Patent: Mar. 7, 2017

(54) MONOCLONAL ANTIBODIES FOR ENHANCING OR INHIBITING INSULIN-LIKE GROWTH FACTOR 1 (IGF-1)

(71) Applicant: The University of North Carolina at Chapel Hill, Chapel Hill, NC (US)

(72) Inventors: David Clemmons, Chapel Hill, NC (US); Laura Maile, Chapel Hill, NC (US); Michael Naso, Radnor, PA (US); Francis J. Carr, Balmedie (GB); Timothy D. Jones, Babraham (GB); Simon William Keen, West Wickham (GB)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/728,379

(22) Filed: Jun. 2, 2015

(65) Prior Publication Data
US 2015/0259422 A1    Sep. 17, 2015

Related U.S. Application Data

(62) Division of application No. 14/015,457, filed on Aug. 30, 2013.

(60) Provisional application No. 61/695,409, filed on Aug. 31, 2012.

(51) Int. Cl.
C12N 5/00     (2006.01)
C12N 15/00    (2006.01)
C07H 21/04    (2006.01)
C07K 16/28    (2006.01)

(52) U.S. Cl.
CPC ...... *C07K 16/2848* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,336,618 A | 8/1994 | Coller | |
| 5,578,704 A | 11/1996 | Kim et al. | |
| 5,753,230 A | 5/1998 | Brooks et al. | |
| 5,965,710 A | 10/1999 | Bodmer et al. | |
| 6,369,204 B1 | 4/2002 | Kim et al. | |
| 6,531,580 B1 | 3/2003 | Huse et al. | |
| 6,590,079 B2 | 7/2003 | Huse et al. | |
| 6,596,850 B1 | 7/2003 | Huse | |
| 6,887,473 B1 | 5/2005 | Brooks et al. | |
| 7,163,681 B2 | 1/2007 | Giles-Komar et al. | |
| 7,354,586 B2 | 4/2008 | Brooks et al. | |
| 7,371,382 B2 | 5/2008 | Huse et al. | |
| 7,422,744 B2 | 9/2008 | Huse et al. | |
| 7,550,142 B2 | 6/2009 | Giles-Komar et al. | |
| 7,723,483 B2 | 5/2010 | Clemmons et al. | |
| 8,062,635 B2 | 11/2011 | Hattori et al. | |
| 8,093,360 B2 | 1/2012 | Casey | |
| 8,187,595 B2 | 5/2012 | Clemmons et al. | |
| 8,206,706 B2 | 6/2012 | Clemmons et al. | |
| 9,068,000 B2 | 6/2015 | Clemmons et al. | |
| 9,073,996 B2 | 7/2015 | Clemmons et al. | |
| 2003/0195147 A1 | 10/2003 | Pillutla et al. | |
| 2010/0297139 A1 | 11/2010 | Reiser | |
| 2012/0269816 A1 | 10/2012 | Clemmons et al. | |
| 2015/0259421 A1 | 9/2015 | Clemmons et al. | |

FOREIGN PATENT DOCUMENTS

| | | |
|---|---|---|
| EP | 2 025 685 A1 | 2/2009 |
| WO | WO 92/07871 A1 | 5/1992 |
| WO | WO 00/55181 A1 | 9/2000 |
| WO | WO 2005/117936 A2 | 12/2005 |
| WO | WO 2009/061448 A2 | 5/2009 |
| WO | WO 2010/054189 A1 | 5/2010 |

OTHER PUBLICATIONS

Artoni et al. "Integrin β3 regions controlling binding of murine mAb 7E3: Implications for the mechanism of integrin αIIbβ3 activation" *Proceedings of the National Academy of Sciences* 101(36):13114-13120 (2004).
Bantis et al. "Influence of $β_3$ Integrin Gene $Leu^{33}/Pro^{33}$ Polymorphism on Primary Glomerulonephritis" *Nephron Experimental Nephrology* 99:e33-e37 (2005).
Beer et al. "Immobilized Arg-Gly-Asp (RGD) Peptides of Varying Lengths as Structural Probes of the Platelet Glycoprotein IIb/IIIa Receptor" *Blood* 79:117-128 (1992).
Brosius, Frank C., III "Trophic Factors and Cytokines in Early Diabetic Glomerulopathy" *Experimental Diabetes Research* 4:225-233 (2003).
Catherwood et al. "Glucose-induced oxidative stress in mesangial cells" *Kidney International* 61:599-608 (2002).
Chertin et al. "Insulin-like growth factor-1 expression in reflux nephropathy" *Pediatric Surgery International* 20:283-289 (2004).
Clemmons et al. "Synthetic αVβ3 Antagonists Inhibit Insulin-Like Growth Factor-I-Stimulated Smooth Muscle Cell Migration and Replication" *Endocrinology* 140(10):4616-4621 (1999).
Clemmons et al. "Interaction between Insulin-Like Growth Factor-I Receptor and αVβ3 Integrin Linked Signaling Pathways: Cellular Responses to Changes in Multiple Signaling Inputs" *Molecular Endocrinology* 19(1):1-11 (2005).
Cochrane et al. "In vitro glycation of glomerular basement membrane alters its permeability: a possible mechanism in diabetic complications" *FEBS Letters* 375:41-44 (1995).
Coller, Barry S. "Binding of Abciximab to αVβ3 and Activated αMβ2 Receptors: With a Review of Platelet-Leukocyte Interactions" *Thrombosis and Haemostasis* 82:326-336 (1999).

(Continued)

Primary Examiner — Marianne P Allen
(74) Attorney, Agent, or Firm — Sterne, Kessler, Goldstein & Fox P.L.L.C.

(57) ABSTRACT

The present invention provides an antibody or antigen-binding fragment thereof that binds $α_vβ_3$ integrin, as well as methods of use in the treatment of diseases and disorders.

35 Claims, 18 Drawing Sheets

(56) References Cited

OTHER PUBLICATIONS

Coller, Barry S. "Anti-GPIIb/IIIa Drugs: Current Strategies and Future Directions" *Thrombosis and Haemostasis* 86:427-443 (2001).

Coppey et al. "ACE Inhibitor or Angiotensin II Receptor Antagonist Attenuates Diabetic Neuropathy in Streptozotocin-Induced Diabetic Rats" *Diabetes* 55:341-348 (2006).

Feldmann et al. "Diabetic retinopathy is associated with decreased serum levels of free IDF-I and changes of IGF-binding proteins" *Growth Hormone & IGF Research* 10:53-59 (2000).

Filizola et al. "Mechanistic Insights from a Refined Three-dimensional Model of Integrin $\alpha_{IIb}\beta_3$" *The Journal of Biological Chemistry* 279(23):24624-24630 (2004).

Frystyk et al. "The relationship between the circulating IGF system and the presence of retinopathy in Type 1 diabetic patients" *Diabetic Medicine* 20:269-276 (2003).

Gerrity et al. "Diabetes-Induced Accelerated Atherosclerosis in Swine" *Diabetes* 50:1654-1665 (2001).

Gomez et al. "Acute Pancreatitis Signals Activation of Apoptosis-Associated and Survival Genes in Mice" *Experimental Biology and Medicine* 226(7):692-700 (2001).

Grulich-Henn et al. "Transport of insulin-like growth factor-I across endothelial cell monolayers and its binding to the subendothelial matrix" *Experimental and Clinical Endocrinology and Diabetes* 110:67-73 (2002).

Gura, Trisha "Systems for Identifying New Drugs Are Often Faulty" *Science* 278:1041-1042 (1997).

Gutheil et al. "Targeted Antiangiogenic Therapy for Cancer Using Vitaxin: A Humanized Monoclonal Antibody to the Integrin $\alpha_v\beta_3$" *Clinical Cancer Research* 6:3056-3061 (2000).

Grant et al. "The role of growth factors in the pathogenesis of diabetic retinopathy" *Expert Opinion on Investigational Drugs* 13:1275-1293 (2004).

Hellstrom et al. "Postnatal Serum Insulin-Like Growth Factor I Deficiency Is Associated With Retinopathy of Prematurity and Other Complications of Premature Birth" *Pediatrics* 112:1016-1020 (2003).

Higashi et al. "IGF-1, oxidative stress, and atheroprotection" *Trends in Endocrinology & Metabolism* 21(4):245-254 (2010).

Hoyne et al. "Properties of an insulin receptor with an IGF-1 receptor loop exchange in the cysteine-rich region" *FEBS Letters* 469:57-60 (2000).

Chemicon International "Rabbit Anti-Integrin beta3 Polyclonal Antibody" http://www.chemicon.com/webfiles/PDF/AB1932.pdf (2006) 3 pages.

Imai et al. "Roles of Phosphatidylinositol 3-Kinase and Mitogen-Activated Protein Kinase Pathways in Stimulation of Vascular Smooth Muscle Cell Migration and Deoxyriboncleic Acid Synthesis by Insulin-Like Growth Factor-I" *Endocrinology* 140(9):4228-4235 (1999).

International Search Report and the Written Opinion of the International Searching Authority corresponding to International Patent Application No. PCT/US05/15957; mailed Jun. 19, 2006.

Johnstone et al. *Immunochemistry in Practice* 2nd Ed. Blackwell Scientific Publications: pp. 30 and 49-50 (1987).

Kricker et al. "Structural and Functional Evidence for the Interaction of Insulin-Like Growth Factors (IGFs) and IGF Binding Proteins with Vitronectin" *Endocrinology* 144(7):2807-2815 (2003).

Larsen et al. "Use of the Göttingen Minipig as a Model of Diabetes, with Special Focus on Type 1 Diabetes Research" *ILAR Journal* 45(3):303-313 (2004).

Ling et al. "Tyrosine Phosphorylation of the β3-Subunit of the αVβ3 Integrin Is Required for Membrane Association of the Tyrosine Phosphatase SHP-2 and Its Further Recruitment to the Insulin-Like Growth Factor I Receptor" *Molecular Endocrinology* 17(9):1824-1833 (2003).

Maile et al. "Structural analysis of the role of the β3 subunit of the αβ3 integrin in IGF-I signaling" *Journal of Cell Science* 114(7):1417-1425 (2001).

Maile et al. "Insulin-like Growth Factor I Increases $\alpha_v\beta_3$ Affinity by Increasing the Amount of Integrin-associated Protein That Is Associated with Non-raft Domains of the Cellular Membrane" *The Journal of Biological Chemistry* 277(3):1800-1805 (2002).

Maile et al. "Regulation of Insulin-like Growth Factor I Receptor Dephosphorylation by SHPS-1 and the Tyrosine Phosphatase SHP-2" *The Journal of Biological Chemistry* 277(11):8955-8960 (2002).

Maile et al. "The αVβ3 Integrin Regulates Insulin-Like Growth Factor I (IGF-I) Receptor Phosphorylation by Altering the Rate of Recruitment of the Src-Homology 2-Containing Phosphotyrosine Phosphatase-2 to the Activated IGF-I Receptor" *Endocrinology* 143(11):4259-4264 (2002).

Maile et al. "Integrin-Associated Protein Binding Domain of Thrombospondin-1 Enhances Insulin-Like Growth Factor-I Receptor Signaling in Vascular Smooth Muscle Cells" *Circulation Research* 93:925-931 (2003).

Maile et al. "The Association between Integrin-associated Protein and SHPS-1 Regulates Insulin-like Growth Factor-I Receptor Signaling in Vascular Smooth Muscle Cells" *Molecular Biology of the Cell* 14:3519-3528 (2003).

Maile et al. "Insulin-like Growth Factor-I Signaling in Smooth Muscle Cells Is Regulated by Ligand Binding to the [177]CYDMKTTC[184] Sequence of the β3-Subunit of αVβ3" *Molecular Endocrinology* 20(2):405-413 (2006).

Maile et al. "The Heparin Binding Domain of Vitronectin Is the Region that Is Required to Enhance Insulin-Like Growth Factor-I Signaling" *Molecular Endocrinology* 20(4):881-892 (2006).

Maile et al. "Hyperglycemia Alters the Responsiveness of Smooth Muscle Cells to Insulin-Like Growth Factor-I" *Endocrinology* 148(5):2435-2443 (2007).

Maile et al. "Modulation of Integrin Antagonist Signaling by Ligand Binding of the Heparin-Binding Domain of Vitronectin to the αVβ3 Integrin" *Journal of Cellular Biochemistry* 105:437-446 (2008).

Marions et al. "The effect of antiprogestin on integrin expression in human endometrium: an immunohistochemical study" *Molecular Human Reproduction* 4(5):491-495 (1998).

Marshall et al. "Early Micro- and Macro-Angiopathy in the Streptozotocin Diabetic Minipig" *Research in Experimental Medicine* 177:145-158 (1980).

Moralez et al. "Insulin-Like Growth Factor Binding Protein-5 (IGFBP-5) Interacts With Thrombospondin-1 to Induce Negative Regulatory Effects on IGF-I Actions" *Journal of Cellular Physiology* 203:328-334 (2005).

Qaum et al. "VEGF-Initiated Blood-Retinal Barrier Breakdown in Early Diabetes" *Investigative Ophthalmology & Visual Science* 42(10):2408-2413 (2001).

Riisbro et al. "Prognostic Significance of Soluble Urokinase Plasminogen Activator Receptor in Serum and Cytosol of Tumor Tissue from Patients with Primary Breast Cancer" *Clinical Cancer Research* 8:1132-1141 (2002).

Saegusa et al. "The Direct Binding of Insulin-like Growth Factor-1 (IGF-1) to Integrin αvβ3 Is Involved in IGF-1 Signaling" *The Journal of Biological Chemistry* 284(36):24106-24114 (2009).

Speicher et al. "Pharmacologic therapy for diabetic retinopathy" *Expert Opinion on Emerging Drugs* 8:239-250 (2003).

Supplementary Partial European Search Report corresponding to European Patent Application No. 05804812.5: mailed Jun. 14, 2007.

Takagi et al. "Changing Ligand Specificities of αvβ1 and αvβ3 Integrins by Swapping a Short Diverse Sequence of the β Subunit" *The Journal of Biological Chemistry* 272(32):19794-19800 (1997).

Tesch et al. "Rodent models of streptozotocin-induced diabetic nephropathy" *Nephrology* 12:261-266 (2007).

Tuttle et al. "A Novel Potential Therapy for Diabetic Nephropathy and Vascular Complications: Protein Kinase C β Inhibition" *American Journal of Kidney Diseases* 42(3):456-465 (2003).

Vogel et al. "A Novel Integrin Specificity Exemplified by Binding of the $\alpha_v\beta_6$ Integrin to the Basic Domain of the HIV Tat Protein and Vitronectin" *The Journal of Cell Biology* 121(2):461-468 (1993).

(56) References Cited

OTHER PUBLICATIONS

Wang et al. "Does Insulin-Like Growth Factor I Predict Incidence and Progression of Diabetic Retinopathy?" *Diabetes* 44:161-164 (1995).
Xiong et al. "Crystal Structure of the Extracellular Segment of Integrin αVβ3" *Science* 294:339-345 (2001).
Xiong et al. "Crystal Structure of the Extracellular Segment of Integrin αVβ3 in Complex with an Arg-Gly-Asp Ligand" *Science* 296(5565):151-155 (2002).
Xu et al. "Sensitive Blood-Retinal Barrier Breakdown Quantitation Using Evans Blue" *Investigative Ophthamology & Visual Science* 42(3):789-794 (2001).
GenBank Database Accesion No. AAA38725.1, "Ig kappa-chain Vk8-Jk1 region, partial [Mus musculus]" Oct. 4, 1994 (2 pages).
GenBank Database Accesion No. ABP01832.1, "Immunoglobulin alpha heavy chain variable region [Mus musculus]" Mar. 22, 2007 (2 pages).
Maile et al. "A Monoclonal Antibody Against $\alpha_I\beta_3$ Intergrin Inhibits Development of Atherosclerotic Lesions in Diabetic Pigs" *Science Translational Medicine* 2(18) ra11:1-8 (2010).

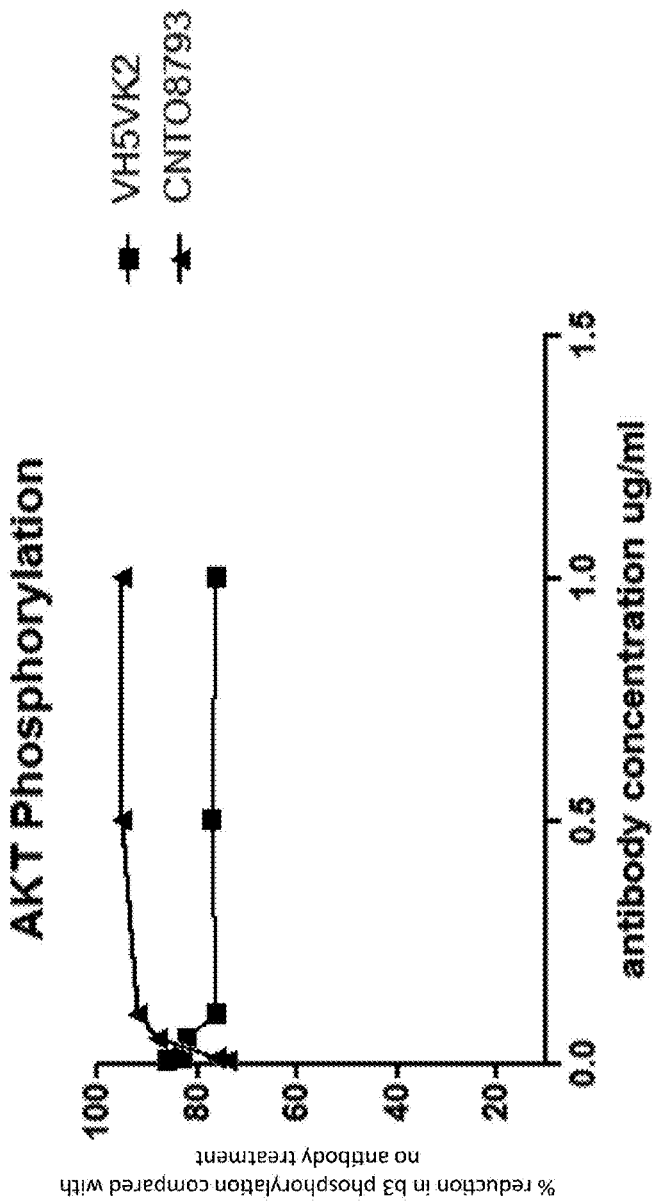

Summary of serum levels at each time point

| Time | 0.3 | Δ | 1 | Δ | 5 | |
|---|---|---|---|---|---|---|
| 1hr | 2.4 | 2 | 5 | 5.2 | 26.7 | (dose in mg/kg) |
| 4hrs | 2.1 | 2.5 | 5.4 | 2.5 | 14.5 | (serum levels in ug/ml) |
| 8hrs | | | 4.1 | 2.5 | 10 | |
| 24hrs | 0.85 | 3.9 | 3.35 | 2.5 | 8.7 | difference between (0.3 and 1) or (1 and 5) mg/kg dose  Δ |
| 48 | | | | | | |
| 96 | 0.96 | 3 | 2.9 | 2.7 | 7.85 | *a lot of values taken from set 2 pigs these seem lower values |
| 144 | 0.9 | 3 | 2.7 | 3.5 | 9.4 | |
| d7 | 1 | 5 | 5 | 1.7 | 8.4 | |
| d8 | 0.6 | 1.8 | 1.1 | 3.3 | 3.6 | |
| d10 | 0.9 | 3.5 | 3.2 | 2.8 | 8.95 | |
| d11-d14* | 0.14 | 4.2 | 0.6 | 4.6 | 2.94 | |
| d15-16 | 0.5 | 3.4 | 1.7 | 2.8 | 4.7 | |
| d17 | 0.42 | 4.7 | 1.97 | 1.5 | 2.95 | |

MONOCLONAL ANTIBODIES FOR ENHANCING OR INHIBITING INSULIN-LIKE GROWTH FACTOR 1 (IGF-1)

CROSS-REFERENCE TO RELATED APPLICATIONS

This application is a divisional of U.S. application Ser. No. 14/015,457, filed Aug. 30, 2013, now allowed, which claims the benefit of the filing date of U.S. Application No. 61/695,409, filed Aug. 31, 2012. The disclosures of these applications are hereby incorporated by reference herein in their entireties.

STATEMENT OF GOVERNMENT SUPPORT

This invention was made with government support under Grant No. HL084857-02 awarded by the National Institutes of Health. The government has certain rights in the invention.

STATEMENT REGARDING ELECTRONIC FILING OF A SEQUENCE LISTING

The content of the electronically submitted sequence listing, entitled 5470-628TS SUBSTITUTE_ST25.txt, 80,685 bytes in size, created on Dec. 10, 2014, filed herewith, is incorporated herein by reference in its entirety.

FIELD OF THE INVENTION

This invention describes compositions and methods for inhibiting the actions of insulin-like growth factor 1 (IGF-1).

BACKGROUND OF THE INVENTION

IGF-1 is a small polypeptide hormone that stimulates the growth of all types of cells. Because IGF-1 has a broad spectrum of action and stimulates balanced tissue growth it has been implicated in the development of several important human cancers and also in atherosclerosis. IGF-1 acts primarily on anchorage dependent cells that are contained in these tissues. These cells also possess a class of receptors termed integrin receptors which are responsible for their attachment to extracellular matrix molecules. In order for cells to divide normally, in response to extracellular stimuli the cell has to sense that its integrin receptors are bound to extracellular matrix molecules. Therefore manipulation of ligand occupancy of integrin receptors can alter processes that are important in disease development such as cell division and migration.

IGF-1 stimulates endothelial and smooth muscle cell division. These cells utilize the αVβ3 integrin receptor to communicate to the cell nucleus that they are adhered adequately to extracellular matrix in order to divide. The abundance of one specific integrin (the αVβ3 integrin) is relatively restricted in human tissues and it is expressed primarily in growing cells and particularly in cells involved in the maintenance of the vasculature such as smooth muscle and endothelial cells. Occupancy of this integrin receptor with its naturally occurring ligands such as osteopontin, vitronectin and thrombospondin is required for these cells to respond to IGF-1 with increased DNA synthesis and cell migration. Blocking ligand occupancy of this integrin with disintegrin antagonists results in inhibition of cell growth and migration. This cooperative interaction between αVβ3 and the IGF-1 receptor is mediated by regulating the translocation of two specific signaling molecules. These molecules are 1) a protein tyrosine phosphatase termed SHP-2 and 2) a signaling protein termed Shc. Under normal circumstances SHP-2 is localized in the cytoskeleton and cytosolic compartments of the cell. Following ligand occupancy of αVβ3, the cytoplasmic domain of the β3 integrin undergoes tyrosine phosphorylation. SHP-2 is transferred to the cell membrane by binding to proteins that bind to the phosphorylated tyrosine residues in β3. This transfer is necessary in order to localize SHP-2 to the membrane where it recruits other important signaling molecules such as Shc. SHP-2 colocalization with Shc and/or dephosphorylation of signaling molecules within the IGF-1 signaling pathway is required for their activation and for subsequent transmission of signals from the IGF-1 receptor to nucleus. Activation of the two major intracellular signaling pathways that are required for IGF-1 activation (e.g., the PI-3 kinase and MAP kinase pathways) can be inhibited by inhibiting either SHP-2 or Shc transfer to the membrane. The site of localization of SHP-2 and Shc is a membrane protein termed SHPS-1. SHPS-1 is phosphorylated in response to IGF-1. This phosphorylation is required for SHP-2 and for Shc transfer. Shc is phosphorylated after transfer to SHPS-1. Blocking αVβ3 ligand occupancy blocks both SHP-2 and Shc transfer thus inhibiting IGF-1 stimulated cell growth.

Although methods have been described previously for inhibiting ligand occupancy of the αVβ3 integrin, they all utilize a technology that inhibits binding to a specific binding site on the αVβ3 heterodimer that binds to the arginine, glycine, and asparagine (RGD) sequence within the ECM ligands. Binding αVβ3 antagonists to this site is associated with drug toxicity and side effects. Accordingly there is a need for new ways to inhibit IGF-1 actions, which do not utilize the αVβ3 binding site that binds to the RGD sequence.

The present invention overcomes previous shortcomings in the art by providing a humanized monoclonal antibody that is effective in inhibiting IGF-1 activity and treating disorders associated therewith.

SUMMARY OF THE INVENTION

In one aspect, the present invention provides an isolated antibody (e.g., a humanized antibody) or antigen-binding fragment thereof that binds $\alpha_v\beta_3$ integrin, wherein the antibody or antigen-binding fragment thereof comprises the light chain complementarity determining region (CDR) sequences LCDR1 of SEQ ID NO:1 (KSSQSLLYSSNQK-NYLA); LCDR2 of SEQ ID NO:2 (WASTRES); and LCDR3 of SEQ ID NO:3 (KQYYTYPLT).

In a further aspect the present invention provides an isolated antibody (e.g., a humanized antibody) or antigen-binding fragment thereof that binds $\alpha_v\beta_3$ integrin, wherein the antibody or antigen-binding fragment thereof comprises the heavy chain complementarity determining region (CDR) sequences HCDR1 of SEQ ID NO:4 (NSWMN); HCDR2 of SEQ ID NO:5 (IFPGDGDTNYNGKFKG) and HCDR3 of SEQ ID NO:6 (WGLTRDRRLYLDY).

In a further aspect, the present invention provides an isolated antibody (e.g., a humanized antibody) or antigen-binding fragment thereof that binds $\alpha_v\beta_3$ integrin, wherein the antibody or antigen-binding fragment thereof comprises the light chain complementarity determining region (CDR) sequences LCDR1 of SEQ ID NO:1 (KSSQSLLYSSNQK-NYLA); LCDR2 of SEQ ID NO:2 (WASTRES); and LCDR3 of SEQ ID NO:3 (KQYYTYPLT) and the heavy chain complementarity determining region (CDR)

sequences HCDR1 of SEQ ID NO:4 (NSWMN); HCDR2 of SEQ ID NO:5 (IFPGDGDTNYNGKFKG) and HCDR3 of SEQ ID NO:6 (WGLTRDRRLYLDY).

In a further aspect, the present invention provides an isolated antibody or antigen-binding fragment thereof that binds $\alpha_v\beta_3$ integrin, wherein the antibody or antigen-binding fragment thereof comprises a heavy chain variable region (HCVR) selected from the group consisting of: a) a HCVR comprising the amino acid sequence of SEQ ID NO:7 (VH1; Q A Q L V Q S G P E L K K P G A S V K V S C K A S G Y L F S N S W M N W V K Q R P G A G L E W I G R I F P G D G D T N Y N G K F K G R A T I T A D K S T S T A Y M E L S S L R S E D S A V Y F C A R W G L T R D R R L Y L D Y W G Q G T T V T V S S); b) a HCVR comprising the amino acid sequence of SEQ ID NO:8 (VH2; Q A Q L V Q S G P E V K K P G A S V K V S C K A S G Y L F S N S W M N W V K Q R P G A G L E W I G R I F P G D G D T N Y N G K F K G R A T I T A D K S T S T A Y M E L S S L R S E D T A V Y F C A R W G L T R D R R L Y L D Y W G Q G T T V T V S S); c) a HCVR comprising the amino acid sequence of SEQ ID NO:9 (VH3; Q A Q L V Q S G A E V K K P G A S V K V S C K A S G Y L F S N S W M N W V K Q R R G A G L E W I G R I F P G D G D T N Y N G K F K G R A T I T A D K S T S T A Y M E L S S L R S E D T A V Y F C A R W G L T R D R R L Y L D Y W G Q G T T V T V S S); d) a HCVR comprising the amino acid sequence of SEQ ID NO:10 (VH4; Q A Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y F C A R W G L T R D R R L Y L D Y W G Q G T T V T V S S); e) a HCVR comprising the amino acid sequence of SEQ ID NO:11 (VH5; Q A Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y C A R W G L T R D R R L Y L D Y W G Q G T T V T V S S); and f) a HCVR comprising the amino acid sequence of SEQ ID NO:12 (VH6; Q V Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y Y C A R W G L T R D R R L Y L D Y W G Q G T T V T V S S).

Also provided herein is an isolated antibody or antigen-binding fragment thereof that binds $\alpha_v\beta_3$ integrin, wherein the antibody or antigen-binding fragment thereof comprises a light chain variable region (LCVR) selected from the group consisting of: a) a LCVR comprising the amino acid sequence of SEQ ID NO:13 (Vκ1; D I V M T Q S P D S L V V S L G E R A T I N C K S S Q S L L Y S S N Q K N Y L A W Y Q Q K S G Q A P R L L I Y W A S T R E S G V P D R F T G S G S G T D F T L T I S S L Q A E D V A V Y Y C K Q Y Y T Y P L T F G Q G T K L E I K); b) a LCVR comprising the amino acid sequence of SEQ ID NO:14 (Vκ2; D I V M T Q S P D S L A V S L G E R A T I N C K S S Q S L L Y S S N Q K N Y L A W Y Q Q K P G Q A P R L L I Y W A S T R E S G V P D R F T G S G S G T D F T L T I S S L Q A E D V A V Y Y C K Q Y Y T Y P L T F G Q G T K L E I K); and c) a LCVR comprising the amino acid sequence of SEQ ID NO:15 (Vκ3; D I V M T Q S P D S L A V S L G E R A T I N C K S S Q S L L Y S S N Q K N Y L A W Y Q Q K P G Q A P R L L I Y W A S T R E S G V P D R F S G S G S G T D F T L T I S S L Q A E D V A V Y Y C K Q Y Y T Y P L T F G Q G T K L E I K).

A further aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:7 (HV1), SEQ ID NO:8 (VH2), SEQ ID NO:9 (VH3), SEQ ID NO:10 (VH4) SEQ ID NO:11 (VH5) or SEQ ID NO:12 (VH6) and a light chain variable region (LCVR) comprising the amino acid sequence of SEQ ID NO:13 (Vκ1), SEQ ID NO:14 (Vκ2) or SEQ ID NO:15 (Vκ3), wherein the HCVR and the LCVR are present in any combination.

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:16 (Vκ2) (D I V M T Q S P D S L A V S L G E R A T I N C K S S Q S L L Y S S N Q K N Y L A W Y Q Q K P G Q A P R L L I Y W A S T R E S G V P D R F T G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C).

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:22 (Vκ1) (D I V M T Q S P D S L V V S L G E R A T I N C K S S Q S L L Y S S N Q K N Y L A W Y Q Q K S G Q A P R L L I Y W A S T R E S G V P D R F T G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C).

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:23 (Vκ3) (D I V M T Q S P D S L A V S L G E R A T I N C K S S Q S L L Y S S N Q K N Y L A W Y Q Q K P G Q A P R L L I Y W A S T R E S G V P D R F S G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:17 (VH6) (Q V Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y Y C A R W G L T R D R R L Y L D Y W G Q G T T V T V S S A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K K V E P K S C D K T H T C P P C P A P E L L G G P S V F L F P P K P K D T L M I S R T P E V T C V V V D V S H E D P E V K F N W Y V D G V E V H N A KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:24 (VH1) (QAQLVQSGPE
LKKPGASVKVSCKASGYLFSNSWMN
WVKQRPGAGLEWIGRIFPGDGDTNY
NGKFKGRATITADKSTSTAYMELSSL
RSEDSAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

An additional aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:25 (VH2) (QAQLVQSG
PEVKKPGASVKVSCKASGYLFSNSW
MNWVKQRPGAGLEWIGRIFPGDGDT
NYNGKFKGRATITADKSTSTAYMELS
SLRSEDTAVYFCARWGLTRDRRLYL
DYWGQGTTVTVSSASTKGPSVFPLAP
SSKSTSGGTAALGCLVKDYFPEPVTV
SWNSGALTSGVHTFPAVLQSSGLYSL
SSVVTVPSSSLGTQTYICNVNHKPSN
TKVDKKVEPKSCDKTHTCPPCPAPEL
LGGPSVFLFPPKPKDTLMISRTPEVT
CVVVDVSHEDPEVKFNWYVDGVEVH
NAKTKPREEQYNSTYRVVSVLTVLH
QDWLNGKEYKCKVSNKALPAPIEKT
ISKAKGQPREPQVYTLPPSRDELTKN
QVSLTCLVKGFYPSDIAVEWESNGQP
ENNYKTTPPVLDSDGSFFLYSKLTVD
KSRWQQGNVFSCSVMHEALHNHYTQ
KSLSLSPGK).

Another aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:26 (VH3) (QAQLVQSGAE
VKKPGASVKVSCKASGYLFSNSWMN
WVKQRRGAGLEWIGRIFPGDGDTNY
NGKFKGRATITADKSTSTAYMELSSL
RSEDTAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:27 (VH4) (QAQLVQSGAE
VKKPGASVKVSCKASGYLFSNSWMN
WVKQRRGAGLEWIGRIFPGDGDTNY
NGKFKGRVTITADKSTSTAYMELSSL
RSEDTAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:28 (VH5) (QAQLVQSGAE
VKKPGASVKVSCKASGYLFSNSWMN
WVKQRRGAGLEWIGRIFPGDGDTNY
NGKFKGRVTITADKSTSTAYMELSSL
RSEDTAVYYCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:12 (VH6) and a light chain comprising the amino acid sequence of SEQ ID NO:14 (Vκ2).

An additional aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:11 (VH5) and a light chain comprising the amino acid sequence of SEQ ID NO:14 (Vκ2).

A further aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:17 (VH6) and a light chain variable region (LCVR) comprising the amino acid sequence of SEQ ID NO:16 (Vκ2).

Another aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:28 (VH5) and a light chain variable region (LCVR) comprising the amino acid sequence of SEQ ID NO:16 (Vκ2).

The present invention also provides an isolated antibody or antigen-binding fragment thereof that binds $\alpha_v\beta_3$ integrin, wherein the antibody or antigen-binding fragment thereof comprises human antibody framework (FR) and constant region sequences and wherein one or more framework region amino acid residues in a light chain variable region is substituted from the corresponding framework region sequence of a murine antibody comprising the light chain variable region amino acid sequence of SEQ ID NO:18 (D I V M S Q S P S S L V V S V G E K V T M S C K S S Q S L L Y S S N Q K N Y L A W Y Q Q K S G Q S P K L L I Y W A S T R E S G V P D R F T G S G S G T D F T L T I S S V K A E D L A V Y Y C K Q Y Y S Y P L T F G A G T K L E L K); Maile et al. "A monoclonal antibody against αVβ3 integrin inhibits development of atherosclerotic lesions in diabetic pigs" *Science Translational Medicine* 2(18):18ra11 (2010)) and in U.S. Pat. Nos. 7,723,483; 8,187,595; and 8,206,706). In some embodiments, the complementarity determining region (CDR) of the light chain variable region of the antibody or antigen binding fragment thereof of this invention can be substituted at amino acid 99 of SEQ ID NO:18 with threonine (S>T substitution).

In one aspect, this invention provides an isolated antibody or antigen binding fragment thereof, comprising one or more framework amino acid residue substitutions selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to A at position 12 in the amino acid sequence of SEQ ID NO:18; d) a substitution of V to L at position 15 in the amino acid sequence of SEQ ID NO:18; e) a substitution of K to R at position 18 in the amino acid sequence of SEQ ID NO:18; f) a substitution of V to A at position 19 in the amino acid sequence of SEQ ID NO:18; g) a substitution of M to I at position 21 in the amino acid sequence of SEQ ID NO:18; h) a substitution of S to N at position 22 in the amino acid sequence of SEQ ID NO:18; i) a substitution of S to P at position 46 in the amino acid sequence of SEQ ID NO:18; j) a substitution of S to A at position 49 in the amino acid sequence of SEQ ID NO:18; k) a substitution of K to R at position 51 in the amino acid sequence of SEQ ID NO:18; l) a substitution of V to L at position 84 in the amino acid sequence of SEQ ID NO:18; m) a substitution of K to Q at position 85 in the amino acid sequence of SEQ ID NO:18; n) a substitution of L to V at position 89 in the amino acid sequence of SEQ ID NO:18; o) a substitution of A to Q at position 106 in the amino acid sequence of SEQ ID NO:18; p) a substitution of L to I at position 112 in the amino acid sequence of SEQ ID NO:18; and q) any combination thereof (SEQ ID NO:19). In some embodiments of the antibody or antigen binding fragment thereof of this paragraph, the complementarity determining region (CDR) of the light chain variable region can be substituted at amino acid 99 of SEQ ID NO:18 or SEQ ID NO:19 with threonine (S>T substitution).

Also provided herein is an isolated antibody or antigen binding fragment thereof, comprising one or more framework amino acid residue substitutions selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to L at position 15 in the amino acid sequence of SEQ ID NO:18; d) a substitution of K to R at position 18 in the amino acid sequence of SEQ ID NO:18; e) a substitution of V to A at position 19 in the amino acid sequence of SEQ ID NO:18; f) a substitution of M to I at position 21 in the amino acid sequence of SEQ ID NO:18; g) a substitution of S to N at position 22 in the amino acid sequence of SEQ ID NO:18; h) a substitution of S to A at position 49 in the amino acid sequence of SEQ ID NO:18; i) a substitution of K to R at position 51 in the amino acid sequence of SEQ ID NO:18; j) a substitution of V to L at position 84 in the amino acid sequence of SEQ ID NO:18; k) a substitution of K to Q at position 85 in the amino acid sequence of SEQ ID NO:18; l) a substitution of L to V at position 89 in the amino acid sequence of SEQ ID NO:18; m) a substitution of A to Q at position 106 in the amino acid sequence of SEQ ID NO:18; n) a substitution of L to I at position 112 in the amino acid sequence of SEQ ID NO:18; and o) any combination thereof (SEQ ID NO:39). In some embodiments of the antibody or antigen binding fragment thereof of this paragraph, the complementarity determining region (CDR) of the light chain variable region can be substituted at amino acid 99 of SEQ ID NO:18 or SEQ ID NO:39 with threonine (S>T substitution).

Further provided herein is an isolated antibody or antigen binding fragment thereof, comprising one or more framework amino acid residue substitutions is selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to A at position 12 in the amino acid sequence of SEQ ID NO:18; d) a substitution of V to L at position 15 in the amino acid sequence of SEQ ID NO:18; e) a substitution of K to R at position 18 in the amino acid sequence of SEQ ID NO:18; f) a substitution of V to A at position 19 in the amino acid sequence of SEQ ID NO:18; g) a substitution of M to I at position 21 in the amino acid sequence of SEQ ID NO:18; h) a substitution of S to N at position 22 in the amino acid sequence of SEQ ID NO:18; i) a substitution of S to P at position 46 in the amino acid sequence of SEQ ID NO:18; j) a substitution of S to A at position 49 in the amino acid sequence of SEQ ID NO:18; k) a substitution of K to R at position 51 in the amino acid sequence of SEQ ID NO:18; l) a substitution of T to S at position 69 in the amino acid sequence of SEQ ID NO:18; m) a substitution of V to L at position 84 in the amino acid sequence of SEQ ID NO:18; n) a substitution of K to Q at position 85 in the amino acid sequence of SEQ ID NO:18; o) a substitution of L to V at position 89 in the amino acid sequence of SEQ ID NO:18; p) a substitution of A to Q at position 106 in the amino acid sequence of SEQ ID NO:18; q) a substitution of L to I at position 112 in the amino acid sequence of SEQ ID NO:18; and r) any combination thereof (SEQ ID NO:40). In some embodiments of the antibody or antigen binding fragment thereof of this paragraph, the complementarity determining region (CDR) of the light chain variable region can be substituted at amino acid 99 of SEQ ID NO:18 or SEQ ID NO:40 with threonine (S>T substitution).

The present invention further provides an isolated antibody or antigen-binding fragment thereof that binds $\alpha_v\beta_3$ integrin, wherein the antibody or antigen-binding fragment thereof comprises human antibody framework (FR) and constant region sequences and wherein one or more framework region amino acid residues in a heavy chain variable region is substituted from the corresponding framework region sequence of a murine antibody comprising the heavy chain variable region amino acid sequence of SEQ ID NO:20 (Q A Q L Q Q S G P E L V K P G A S V E I S C K A S G Y L F S N S W M N W V K Q R P G K G L E W I G R I F P G D G D T N Y N G K F K G K A T L T A D K S S S T A Y M Q L N S L T S E D S A V Y F C A R W G L T R D R R L Y L D Y W G Q G T T L T V S S); Maile et al. "A monoclonal antibody against αVβ3 integrin inhibits development of atherosclerotic lesions in diabetic pigs" *Science Translational Medicine* 2(18):18ra11 (2010)) and in U.S. Pat. Nos. 7,723,483; 8,187,595; and 8,206,706).

The present invention provides an isolated antibody or antigen binding fragment thereof, comprising one or more framework amino acid residue substitutions selected from the group consisting of: a) a substitution of A to V at position 2 in the amino acid sequence of SEQ ID NO:20; b) a substitution of Q to V at position 5 in the amino acid sequence of SEQ ID NO:20; c) a substitution of P to A at position 9 in the amino acid sequence of SEQ ID NO:20; d) a substitution of L to V at position 11 in the amino acid sequence of SEQ ID NO:20; e) a substitution of V to K at position 12 in the amino acid sequence of SEQ ID NO:20; f) a substitution of E to K at position 19 in the amino acid sequence of SEQ ID NO:20; g) a substitution of I to V at position 20 in the amino acid sequence of SEQ ID NO:20; h) a substitution of P to R at position 41 in the amino acid sequence of SEQ ID NO:20; i) a substitution of K to A at position 43 in the amino acid sequence of SEQ ID NO:20; j) a substitution of K to R at position 67 in the amino acid sequence of SEQ ID NO:20; k) a substitution of A to V at position 68 in the amino acid sequence of SEQ ID NO:20; l) a substitution of L to I at position 70 in the amino acid sequence of SEQ ID NO:20; m) a substitution of S to T at position 76 in the amino acid sequence of SEQ ID NO:20; n) a substitution of Q to E at position 82 in the amino acid sequence of SEQ ID NO:20; o) a substitution of N to S at position 84 in the amino acid sequence of SEQ ID NO:20; p) a substitution of T to R at position 87 in the amino acid sequence of SEQ ID NO:20; q) a substitution of S to T at position 91 in the amino acid sequence of SEQ ID NO:20; r) a substitution of F to Y at position 95 in the amino acid sequence of SEQ ID NO:20; s) a substitution of L to V at position 118 in the amino acid sequence of SEQ ID NO:20; and t) any combination thereof (SEQ ID NO:21).

The present invention further provides an isolated antibody or antigen binding fragment thereof, comprising one or more framework amino acid residue substitutions selected from the group consisting of: a) a substitution of Q to V at position 5 in the amino acid sequence of SEQ ID NO:20; b) a substitution of V to K at position 12 in the amino acid sequence of SEQ ID NO:20; c) a substitution of E to K at position 19 in the amino acid sequence of SEQ ID NO:20; d) a substitution of I to V at position 20 in the amino acid sequence of SEQ ID NO:20; e) a substitution of K to A at position 43 in the amino acid sequence of SEQ ID NO:20; f) a substitution of K to R at position 67 in the amino acid sequence of SEQ ID NO:20; g) a substitution of L to I at position 70 in the amino acid sequence of SEQ ID NO:20; h) a substitution of S to T at position 76 in the amino acid sequence of SEQ ID NO:20; i) a substitution of Q to E at position 82 in the amino acid sequence of SEQ ID NO:20; j) a substitution of N to S at position 84 in the amino acid sequence of SEQ ID NO:20; k) a substitution of T to R at position 87 in the amino acid sequence of SEQ ID NO:20; l) a substitution of L to V at position 118 in the amino acid sequence of SEQ ID NO:20; and m) any combination thereof (SEQ ID NO:41).

Additionally provided herein is an isolated antibody or antigen binding fragment thereof, comprising one or more framework amino acid residue substitutions selected from the group consisting of: a) a substitution of Q to V at position 5 in the amino acid sequence of SEQ ID NO:20; b) a substitution of L to V at position 11 in the amino acid sequence of SEQ ID NO:20; c) a substitution of V to K at position 12 in the amino acid sequence of SEQ ID NO:20; d) a substitution of E to K at position 19 in the amino acid sequence of SEQ ID NO:20; e) a substitution of I to V at position 20 in the amino acid sequence of SEQ ID NO:20; f) a substitution of K to A at position 43 in the amino acid sequence of SEQ ID NO:20; g) a substitution of K to R at position 67 in the amino acid sequence of SEQ ID NO:20; h) a substitution of L to I at position 70 in the amino acid sequence of SEQ ID NO:20; i) a substitution of S to T at position 76 in the amino acid sequence of SEQ ID NO:20; j) a substitution of Q to E at position 82 in the amino acid sequence of SEQ ID NO:20; k) a substitution of N to S at position 84 in the amino acid sequence of SEQ ID NO:20; l) a substitution of T to R at position 87 in the amino acid sequence of SEQ ID NO:20; m) a substitution of S to T at position 91 in the amino acid sequence of SEQ ID NO:20; n) a substitution of L to V at position 118 in the amino acid sequence of SEQ ID NO:20; and o) any combination thereof (SEQ ID NO:42).

The present invention additionally provides an isolated antibody or antigen binding fragment thereof, comprising one or more framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of L to I at position 70 in the amino acid sequence of SEQ ID NO:20; k) a substitution of S to T at position 76 in the amino acid sequence of SEQ ID NO:20; l) a substitution of Q to E at position 82 in the amino acid sequence of SEQ ID NO:20; m) a substitution of N to S at position 84 in the amino acid sequence of SEQ ID NO:20; n) a substitution of T to R at position 87 in the amino acid sequence of SEQ ID NO:20; o) a substitution of S to T at position 91 in the amino acid sequence of SEQ ID NO:20; p) a substitution of L to V at position 118 in the amino acid sequence of SEQ ID NO:20; and q) any combination thereof (SEQ ID NO:43).

A further aspect of this invention is an isolated antibody or antigen binding fragment thereof, comprising one or more framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of A to V at position 68 in the amino acid sequence of SEQ ID NO:20; k) a substitution of L to I at position 70 in the amino acid sequence of SEQ ID NO:20; l) a substitution of S to T at position 76 in the amino acid sequence of SEQ ID NO:20; m) a substitution of Q to E at position 82 in the amino acid sequence of SEQ ID NO:20; n) a substitution of N to S at position 84 in the amino acid sequence of SEQ ID NO:20; o) a substitution of T to R at position 87 in the amino acid sequence of SEQ ID NO:20; p) a substitution of S to T at position 91 in the amino acid sequence of SEQ ID NO:20; q) a substitution of L to V at position 118 in the amino acid sequence of SEQ ID NO:20; and r) any combination thereof (SEQ ID NO:44).

An additional aspect of this invention is an isolated antibody or antigen binding fragment thereof, comprising one or more framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of A to V at position 68 in the amino acid sequence of SEQ ID NO:20; k) a substitution of L to I at position 70 in the amino acid sequence of SEQ ID NO:20; l) a substitution of S to T at position 76 in the amino acid sequence of SEQ ID NO:20; m) a substitution of Q to E at position 82 in the amino acid sequence of SEQ ID NO:20; n) a substitution of N to S at position 84 in the amino acid sequence of SEQ ID NO:20; o) a substitution of T to R at position 87 in the amino acid sequence of SEQ ID NO:20; p) a substitution of S to T at position 91 in the amino acid sequence of SEQ ID NO:20; q) a substitution of L to V at position 118 in the amino acid sequence of SEQ ID NO:20; and r) any combination thereof (SEQ ID NO:45).

In various aspects of this invention, the antibody or antigen-binding fragment can be a naked antibody or antigen-binding fragment thereof.

In some aspects of this invention, the antibody or antigen-binding fragment thereof can be conjugated to at least one therapeutic or diagnostic agent. In some embodiments, the therapeutic agent can be but is not limited to, a cytotoxic agent, a chemotherapeutic drug, a radionuclide, an immunomodulator, a hormone, an enzyme, an oligonucleotide, a photoactive therapeutic agent and any combination thereof. In some embodiments, the cytotoxic agent can be a drug or toxin.

The present invention also provides a method of treating a disorder associated with aberrant IGF-1 activity in a subject (e.g., a subject in need thereof), comprising administering to the subject an effective amount of the antibody and/or antigen binding fragment thereof of this invention, thereby inhibiting IGF-1 activity in the subject and treating the disorder, wherein the disorder can be, but is not limited to, kidney disease, nephropathy (e.g., diabetic nephropathy), diabetic kidney disease, renal failure, atherosclerosis, coronary artery disease, peripheral vascular disease, diabetic ulcer, a disease of the eye, retinopathy (e.g., diabetic retinopathy), macular edema (e.g., diabetic macular edema), cancer, nerve damage (e.g., nerve damage in a diabetic patient), neuropathy (e.g., diabetic neuropathy), osteoporosis, pathogenic angiogenesis and any combination thereof. The present invention further provides a method of preventing or minimizing the need for limb amputation in a diabetic patient, comprising administering to the subject an effective amount of an antibody or antigen-binding fragment thereof of this invention.

An additional aspect of the present invention is the use of an isolated antibody or antigen binding fragment thereof as described herein for the manufacture of a medicament for carrying out a method of treatment as described herein.

BRIEF DESCRIPTION OF THE DRAWINGS

FIGS. 2A-C show the percentage reduction in β3 integrin tyrosine phosphorylation (A), AKT serine 473 phosphorylation (B) and MAP kinase (ERK) serine phosphorylation (C) that occurs following the addition of increasing antibody concentrations. The VP12690B antibody was tested over a concentration range from 5 ng/ml to 1000 ng/ml and compared with VH5/Vκ2 antibody. The effects peak at concentrations ranging from 20-50 ng/ml.

FIGS. 3A-D show a dose-dependent increase in the peak blood concentration for each dosage antibody administered. Three doses were administered to five animals in each dosage group. The antibody was administered subcutaneously. These dosages included 0.3 mg/kg, 1.0 mg/kg and 5.0 mg/kg.

DETAILED DESCRIPTION OF THE INVENTION

Figure 1A:
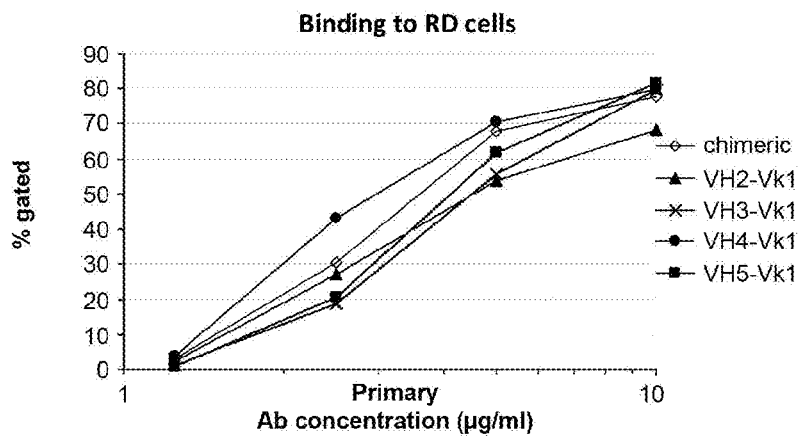
FIGS. 1A-C. RD cell binding assay using NS0-derived Composite Human Antibodies™. The binding of the purified humanized antibodies to RD cells was tested via flow cytometry. Varying concentrations of each humanized antibody were mixed with RD cells expressing alphaV beta3 integrin and binding of human antibody was detected using a PE labeled antibody specific for human IgG heavy chain.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted.

The present invention is based on the discovery of a humanized monoclonal antibody that inhibits the actions of IGF-1, useful, e.g., as a therapeutic agent, imaging and/or diagnostic agent and/or as an agent to deliver therapeutic agents to target cells.

In general, the present invention encompasses a technology to specifically inhibit ligand occupancy of the αVβ3 integrin through an alternative binding site that does not lead to activation of specific intracellular signaling events that can lead to drug toxicity (e.g., by not binding the RGD domain). Administration of antagonists that inhibit the binding of vitronectin to this alternative αVβ3 binding site has been shown to block IGF-1 stimulated activation of PI-3 kinase, MAP kinase, DNA synthesis and cell migration. All of these events are important for IGF-1 to stimulate smooth muscle cell growth within atherosclerotic lesions. Similarly intestinal smooth muscle cells express this integrin so inhibiting IGF-1 actions in this cell type could be useful in the treatment of inflammatory bowel disease. This technology is useful for inhibiting ligand binding to this site on αVβ3 that is expressed on the surface of endothelial cells therefore antagonists that inhibit ligand binding will likely inhibit IGF-1 signaling and therefore could be effective treatments of diabetic retinopathy and for angiogenesis that is associated with tumor formation. The invention involves the development of compounds that inhibit binding and can function as competitive antagonists for binding of extracellular matrix (ECM) ligands that bind to this binding site on the αVβ3 integrin.

This invention helps address major problems in drug development that have inhibited progress in this field. The first problem concerns the IGF-1 receptor. While monoclonal antibodies have been developed that inhibit ligand binding to the IGF-1 receptor, the molecular radius of the binding site on the receptor is large, therefore inhibiting ligand binding to the IGF-1 receptor is a difficult problem in drug development because of the size of the molecule that will be necessary to fully inhibit binding. This invention in contrast inhibits binding to a very small binding site on the αVβ3 integrin. The actual binding site on the integrin itself is encompassed by 8 amino acids and therefore the molecular radius of the binding site is substantially smaller than the ligand binding site to the IGF-1 receptor and it is of a size that allows for easier development of small molecular weight antagonists as opposed to macromolecular antagonists. A second problem with antagonizing the IGF-1 receptor is that it is ubiquitously present on all cells. Therefore if a strategy were formulated to inhibit IGF-1 receptor activity and this were used in combination with therapies that stimulate apoptosis (e.g., a cancer chemotherapeutic or an antiangiogenesis drug), inhibiting IGF-1 action in normal cells could also be associated with extensive apoptosis of normal cell types such as GI epithelium, bone marrow precursor cells and neurons. Therefore the toxicity of a coadministered agent would be greatly amplified. Similarly administering IGF-1 receptor antagonist even without a coadministered agent is likely to lead to inhibition of protein synthesis and possibly to apoptosis in normal cell types. In contrast the antibodies of the present invention selectively target the αVβ3 integrin. Because αVβ3 integrins that signal cooperatively with the IGF-1 receptor are present on vascular endothelial and smooth muscle cells and are usually only expressed in high concentrations in proliferating cells, the antibodies of the present invention are quite selective by specifically targeting these cell types. Cell types such as GI epithelium and bone marrow precursor cells which do not express abundant αVβ3 integrin will likely be spared toxicity. Therefore, the present invention solves the problem of being able to develop macromolecules (e.g., antibodies) that inhibit IGF-1 action and are useful as therapeutics. Secondly, the present invention addresses the major problem of generalized toxicity that would be apparent with any anti-IGF-1 receptor antagonists. Third, the present invention addresses the problem of inhibiting the IGF-1 receptor tyrosine kinase which can also inhibit the insulin receptor tyrosine kinase and lead to the development of diabetes. In addition, the present invention goes beyond previous technologies in this field and provides advantages over such technologies by providing a humanized monoclonal antibody that inhibits ligand binding to the αVβ3 integrin, wherein said monoclonal antibody has reduced immunogenicity in a subject yet the same or similar binding specificity as compared with a nonhumanized monoclonal antibody.

In one aspect, the present invention provides an isolated antibody (e.g., a humanized antibody) or antigen-binding fragment thereof that binds $\alpha_v\beta_3$ integrin, wherein the antibody or antigen-binding fragment thereof comprises the light chain complementarity determining region (CDR) sequences LCDR1 of SEQ ID NO:1 (KSSQSLLYSSNQK-NYLA); LCDR2 of SEQ ID NO:2 (WASTRES); and LCDR3 of SEQ ID NO:3 (KQYYTYPLT).

In a further aspect the present invention provides an isolated antibody (e.g., a humanized antibody) or antigen-binding fragment thereof that binds $\alpha_v\beta_3$ integrin, wherein the antibody or antigen-binding fragment thereof comprises the heavy chain complementarity determining region (CDR) sequences HCDR1 of SEQ ID NO:4 (NSWMN); HCDR2 of SEQ ID NO:5 (IFPGDGDTNYNGKFKG) and HCDR3 of SEQ ID NO:6 (WGLTRDRRLYLDY).

In a further aspect, the present invention provides an isolated antibody (e.g., a humanized antibody) or antigen-binding fragment thereof that binds $\alpha_v\beta_3$ integrin, wherein the antibody or antigen-binding fragment thereof comprises the light chain complementarity determining region (CDR) sequences LCDR1 of SEQ ID NO:1 (KSSQSLLYSSNQK-NYLA); LCDR2 of SEQ ID NO:2 (WASTRES); and LCDR3 of SEQ ID NO:3 (KQYYTYPLT) and the heavy chain complementarity determining region (CDR) sequences HCDR1 of SEQ ID NO:4 (NSWMN); HCDR2 of SEQ ID NO:5 (IFPGDGDTNYNGKFKG) and HCDR3 of SEQ ID NO:6 (WGLTRDRRLYLDY).

In a further aspect, the present invention provides an isolated antibody or antigen-binding fragment thereof that binds $\alpha_v\beta_3$ integrin, wherein the antibody or antigen-binding fragment thereof comprises a heavy chain variable region (HCVR) selected from the group consisting of: a) a HCVR comprising the amino acid sequence of SEQ ID NO:7 (VH1; Q A Q L V Q S G P E L K K P G A S V K V S C K A S G Y L F S N S W M N W V K Q R P G A G L E W I G R I F P G D G D T N Y N G K F K G R A T I T A D K S T S T A Y M E L S S L R S E D S A V Y F C A R W G L T R D R R L Y L D Y W G Q G T T V T V S S); b) a HCVR comprising the amino acid sequence of SEQ ID NO:8 (VH2; Q A Q L V Q S G P E V K K P G A S V K V S C K A S G Y L F S N S W M N W V K Q R P G A G L E W I G R I F P G D G D T N Y N G K F K G R A T I T A D K S T S T A Y M E L S S L R S E D T A V Y F C A R W G L T R D R R L Y L D Y W G Q G T T V T V S S); c) a HCVR comprising the amino acid sequence of SEQ ID NO:9 (VH3; Q A Q L V Q S G A E V K K P G A S V K V S C K A S G Y L F S N S W M N W V K Q R R G A G L E W I G R I F P G D G D T N Y N G K F K G R A T I T A D K S T S T A Y M E L S S L R S E D T A V Y F C A R W G L T R D R R L Y L D Y W G Q G T T V T V S S); d) a HCVR comprising the amino acid sequence of SEQ ID NO:10 (VH4; Q A Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y F C A R W G L T R D R R L Y L D Y W G Q G T T V T V S S); e) a HCVR comprising the amino acid sequence of SEQ ID NO:11 (VH5; Q A Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y C A R W G L T R D R R L Y L D Y W G Q G T T V T V S S); and f) a HCVR comprising the amino acid sequence of SEQ ID NO:12 (VH6; Q V Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y Y C A R W G L T R D R R L Y L D Y W G Q G T T V T V S S).

Also provided herein is an isolated antibody or antigen-binding fragment thereof that binds $\alpha_v\beta_3$ integrin, wherein the antibody or antigen-binding fragment thereof comprises a light chain variable region (LCVR) selected from the group consisting of: a) a LCVR comprising the amino acid sequence of SEQ ID NO:13 (Vκ1; D I V M T Q S P D S L V V S L G E R A T I N C K S S Q S L L Y S S N Q K N Y L A W Y Q Q K S G Q A P R L L I Y W A S T R E S G V P D R F T G S G S G T D F T L T I S S L Q A E D V A V Y Y C K Q Y Y T Y P L T F G Q G T K L E I K); b) a LCVR comprising the amino acid sequence of SEQ ID NO:14 (Vκ2; D I V M T Q S P D S L A V S L G E R A T I N C K S S Q S L L Y S S N Q K N Y L A W Y Q Q K P G Q A P R L L I Y W A S T R E S G V P D R F T G S G S G T D F T L T I S S L Q A E D V A V Y Y C K Q Y Y T Y P L T F G Q G T K L E I K); and c) a LCVR comprising the amino acid sequence of SEQ ID NO:15 (Vκ3; D I V M T Q S P D S L A V S L G E R A T I N C K S S Q S L L Y S S N Q K N Y L A W Y Q Q K P G Q A P R L L I Y W A S T R E S G V P D R F S G S G S G T D F T L T I S S L Q A E D V A V Y Y C K Q Y Y T Y P L T F G Q G T K L E I K).

A further aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:7 (HV1), SEQ ID NO:8 (VH2), SEQ ID NO:9 (VH3), SEQ ID NO:10 (VH4) SEQ ID NO:11 (VH5) or SEQ ID NO:12 (VH6) and a light chain variable region (LCVR) comprising the amino acid sequence of SEQ ID NO:13 (Vκ1), SEQ ID NO:14 (Vκ2) or SEQ ID NO:15 (Vκ3), wherein the HCVR and the LCVR are present in any combination.

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:16 (Vκ2) (D I V M T Q S P D S L A V S L G E R A T I N C K S S Q S L L Y S S N Q K N Y L A W Y Q Q K P G Q A P R L L I Y W A S T R E S G V P D R F T G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C).

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:22 (Vκ1) (D I V M T Q S P D S L V V S L G E R A T I N C K S S Q S L L Y S S N Q K N Y L A W Y Q Q K S G Q A P R L L I Y W A S T R E S G V P D R F T G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C).

A further aspect of this invention is an isolated antibody or antigen-binding fragment thereof that binds $\alpha_v\beta_3$ integrin, wherein the antibody or antigen-binding fragment thereof comprises a light chain comprising the amino acid sequence of SEQ ID NO:23 (Vκ3) (D I V M T Q S P D S L A V S L G E R A T I N C K S S Q S L L Y S S N Q K N Y L A W Y Q Q K P G Q A P R L L I Y W A S T R E S G V P D R FSGSGSGTDFTLTISSLQAEDVAVYY
CKQYYTYPLTFGQGTKLEIKRTVAAP
SVFIFPPSDEQLKSGTASVVCLLNNF
YPREAKVQWKVDNALQSGNSQESVT
EQDSKDSTYSLSSTLTLSKADYEKHK
VYACEVTHQGLSSPVTKSFNRGEC).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:17 (VH6) (QVQLVQSGAE
VKKPGASVKVSCKASGYLFSNSWMN
WVKQRRGAGLEWIGRIFPGDGDTNY
NGKFKGRVTITADKSTSTAYMELSSL
RSEDTAVYYCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:24 (VH1) (QAQLVQSGPE
LKKPGASVKVSCKASGYLFSNSWMN
WVKQRPGAGLEWIGRIFPGDGDTNY
NGKFKGRATITADKSTSTAYMELSSL
RSEDSAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

An additional aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:25 (VH2) (QAQLVQSG
PEVKKPGASVKVSCKASGYLFSNSW
MNWVKQRPGAGLEWIGRIFPGDGDT
NYNGKFKGRATITADKSTSTAYMELS
SLRSEDTAVYFCARWGLTRDRRLYL
DYWGQGTTVTVSSASTKGPSVFPLAP
SSKSTSGGTAALGCLVKDYFPEPVTV
SWNSGALTSGVHTFPAVLQSSGLYSL
SSVVTVPSSSLGTQTYICNVNHKPSN
TKVDKKVEPKSCDKTHTCPPCPAPEL
LGGPSVFLFPPKPKDTLMISRTPEVT
CVVVDVSHEDPEVKFNWYVDGVEVH
NAKTKPREEQYNSTYRVVSVLTVLH
QDWLNGKEYKCKVSNKALPAPIEKT
ISKAKGQPREPQVYTLPPSRDELTKN
QVSLTCLVKGFYPSDIAVEWESNGQP
ENNYKTTPPVLDSDGSFFLYSKLTVD
KSRWQQGNVFSCSVMHEALHNHYTQ
KSLSLSPGK).

Another aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:26 (VH3) (QAQLVQSGAE
VKKPGASVKVSCKASGYLFSNSWMN
WVKQRRGAGLEWIGRIFPGDGDTNY
NGKFKGRATITADKSTSTAYMELSSL
RSEDTAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:27 (VH4) (QAQLVQSGAE
VKKPGASVKVSCKASGYLFSNSWMN
WVKQRRGAGLEWIGRIFPGDGDTNY
NGKFKGRVTITADKSTSTAYMELSSL
RSEDTAVYFCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK
VDKKVEPKSCDKTHTCPPCPAPELLG
GPSVFLFPPKPKDTLMISRTPEVTCV
VVDVSHEDPEVKFNWYVDGVEVHNA
KTKPREEQYNSTYRVVSVLTVLHQD
WLNGKEYKCKVSNKALPAPIEKTISK
AKGQPREPQVYTLPPSRDELTKNQVS
LTCLVKGFYPSDIAVEWESNGQPENN
YKTTPPVLDSDGSFFLYSKLTVDKSR
WQQGNVFSCSVMHEALHNHYTQKSL
SLSPGK).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:28 (VH5) (QAQLVQSGAE
VKKPGASVKVSCKASGYLFSNSWMN
WVKQRRGAGLEWIGRIFPGDGDTNY
NGKFKGRVTITADKSTSTAYMELSSL
RSEDTAVYYCARWGLTRDRRLYLDY
WGQGTTVTVSSASTKGPSVFPLAPSS
KSTSGGTAALGCLVKDYFPEPVTVSW
NSGALTSGVHTFPAVLQSSGLYSLSS
VVTVPSSSLGTQTYICNVNHKPSNTK V D K K V E P K S C D K T H T C P P C P A P E L L G G P S V F L F P P K P K D T L M I S R T P E V T C V V V D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G K).

A further aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:12 (VH6) and a light chain comprising the amino acid sequence of SEQ ID NO:14 (Vκ2).

An additional aspect of this invention is an isolated antibody or antigen-binding fragment thereof that binds $\alpha_v\beta_3$ integrin, wherein the antibody or antigen-binding fragment thereof comprises a heavy chain comprising the amino acid sequence of SEQ ID NO:11 (VH5) and a light chain comprising the amino acid sequence of SEQ ID NO:14 (Vκ2).

A further aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:17 (VH6) and a light chain variable region (LCVR) comprising the amino acid sequence of SEQ ID NO:16 (Vκ2).

Another aspect of this invention is an isolated antibody or antigen-binding fragment thereof that binds $\alpha_v\beta_3$ integrin, wherein the antibody or antigen-binding fragment thereof comprises a heavy chain variable region (HCVR) comprising the amino acid sequence of SEQ ID NO:28 (VH5) and a light chain variable region (LCVR) comprising the amino acid sequence of SEQ ID NO:16 (Vκ2).

The present invention also provides an isolated antibody or antigen-binding fragment thereof that binds $\alpha_v\beta_3$ integrin, wherein the antibody or antigen-binding fragment thereof comprises human antibody framework (FR) and constant region sequences and wherein one or more framework region amino acid residues in a light chain variable region is substituted from the corresponding framework region sequence of a murine antibody comprising the light chain variable region amino acid sequence of SEQ ID NO:18 (D I V M S Q S P S S L V V S V G E K V T M S C K S S Q S L L Y S S N Q K N Y L A W Y Q Q K S G Q S P K L L I Y W A S T R E S G V P D R F T G S G S G T D F T L T I S S V K A E D L A V Y Y C K Q Y Y S Y P L T F G A G T K L E L K); Maile et al. "A monoclonal antibody against αVβ3 integrin inhibits development of atherosclerotic lesions in diabetic pigs" *Science Translational Medicine* 2(18):18ra11 (2010)) and in U.S. Pat. Nos. 7,723,483; 8,187,595; and 8,206,706). In some embodiments, the complementarity determining region (CDR) of the light chain variable region of the antibody or antigen binding fragment thereof can be substituted at amino acid 99 of SEQ ID NO:18 with threonine (S>T substitution).

In one aspect, this invention provides an isolated antibody or antigen binding fragment thereof, comprising one or more (e.g., 1, 2, 3, 4, 5, 6, 7, 8, 9, 10, 11, 12, 13, 14, 15 or 16) framework amino acid residue substitutions selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to A at position 12 in the amino acid sequence of SEQ ID NO:18; d) a substitution of V to L at position 15 in the amino acid sequence of SEQ ID NO:18; e) a substitution of K to R at position 18 in the amino acid sequence of SEQ ID NO:18; f) a substitution of V to A at position 19 in the amino acid sequence of SEQ ID NO:18; g) a substitution of M to I at position 21 in the amino acid sequence of SEQ ID NO:18; h) a substitution of S to N at position 22 in the amino acid sequence of SEQ ID NO:18; i) a substitution of S to P at position 46 in the amino acid sequence of SEQ ID NO:18; j) a substitution of S to A at position 49 in the amino acid sequence of SEQ ID NO:18; k) a substitution of K to R at position 51 in the amino acid sequence of SEQ ID NO:18; l) a substitution of V to L at position 84 in the amino acid sequence of SEQ ID NO:18; m) a substitution of K to Q at position 85 in the amino acid sequence of SEQ ID NO:18; n) a substitution of L to V at position 89 in the amino acid sequence of SEQ ID NO:18; o) a substitution of A to Q at position 106 in the amino acid sequence of SEQ ID NO:18; p) a substitution of L to I at position 112 in the amino acid sequence of SEQ ID NO:18; and q) any combination thereof (SEQ ID NO:19). In some embodiments of the antibody or antigen binding fragment thereof of this paragraph, the complementarity determining region (CDR) of the light chain variable region can be substituted at amino acid 99 of SEQ ID NO:18 with threonine (S>T substitution).

Also provided herein is an isolated antibody or antigen binding fragment thereof, comprising one or more (e.g., 1, 2, 3, 4, 5, 6, 7, 8, 9, 10, 11, 12, 13 or 14) framework amino acid residue substitutions selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to L at position 15 in the amino acid sequence of SEQ ID NO:18; d) a substitution of K to R at position 18 in the amino acid sequence of SEQ ID NO:18; e) a substitution of V to A at position 19 in the amino acid sequence of SEQ ID NO:18; f) a substitution of M to I at position 21 in the amino acid sequence of SEQ ID NO:18; g) a substitution of S to N at position 22 in the amino acid sequence of SEQ ID NO:18; h) a substitution of S to A at position 49 in the amino acid sequence of SEQ ID NO:18; i) a substitution of K to R at position 51 in the amino acid sequence of SEQ ID NO:18; j) a substitution of V to L at position 84 in the amino acid sequence of SEQ ID NO:18; k) a substitution of K to Q at position 85 in the amino acid sequence of SEQ ID NO:18; l) a substitution of L to V at position 89 in the amino acid sequence of SEQ ID NO:18; m) a substitution of A to Q at position 106 in the amino acid sequence of SEQ ID NO:18; n) a substitution of L to I at position 112 in the amino acid sequence of SEQ ID NO:18; and o) any combination thereof (SEQ ID NO:39). In some embodiments of the antibody or antigen binding fragment thereof of this paragraph, the complementarity determining region (CDR) of the light chain variable region can be substituted at amino acid 99 of SEQ ID NO:18 with threonine (S>T substitution).

Further provided herein is an isolated antibody or antigen binding fragment thereof, comprising one or (e.g., 1, 2, 3, 4, 5, 6, 7, 8, 9, 10, 11, 12, 13, 14, 15, 16 or 17) framework amino acid residue substitutions selected from the group consisting of: a) a substitution of S to T at position 5 in the amino acid sequence of SEQ ID NO:18; b) a substitution of S to D at position 9 in the amino acid sequence of SEQ ID NO:18; c) a substitution of V to A at position 12 in the amino acid sequence of SEQ ID NO:18; d) a substitution of V to L at position 15 in the amino acid sequence of SEQ ID NO:18; e) a substitution of K to R at position 18 in the amino acid sequence of SEQ ID NO:18; f) a substitution of V to A at position 19 in the amino acid sequence of SEQ ID NO:18; g) a substitution of M to I at position 21 in the amino acid sequence of SEQ ID NO:18; h) a substitution of S to N at position 22 in the amino acid sequence of SEQ ID NO:18; i) a substitution of S to P at position 46 in the amino acid sequence of SEQ ID NO:18; j) a substitution of S to A at position 49 in the amino acid sequence of SEQ ID NO:18; k) a substitution of K to R at position 51 in the amino acid sequence of SEQ ID NO:18; l) a substitution of T to S at position 69 in the amino acid sequence of SEQ ID NO:18; m) a substitution of V to L at position 84 in the amino acid sequence of SEQ ID NO:18; n) a substitution of K to Q at position 85 in the amino acid sequence of SEQ ID NO:18; o) a substitution of L to V at position 89 in the amino acid sequence of SEQ ID NO:18; p) a substitution of A to Q at position 106 in the amino acid sequence of SEQ ID NO:18; q) a substitution of L to I at position 112 in the amino acid sequence of SEQ ID NO:18; and r) any combination thereof (SEQ ID NO:40). In some embodiments of the antibody or antigen binding fragment thereof of this paragraph, the complementarity determining region (CDR) of the light chain variable region can be substituted at amino acid 99 of SEQ ID NO:18 with threonine (S>T substitution).

The present invention further provides an isolated antibody or antigen-binding fragment thereof that binds $\alpha_v\beta_3$ integrin, wherein the antibody or antigen-binding fragment thereof comprises human antibody framework (FR) and constant region sequences and wherein one or more framework region amino acid residues in a heavy chain variable region is substituted from the corresponding framework region sequence of a murine antibody comprising the heavy chain variable region amino acid sequence of SEQ ID NO:20 (Q A Q L Q Q S G P E L V K P G A S V E I S C K A S G Y L F S N S W M N W V K Q R P G K G L E W I G R I F P G D G D T N Y N G K F K G K A T L T A D K S S S T A Y M Q L N S L T S E D S A V Y F C A R W G L T R D R R L Y L D Y W G Q G T T L T V S S; Maile et al. "A monoclonal antibody against αVβ3 integrin inhibits development of atherosclerotic lesions in diabetic pigs" *Science Translational Medicine* 2(18):18ra11 (2010)) and in U.S. Pat. Nos. 7,723,483; 8,187,595; and 8,206,706).

The present invention provides an isolated antibody or antigen binding fragment thereof, comprising one or more (e.g., 1, 2, 3, 4, 5, 6, 7, 8, 9, 10, 11, 12, 13, 14, 15, 16, 17, 18 or 19) framework amino acid residue substitutions selected from the group consisting of: a) a substitution of A to V at position 2 in the amino acid sequence of SEQ ID NO:20; b) a substitution of Q to V at position 5 in the amino acid sequence of SEQ ID NO:20; c) a substitution of P to A at position 9 in the amino acid sequence of SEQ ID NO:20; d) a substitution of L to V at position 11 in the amino acid sequence of SEQ ID NO:20; e) a substitution of V to K at position 12 in the amino acid sequence of SEQ ID NO:20; f) a substitution of E to K at position 19 in the amino acid sequence of SEQ ID NO:20; g) a substitution of I to V at position 20 in the amino acid sequence of SEQ ID NO:20; h) a substitution of P to R at position 41 in the amino acid sequence of SEQ ID NO:20; i) a substitution of K to A at position 43 in the amino acid sequence of SEQ ID NO:20; j) a substitution of K to R at position 67 in the amino acid sequence of SEQ ID NO:20; k) a substitution of A to V at position 68 in the amino acid sequence of SEQ ID NO:20; l) a substitution of L to I at position 70 in the amino acid sequence of SEQ ID NO:20; m) a substitution of S to T at position 76 in the amino acid sequence of SEQ ID NO:20; n) a substitution of Q to E at position 82 in the amino acid sequence of SEQ ID NO:20; o) a substitution of N to S at position 84 in the amino acid sequence of SEQ ID NO:20; p) a substitution of T to R at position 87 in the amino acid sequence of SEQ ID NO:20; q) a substitution of S to T at position 91 in the amino acid sequence of SEQ ID NO:20; r) a substitution of F to Y at position 95 in the amino acid sequence of SEQ ID NO:20; s) a substitution of L to V at position 118 in the amino acid sequence of SEQ ID NO:20; and t) any combination thereof (SEQ ID NO:21).

The present invention further provides an isolated antibody or antigen binding fragment thereof, comprising one or more (e.g., 1, 2, 3, 4, 5, 6, 7, 8, 9, 10, 11, 12 or 13) framework amino acid residue substitutions selected from the group consisting of: a) a substitution of Q to V at position 5 in the amino acid sequence of SEQ ID NO:20; b) a substitution of V to K at position 12 in the amino acid sequence of SEQ ID NO:20; c) a substitution of E to K at position 19 in the amino acid sequence of SEQ ID NO:20; d) a substitution of I to V at position 20 in the amino acid sequence of SEQ ID NO:20; e) a substitution of K to A at position 43 in the amino acid sequence of SEQ ID NO:20; f) a substitution of K to R at position 67 in the amino acid sequence of SEQ ID NO:20; g) a substitution of L to I at position 70 in the amino acid sequence of SEQ ID NO:20; h) a substitution of S to T at position 76 in the amino acid sequence of SEQ ID NO:20; i) a substitution of Q to E at position 82 in the amino acid sequence of SEQ ID NO:20; j) a substitution of N to S at position 84 in the amino acid sequence of SEQ ID NO:20; k) a substitution of T to R at position 87 in the amino acid sequence of SEQ ID NO:20; l) a substitution of L to V at position 118 in the amino acid sequence of SEQ ID NO:20; and m) any combination thereof (SEQ ID NO:41).

Additionally provided herein is an isolated antibody or antigen binding fragment thereof, comprising one or more (e.g., 1, 2, 3, 4, 5, 6, 7, 8, 9, 10, 11, 12, 13 or 14) framework amino acid residue substitutions selected from the group consisting of: a) a substitution of Q to V at position 5 in the amino acid sequence of SEQ ID NO:20; b) a substitution of L to V at position 11 in the amino acid sequence of SEQ ID NO:20; c) a substitution of V to K at position 12 in the amino acid sequence of SEQ ID NO:20; d) a substitution of E to K at position 19 in the amino acid sequence of SEQ ID NO:20; e) a substitution of I to V at position 20 in the amino acid sequence of SEQ ID NO:20; f) a substitution of K to A at position 43 in the amino acid sequence of SEQ ID NO:20; g) a substitution of K to R at position 67 in the amino acid sequence of SEQ ID NO:20; h) a substitution of L to I at position 70 in the amino acid sequence of SEQ ID NO:20; i) a substitution of S to T at position 76 in the amino acid sequence of SEQ ID NO:20; j) a substitution of Q to E at position 82 in the amino acid sequence of SEQ ID NO:20; k) a substitution of N to S at position 84 in the amino acid sequence of SEQ ID NO:20; l) a substitution of T to R at position 87 in the amino acid sequence of SEQ ID NO:20; m) a substitution of S to T at position 91 in the amino acid sequence of SEQ ID NO:20; n) a substitution of L to V at position 118 in the amino acid sequence of SEQ ID NO:20; and o) any combination thereof (SEQ ID NO:42).

The present invention additionally provides an isolated antibody or antigen binding fragment thereof, comprising one or more (e.g., 1, 2, 3, 4, 5, 6, 7, 8, 9, 10, 11, 12, 13, 14, 15 or 16) framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of L to I at position 70 in the amino acid sequence of SEQ ID NO:20; k) a substitution of S to T at position 76 in the amino acid sequence of SEQ ID NO:20; l) a substitution of Q to E at position 82 in the amino acid sequence of SEQ ID NO:20; m) a substitution of N to S at position 84 in the amino acid sequence of SEQ ID NO:20; n) a substitution of T to R at position 87 in the amino acid sequence of SEQ ID NO:20; o) a substitution of S to T at position 91 in the amino acid sequence of SEQ ID NO:20; p) a substitution of L to V at position 118 in the amino acid sequence of SEQ ID NO:20; and q) any combination thereof (SEQ ID NO:43).

A further aspect of this invention is an isolated antibody or antigen binding fragment thereof, comprising one or more (e.g., 1, 2, 3, 4, 5, 6, 7, 8, 9, 10, 11, 12, 13, 14, 15, 16 or 17) framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of A to V at position 68 in the amino acid sequence of SEQ ID NO:20; k) a substitution of L to I at position 70 in the amino acid sequence of SEQ ID NO:20; l) a substitution of S to T at position 76 in the amino acid sequence of SEQ ID NO:20; m) a substitution of Q to E at position 82 in the amino acid sequence of SEQ ID NO:20; n) a substitution of N to S at position 84 in the amino acid sequence of SEQ ID NO:20; o) a substitution of T to R at position 87 in the amino acid sequence of SEQ ID NO:20; p) a substitution of S to T at position 91 in the amino acid sequence of SEQ ID NO:20; q) a substitution of L to V at position 118 in the amino acid sequence of SEQ ID NO:20; and r) any combination thereof (SEQ ID NO:44).

An additional aspect of this invention is an isolated antibody or antigen binding fragment thereof, comprising one or more (e.g., 1, 2, 3, 4, 5, 6, 7, 8, 9, 10, 11, 12, 13, 14, 15, 16 or 17) framework amino acid residue substitutions selected from the group consisting of: a) a substitution of Q to V at position 5 in the amino acid sequence of SEQ ID NO:20; b) a substitution of P to A at position 9 in the amino acid sequence of SEQ ID NO:20; c) a substitution of L to V at position 11 in the amino acid sequence of SEQ ID NO:20; d) a substitution of V to K at position 12 in the amino acid sequence of SEQ ID NO:20; e) a substitution of E to K at position 19 in the amino acid sequence of SEQ ID NO:20; f) a substitution of I to V at position 20 in the amino acid sequence of SEQ ID NO:20; g) a substitution of P to R at position 41 in the amino acid sequence of SEQ ID NO:20; h) a substitution of K to A at position 43 in the amino acid sequence of SEQ ID NO:20; i) a substitution of K to R at position 67 in the amino acid sequence of SEQ ID NO:20; j) a substitution of A to V at position 68 in the amino acid sequence of SEQ ID NO:20; k) a substitution of L to I at position 70 in the amino acid sequence of SEQ ID NO:20; l) a substitution of S to T at position 76 in the amino acid sequence of SEQ ID NO:20; m) a substitution of Q to E at position 82 in the amino acid sequence of SEQ ID NO:20; n) a substitution of N to S at position 84 in the amino acid sequence of SEQ ID NO:20; o) a substitution of T to R at position 87 in the amino acid sequence of SEQ ID NO:20; p) a substitution of S to T at position 91 in the amino acid sequence of SEQ ID NO:20; q) a substitution of L to V at position 118 in the amino acid sequence of SEQ ID NO:20; and r) any combination thereof (SEQ ID NO:45).

Further provided herein is a nucleic acid molecule that encodes an amino acid sequence of this invention. Such a nucleic acid molecule can be present in a vector or plasmid. Such a nucleic acid molecule, vector or plasmid can be present in a cell (e.g., an isolated cell, transformed cell, host cell). Nonlimiting examples of a nucleic acid molecule of this invention include a nucleic acid molecule comprising, consisting essentially of or consisting of the nucleotide sequence of SEQ ID NO:30 (encoding the amino acid sequence of SEQ ID NO:7; VH1); the nucleotide sequence of SEQ ID NO:31 (encoding the amino acid sequence of SEQ ID NO:8; VH2); the nucleotide sequence of SEQ ID NO:32 (encoding the amino acid sequence of SEQ ID NO:9; VH3); the nucleotide sequence of SEQ ID NO:33 (encoding the amino acid sequence of SEQ ID NO:10; VH4); the nucleotide sequence of SEQ ID NO:34 (encoding the amino acid sequence of SEQ ID NO:11; VH5); the nucleotide sequence of SEQ ID NO:35 (encoding the amino acid sequence of SEQ ID NO:12; VH6); the nucleotide sequence of SEQ ID NO:36 (encoding the amino acid sequence of SEQ ID NO:13; Vκ1); the nucleotide sequence of SEQ ID NO:37 (encoding the amino acid sequence of SEQ ID NO:14; Vκ2); the nucleotide sequence of SEQ ID NO:38 (encoding the amino acid sequence of SEQ ID NO:15; Vκ3); the nucleotide sequence of SEQ ID NO:46, encoding the amino acid sequence of SEQ ID NO:47, which is a Vκ2 light chain variable region and a constant region and includes the signal sequence of amino acids 1-20; however this signal sequence is cleaved off in the active molecule (M E T H S Q V F V Y M L L W L S G V E G D I V M T Q S P D S L A V S L G E R A T I N C K S S Q S L L Y S S N Q K N Y L A W Y Q Q K P G Q A P R L L I Y W A S T R E S G V P D R F T G S G S G T D F T L T I S S L Q A E D V A V Y Y C K Q Y Y T Y P L T F G Q G T K L E I K R T V A A P S V F I F P P S D E Q L K S G T A S V V C L L N N F Y P R E A K V Q W K V D N A L Q S G N S Q E S V T E Q D S K D S T Y S L S S T L T L S K A D Y E K H K V Y A C E V T H Q G L S S P V T K S F N R G E C); and the nucleotide sequence of SEQ ID NO:48, encoding the amino acid sequence of SEQ ID NO:49, which is a VH6 heavy chain variable region and constant region and includes the signal sequence of amino acids 1-19; however this signal sequence is cleaved off in the active molecule (M A W V W T L L F L M A A A Q S I Q A Q V Q L V Q S G A E V K K P G A S V K V S C K A S G Y L F S N S W M N W V K Q R R G A G L E W I G R I F P G D G D T N Y N G K F K G R V T I T A D K S T S T A Y M E L S S L R S E D T A V Y Y C A R W G L T R D R R L Y L D Y W G Q G T T V T V S S A S T K G
P S V F P L A P S S K S T S G G T A A L G C L V K D
Y F P E P V T V S W N S G A L T S G V H T F P A V L
Q S S G L Y S L S S V V T V P S S S L G T Q T Y I C N
V N H K P S N T K V D K K V E P K S C D K T H T C
P P C P A P E L L G G P S V F L F P P K P K D T L M
I S R T P E V T C V V V D V S H E D P E V K F N W Y
V D G V E V H N A K T K P R E E Q Y N S T Y R V V
S V L T V L H Q D W L N G K E Y K C K V S N K A L
P A P I E K T I S K A K G Q P R E P Q V Y T L P P S R
D E L T K N Q V S L T C L V K G F Y P S D I A V E W
E S N G Q P E N N Y K T T P P V L D S D G S F F L Y
S K L T V D K S R W Q Q G N V F S C S V M H E A L
H N H Y T Q K S L S L S P G K).

In some embodiments, the present invention provides an isolated nucleic acid molecule comprising the nucleotide sequence of SEQ ID NO:35 (VH6). In some embodiments, the present invention provides an isolated nucleic acid molecule comprising the nucleotide sequence of SEQ ID NO:37 (Vκ2). These nucleic acid molecules can be present together in a composition and in some embodiments can be present on the same nucleic acid construct.

In some embodiments, the present invention provides an isolated nucleic acid molecule comprising the nucleotide sequence of SEQ ID NO:34 (VH5). In some embodiments, the present invention provides an isolated nucleic acid molecule comprising the nucleotide sequence of SEQ ID NO:37 (Vκ2). These nucleic acid molecules can be present together in a composition and in some embodiments can be present on the same nucleic acid construct.

In some embodiments of this invention, the antibody or antigen-binding fragment thereof of this invention is a naked antibody or naked antigen-binding fragment thereof. As used herein, "naked" means that the antibody or antigen-binding fragment is not operatively linked, conjugated or attached to another moiety or agent.

In some embodiments of this invention, the antibody or antigen-binding fragment thereof of this invention is conjugated to or operatively linked or associated with at least one therapeutic and/or diagnostic agent.

Nonlimiting examples of a therapeutic agent of this invention include a cytotoxic agent (e.g., a drug or toxin), a chemotherapeutic drug, a radionuclide, an immunomodulator, a hormone, an enzyme, an oligonucleotide, a photoactive therapeutic agent and any combination thereof.

The present invention further provides a composition comprising an isolated antibody or antigen binding fragment thereof of this invention and a pharmaceutically acceptable carrier.

The monoclonal antibody or fragment thereof of this invention and the compositions of this invention can be used in various methods. Thus, in one embodiment, the present invention provides a method of treating a disease or disorder (e.g., a disease or disorder associated with aberrant or abnormal IGF-1 activity or a disorder that is responsive to inhibition of IGF-1 activity) in a subject in need thereof, comprising administering to the subject an effective amount of an isolated antibody or antigen binding fragment thereof of this invention, thereby inhibiting IGF-1 activity in the subject and treating the disease or disorder.

Nonlimiting examples of a disease or disorder that can be treated according to the methods of this invention include kidney disease, nephropathy (e.g., diabetic nephropathy), diabetic kidney disease, renal failure, atherosclerosis, coronary artery disease, peripheral vascular disease, diabetic ulcer, a disease of the eye, retinopathy (e.g., diabetic retinopathy), macular edema (e.g., diabetic macular edema), cancer, nerve damage (e.g., nerve damage in a diabetic patient), neuropathy (e.g., diabetic neuropathy), osteoporosis, pathogenic angiogenesis and any combination thereof. The present invention further provides a method of preventing or minimizing the need for limb amputation in a diabetic patient, comprising administering to the subject an effective amount of an antibody or antigen binding fragment thereof of this invention.

Nonlimiting examples of a cancer that can be treated according to the methods of this invention include B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, cervical cancer, endometrial cancer, adenocarcinoma, breast cancer, pancreatic cancer, colon cancer, anal cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, gastrointestinal cancer, and any other cancer now known or later identified (see, e.g., Rosenberg (1996) *Ann. Rev. Med.* 47:481-491, the entire contents of which are incorporated by reference herein).

Definitions

Amino acid sequences of this invention that have been assigned sequence identifiers are set forth in Table 4.

As used herein, "a," "an" and "the" can mean one or more than one, depending on the context in which it is used. For example, "a" cell can mean one cell or multiple cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising."

Also as used herein, "one or more" means one, two, three, four, five, six, seven, eight, nine, ten, 11, 12, 13, 14, 15, 16, 17, 18, 19, 20, etc.

Subjects that may be treated by the present invention include both human subjects for medical purposes and animal subjects for veterinary and drug screening and development purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile and adult subjects.

Amino acid as used herein refers to a compound having a free carboxyl group and a free unsubstituted amino group on the α carbon, which may be joined by peptide bonds to form a peptide active agent as described herein. Amino acids may be standard or non-standard, natural or synthetic, with examples (and their abbreviations) including but not limited to:
Asp=D=Aspartic Acid
Ala=A=Alanine
Arg=R=Arginine
Asn=N=Asparagine
Cys=C=Cysteine
Gly=G=Glycine
Glu=E=Glutamic Acid
Gln=Q=Glutamine
His=H=Histidine
Ile=I=Isoleucine
Leu=L=Leucine
Lys=K=Lysine
Met=M=Methionine
Phe=F=Phenylalanine
Pro=P=Proline
Ser=S=Serine
Thr=T=Threonine
Trp=W=Tryptophan
Tyr=Y=Tyrosine
Val=V=Valine
Orn=Ornithine
Nal=2-napthylalanine
Nva=Norvaline
Nle=Norleucine
Thi=2-thienylalanine
Pcp=4-chlorophenylalanine
Bth=3-benzothienyalanine
Bip=4,4'-biphenylalanine
Tic=tetrahydroisoquinoline-3-carboxylic acid
Aib=aminoisobutyric acid
Anb=.alpha.-aminonormalbutyric acid
Dip=2,2-diphenylalanine
Thz=4-Thiazolylalanine All peptide sequences mentioned herein are written according to the usual convention whereby the N-terminal amino acid is on the left and the C-terminal amino acid is on the right. A short line (or no line) between two amino acid residues indicates a peptide bond.

"Basic amino acid" refers to any amino acid that is positively charged at a pH of 6.0, including but not limited to R, K, and H.

"Aromatic amino acid" refers to any amino acid that has an aromatic group in the side-chain coupled to the alpha carbon, including but not limited to F, Y, W, and H.

"Hydrophobic amino acid" refers to any amino acid that has a hydrophobic side chain coupled to the alpha carbon, including but not limited to I, L, V, M, F, W and C, most preferably I, L, and V.

"Neutral amino acid" refers to a non-charged amino acid, such as M, F, W, C and A.

"αVβ3 integrin cysteine loop domain" as used herein refers to a specific region on the αVβ3 integrin receptor (particularly mammalian receptors, e.g., those found endogenously in the subject being treated) that has not been identified previously as a region that would result in receptor activation, and specifically excludes the RGD binding domain. Agonists that bind in this region include those containing a region of sequence that is commonly termed a heparin binding domain. In general the cysteine loop domain or region of αVβ3 is occurring at amino acids CYDMKTTC (SEQ ID NO:29) at positions 177-184 within the β3 subunit. See, e.g., Vogel et al. "A novel integrin specificity exemplified by binding of the alpha v beta 5 integrin to the basic domain of the HIV Tat protein and vitronectin" *J. Cell Biol.* 121: 461-8 (1993).

"IGF-1" as used herein means insulin-like growth factor 1.

"Treat" or "treating" as used herein refers to any type of treatment that imparts a benefit to a subject that has a disease or disorder or is at risk of having or developing the disease or disorder, including, for example, improvement in the condition of the subject (e.g., in one or more symptoms) and/or slowing of the progression of symptoms, etc.

As used herein, "prevent," "preventing" or "prevention" includes prophylactic treatment of the subject to prevent the onset or advancement of a disorder, as determined, e.g., by the absence or delay in the manifestation of symptoms associated with the disorder. As used herein, "prevent," "preventing" or "prevention" is not necessarily meant to imply complete abolition of symptoms.

"Treatment effective amount," "effective amount," "amount effective to treat" or the like as used herein means an amount of the antibody or fragment thereof of this invention sufficient to produce a desirable effect upon a patient that has cancer, tumors, atherosclerosis, retinopathy, diabetic nephropathy, or any other undesirable medical condition in which IGF-1 is inducing abnormal cellular growth. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. The antibodies may be of any species of origin, including (for example) mouse, rat, rabbit, horse, or human, or may be chimeric or humanized antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. In some embodiments antibodies may be coupled to or conjugated to a detectable group or therapeutic group in accordance with known techniques.

Furthermore, the term "antibody" as used herein, is intended to refer to immunoglobulin molecules comprising four polypeptide chains, two heavy (H) chains and two light (L) chains inter-connected by disulfide bonds. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementary determining regions (CDR), interspersed with regions that are more conserved, termed framework regions (FR). In various embodiments of the antibody or antigen binding fragment thereof of the invention, the FRs may be identical to the human germline sequences, or may be naturally or artificially modified. Each VH and VL is composed of three CDRs and four FRs, arranged from amino-terminus to carboxy-terminus in the following order: FR1, CDR1, FR2, CDR2, FR3, CDR3, FR4.

In general, the antibodies and antigen binding fragments thereof of the present invention possess very high affinities, typically possessing $K_D$ values of from about $10^{-8}$ through about $10^{-12}$ M or higher, for example, at least $10^{-8}$M, at least $10^{-9}$ M, at least $10^{-10}$ M, at least $10^{-11}$ M, or at least $10^{-12}$ M, when measured by binding to antigen presented on cell surface.

The antibodies and antigen binding fragments thereof of the present invention possess very high affinities, typically possessing $EC_{50}$ values of from about $10^{-8}$ through about $10^{-12}$ M or higher, for example, at least $10^{-8}$M, at least $10^{-9}$ M, at least $10^{-10}$ M, at least $10^{-11}$ M, or at least $10^{-12}$ M, when measured by binding to antigen presented on cell surface.

The term "antigen-binding portion" or "antigen-binding fragment" of an antibody (or simply "antibody portion" or "antibody fragment"), as used herein, refers to one or more fragments, portions or domains of an antibody that retain the ability to specifically bind to an antigen. It has been shown that fragments of a full-length antibody can perform the antigen-binding function of an antibody. Examples of binding fragments encompassed within the term "antigen-binding portion" of an antibody include (i) an Fab fragment, a monovalent fragment consisting of the VL, VH, CL1 and CH1 domains; (ii) an F(ab')$_2$ fragment, a bivalent fragment comprising two F(ab)' fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al. (1989) *Nature* 241:544-546), which consists of a VH domain; and (vi) an isolated complementary determining region (CDR). Furthermore, although the two domains of the Fv fragment, VL and VH, are coded for by separate genes, they can be joined, using recombinant methods, by a synthetic linker that enables them to be made as a single contiguous chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies, are also encompassed (see e.g., Holliger et al. (1993) *Proc. Natl. Acad Sci. USA* 90:6444-6448).

The term "epitope" refers to an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of one (or more) linear polypeptide chain(s). A linear epitope is an epitope produced by adjacent amino acid residues in a polypeptide chain. In certain embodiments, an epitope may include other moieties, such as saccharides, phosphoryl groups, or sulfonyl groups on the antigen.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-Isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) *J. Mol. Biol.* 215: 403 410 and Altschul et al. (1997) *Nucleic Acids Res.* 25:3389 402, each of which is herein incorporated by reference in its entirety.

"Therapeutic group" means any suitable therapeutic group, including but not limited to radionuclides, chemotherapeutic agents and cytotoxic agents.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Cytotoxic agent" as used herein includes but is not limited to ricin (or more particularly the ricin A chain), aclacinomycin, diphtheria toxin. Monensin, Verrucarin A, Abrin, Vinca alkaloids, Tricothecenes, and *Pseudomonas* exotoxin A.

"Detectable group" as used herein includes any suitable detectable group, such as radiolabels (e.g. $^{35}$S, $^{125}$I, $^{131}$I, etc.), enzyme labels (e.g., horseradish peroxidase, alkaline phosphatase, etc.), fluorescence labels (e.g., fluorescein, green fluorescent protein, etc.), etc., as are well known in the art and used in accordance with known techniques.

Biological or Biochemical Screening Assays.

Antibodies and antigen binding fragments thereof of this invention can be evaluated for activity in modulating cellular activation by IGF-1 in bioassays or chemical assays of the present invention as discussed further below.

Methods to Assess Biochemical and Biological Activity of Enhancers or Inhibitors of αVβ3.

Modification of IGF-1 actions. In addition to competitive binding assays, in order to determine whether compounds that bind to the cysteine loop binding site on αVβ3 influence IGF-1 signaling, assays can be utilized that assess the biochemical and biologic actions that are stimulated when this site is activated by ligands and how this alters the cellular responses to IGF-1 Inhibitors will obviously inhibit the ability of IGF-1 to stimulate these cellular processes whereas stimulators will facilitate its ability to do so. These assays include but are not limited to the following: β3 subunit phosphorylation, β3 binding to SHPS-1, and integrin associated protein (IAP) as a complex, the association of IAP with SHPS-1, SHPS-1 phosphorylation and Shc recruitment to SHPS-1, Shc phosphorylation, stimulation of DNA synthesis and cell replication or cell migration. Ligands that bind to β3 through the cysteine loop domain often induce both conformational changes and β3 phosphorylation. Similarly, stimulation of β3 phosphorylation can induce a conformational change in β3 secondarily. β3 phosphorylation is measured by applying the compound that binds to β3 to smooth muscle and endothelial cells in culture. First, compounds are added using concentrations varying from 0.1 to 1 μg/ml to confluent smooth muscle or endothelial cell monolayers in 10 cm dishes. Following a fixed time period of exposure to the cells (2-4 hrs) the cells are lysed in 900 μl of RIPA buffer. The lysates are either analyzed directly by immunoblotting for β3 to measure polymerization or immunoprecipitated with an anti β3 antibody and then immunoblotted for phosphotyrosine. Immunoblotting is analyzed following separation of the proteins contained in 30 μl of cell lysate by SDS polyacrylamide gel electrophoresis (SDS-PAGE). For immunoprecipitation, the primary β3 antibody is added at a 1:300 dilution to 900 μl of lysate and incubated overnight. The immune complexes are precipitated with protein A sepharose and eluted with Laemmli sample buffer (Maile L A and Clemmons D R, *Endocrinology* 143: 4259-4264 (2002); Maile L A, Clarke J B, Clemmons D R, *J Biol Chem,* 277:8955-8960 (2002)). The amount of phosphorylated β3 is then determined by SDS-PAGE followed by immunoblotting with a monoclonal anti-phosphotyrosine antibody (PY99) (Ling Y, Maile L A, Clemmons D R, *Mol Endocrinol,* 17:1824-1833 (2003)).

The methodology for determining complex formation between SHPS-1 and IAP has been previously published (Maile L A, Clarke J B, Clemmons D R, *Mol Biol Cell,* 14:3519-28 (2003)). Briefly the cells are exposed to test agents that activate β3 through the cysteine loop domain and then they are exposed to IGF-1. Following IGF-1 exposure, if β3 is ligand occupied by an activating ligand IAP and SHPS-1 will associate in a large molecular weight complex. Importantly if this is completely inhibited by antibody that binds to the cysteine loop domain or other inhibitors, they will not associate. To detect this complex, cell lysates are prepared as described previously and immunoprecipitated for SHPS-1 using a 1:330 dilution of a polyclonal antiserum. The immunoprecipitated proteins are separated by SDS-PAGE and immunoblotted using a purified monoclonal antibody to detect IAP (B6H12) (Id.).

SHPS-1 Phosphorylation.

To determine SHPS-1 phosphorylation the β3 ligand is added to the cultures for periods between 30 minutes and 2 hrs at 37° C. IGF-1 is then added and cell lysates are prepared at specific time points. In addition to baseline, 3, 5, 10, and 20 min lysates are prepared after exposure to IGF-1. The lysates are prepared as described previously and immunoprecipitated for SHPS-1 using anti-SHPS-1 polyclonal antiserum at a 1:330 dilution. The immunoprecipitate which is pelleted with protein A sepharose is then analyzed by SDS-PAGE followed by immunoblotting for phosphotyrosine using the PY99 monoclonal antibody that detects phosphorylated tyrosine residues (Maile L A and Clemmons D R, *Endocrinology* 143: 4259-4264 (2002); Maile L A, Clarke J B, Clemmons D R, *J Biol Chem,* 277:8955-8960 (2002); Maile L A and Clemmons D R *Circ Res,* 93: 925-931 (2003)). The expected response is that IGF-1 stimulates SHPS-1 phosphorylation and that agonists will increase either the intensity of SHPS-1 phosphorylation or prolong its duration. In contrast, antagonists will decrease the intensity and shorten its duration.

Shc Phosphorylation.

The binding and recruitment of Shc to SHPS-1 is critical for Shc phosphorylation which is necessary for IGF-1 signaling particularly in smooth muscle cells and endothelium in diabetes. To measure Shc phosphorylation, cell cultures are exposed to agonists or antagonists as described previously and then cell cultures are then exposed to IGF-1 for periods of 10, 20 or 30 minutes. Cell lysates are prepared at each time point as described previously and immunoprecipitated using a 1:1000 dilution of anti-Shc polyclonal antiserum. The immunoprecipitate is cleared with protein A sepharose and then the proteins are eluted with Laemmli sample buffer and analyzed by SDS-PAGE followed by immunoblotting with the anti phosphotyrosine antibody PY99. The expected response is that IGF-1 will stimulate Shc phosphorylation. This will be significantly prolonged and intensified particularly at the later time points in cultures exposed to β3 agonists. In contrast, antagonists will inhibit Shc phosphorylation.

Shc Recruitment to SHPS-1.

Cultures are exposed to either agonists or antagonists for the time periods listed previously. Cultures are then washed and IGF-1 is added for periods of 5, 10, 20 or 30 min. Cell lysates are prepared as described previously (Maile L A and Clemmons D R, *Endocrinology* 143: 4259-4264 (2002)) and immunoprecipitated using anti-SHPS-1 antisera using a 1:330 dilution. Following clearing of the immune complexes with protein A sepharose, the immunoprecipitates are analyzed by SDS-PAGE followed by immunoblotting for Shc using a 1:2000 dilution of anti-Shc antiserum. The expected response is that IGF-1 will stimulate Shc recruitment to SHPS-1 which is required for Shc to undergo phosphorylation. However if an antagonist is used, then SHPS-1 will not be phosphorylated and Shc will not bind to SHPS-1 therefore recruitment will be undetectable or greatly diminished.

Activation of MAP Kinase.

Activation of MAP kinase is critical for stimulation of cell division and cell migration in smooth muscle cells and endothelium by IGF-1. Shc phosphorylation and recruitment to the membrane as noted previously is required for MAP kinase activation. To determine if MAP kinase activation is impaired, cells are exposed to agonists or antagonists for the periods of time described previously then cell lysates prepared as described previously (Maile L A and Clemmons D R *Circ Res*, 93: 925-931 (2003)). 30 µl of cell lysate is analyzed directly by SDS-PAGE with immunoblotting for the phosphorylated form of ERK 1/2 (an indication of MAP kinase activity) (Ling Y, Maile L A, Clemmons D R, *Mol Endocrinol*, 17:1824-1833 (2003)). It would be anticipated that the time course intensity of MAP kinase activation will be prolonged by β3 agonists and inhibited by β3 agonists.

Cell Replication.

Smooth muscle and/or endothelium cells are plated at relatively low density, $10^4/cm^2$ in low serum (0.2%) containing medium. 24 hr after plating, cells are quiesced in 0.2% platelet poor plasma containing medium. 24 hr later the cultures are exposed to increasing concentrations of IGF-1 between 0 and 100 ng/ml and the β3 agonists or antagonists. After 48 hr, the cell cultures are stained with trypan blue and the cell number is determined by manual counting. If β3 is occupied by an agonist then there is at least a 2 fold increase in cell number over this time period. Whereas if an antagonist is added there is often less than 20% increase in cell number.

Cell Migration.

Confluent quiescent smooth muscle or endothelial cell cultures are wounded with a razor blade as described in Maile L A, Imai Y, Clarke J B, Clemmons D R, *J. Biol. Chem*, 277:1800-1805 (2002). The wounds are examined to determine that a straight edge has been obtained and there are no grooves in the plate. At least five areas that are correctly wounded are then identified with a colored marker. IGF-1 is added at concentrations of either 50 or 100 ng/ml and various concentrations of the agonists or antagonists are added to at least duplicate cultures. After 72 hr, the number of cells that have migrated at least 50 microns from the wound edge is determined and counted following staining with methylene blue. IGF-1 normally stimulates between 20 and 50 cells per microscopic field to migrate this distance. In the presence of an antagonist, there are generally fewer than 5 cells/microscopic field that migrate but agonists may increase the response to IGF-1 by as much as 2 fold.

Formulations and Administration

For administration in the methods of use described below, the active agent (e.g., the antibody or antigen-binding fragment thereof) will generally be mixed, prior to administration, with a non-toxic, pharmaceutically acceptable carrier substance (e.g. normal saline or phosphate-buffered saline), and will be administered using any medically appropriate procedure, e.g., parenteral administration (e.g., injection) such as by intravenous or intra-arterial injection.

The active agents described above may be formulated for administration in a pharmaceutical carrier in accordance with known techniques. See, e.g., Remington, *The Science And Practice of Pharmacy* (latest edition). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the subject. The carrier may be a liquid and is preferably formulated with the compound as a unit-dose formulation which may contain from 0.01 or 0.5% to 95% or 99% by weight of the active compound. The carrier may be sterile or otherwise free from contaminants that would be undesirable to administer or deliver to a subject.

Formulations of the present invention suitable for parenteral administration comprise sterile aqueous and non-aqueous injection solutions of the active compound, which preparations are preferably isotonic with the blood of the intended subject. These preparations may contain anti-oxidants, buffers, bacteriostats and solutes which render the formulation isotonic with the blood of the intended subject.

The active agents may be administered by any medically appropriate procedure, e.g., normal intravenous or intra-arterial administration. In certain cases, direct administration to an atherosclerotic vessel may be desired.

Active agents may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

Dosage of the antibody or antigen binding fragment thereof of this invention for the methods of use described herein will depend, among other things, the condition of the subject, the particular disorder being treated, the route of administration, the nature of the therapeutic agent employed, and the sensitivity of the subject to the particular therapeutic agent. For example, the dosage range can be from about 0.02 to about 500 micrograms per kilogram subject body weight. The specific dosage of the antibody or antigen binding fragment thereof is not critical, as long as it is effective to result in some beneficial effects in some individuals within an affected population. In general, the dosage may be as low as about 0.05, 0.1, 0.5, 1, 5, 10, 20 or 50 micrograms per kilogram subject body weight, or lower, and as high as about 60, 75, 90 or 100 micrograms per kilogram subject body weight, or even higher.

Methods of Use

Antagonism of IGF-1 action has been shown to block lesion formation and early atherosclerotic lesion development. Administration of an antibody or fragment thereof that blocks this binding site on αVβ3 would antagonize the effect of matrix proteins that are abundant in atherosclerotic lesions such as vitronectin, osteopontin and fibrinogen. To the extent that heparin binding epidermal growth factor and connective tissue growth factor are active in atherosclerotic lesion development, the antibody or fragment thereof would also act to inhibit their effects.

The early changes in diabetic nephropathy include the development of proteinuria due to dysfunction of the glomerular endothelial/podocyte barrier. The normal function of this barrier is to filter waste into urine and to keep proteins >40,000 molecular weight in the circulation. Barrier dysfunction then leads to glomerular basement membrane thickening and podocyte foot process fusion. Following these changes, podocytes detach from the basement membrane and the remaining glomerulus becomes fibrotic and dysfunctional. These changes are progressive and occur over several months to years. The alphaVbeta3 integrin has been implicated in the development of diabetic nephropathy. This receptor is expressed on the surface of glomerular endothelial cells and podocytes. It is abnormally activated in the presence of hyperglycemia and ligands that are known to be synthesized in the kidney such as osteopontin bind alphaV-beta3 to cause this abnormal activation.

An antibody directed against the region that is activated by excessive alpha V beta 3 ligand accumulation has been developed and is disclosed herein. When the antibody binds to a region of alphaVbeta3 termed the C loop domain, it inhibits the ability of these ligands to stimulate increased endothelial cell permeability to protein. This results in maintenance of the normal endothelial/podocyte barrier. This has been demonstrated in Sprague-Dawley rats that had been administered a compound to destroy their insulin producing cells in the pancreas. These rats became diabetic over a four-week period and developed highly significant proteinuria. However even after the development of significant proteinuria, administration of the anti C loop domain antibody resulted in it binding to the appropriate cells in the glomerulus (e.g., endothelial cells and podocytes) and in inhibition of the ability of osteopontin and other ligands to stimulate glomerular endothelial permeability. This was manifested by return of the degree of abnormal proteinuria to normal within four weeks of administration. The antibodies of the present invention are effective in stopping the earliest changes in glomerular function that can be demonstrated in diabetic nephropathy (Kanwar et al. "A glimpse of various pathogenetic mechanisms of diabetic nephropathy" *Annu Rev Pathol Mech Dis* 6:395-423 (2011); Nakagawa et al. "Endothelial dysfunction as a potential contributor in diabetic nephropathy" *Nat Rev Nephrol* 7:36-44 (2011); Diez-Sampedro "Podocytopathy in diabetes: a metabolic and endocrine disorder" *Am J Kidney Dis* 58:637-646 (2011); Nicholas et al. "Critical role for osteopontin in diabetic nephropathy" 77:588-600 (2010); Ktisiou "Glucose-Induced changes in integrins and matrix-related functions in culture human glomerular epithelial cells" *Am J Physiol Renal Physiol* 284:F671-679 (2003); Yamamoto et al. "Tumstatin peptide, an inhibitor of angiogenesis, prevents glomerular hypertrophy in the early stage of diabetic nephropathy" *Diabetes* 53:1831-1840 (2004); Wei et al. "Modification of kidney barrier function by the urokinase receptor" *Nature Med* 14(1):55-63 (2008)).

Another use of the antibodies and fragments thereof of this invention would be to treat inflammatory bowel disease. Intestinal smooth muscle cells express αVβ3 receptors and their proliferation in these diseases leads to intestinal strictures. Therefore inhibiting their growth with an antibody or fragment thereof of this invention could lead to prevention of this complication.

Another use of antibodies and fragments thereof of the invention is in the treatment of osteoporosis. Osteoblasts do not express αVβ3 but it is expressed on osteoclasts which stimulate bone reabsorption. Therefore inhibition of stimulation of ligand occupancy on osteoclasts should result in enhancement of bone formation through the use of antagonist. Several proteins such as osteopontin are abundant in bone extracellular matrix and could be stimulating osteoclasts through this mechanism therefore antagonism of their action may allow IGF-1 to increase bone formation without increasing bone resorption.

Another use of antibodies and fragments thereof of this invention is to treat states of abnormal angiogenesis. Angiogenesis is important in tumor development but it is as important in other pathophysiologic processes such as diabetic retinopathy. Since endothelial cells express abundant αVβ3 receptors, antagonists that inhibit the binding of endothelial growth factors such as vascular endothelial growth factor or heparin binding epidermal growth factor to αVβ3 through this heparin binding domain would be expected to lead to inhibition of angiogenesis therefore the antibodies and fragments thereof of this invention can be useful drugs for these clinical conditions.

Another use of antibodies and fragments thereof of this invention is to treat cancers or tumors, particularly those that have αVβ3 receptors (e.g., Wilm's tumor, nephroblastoma, neuroblastoma). Although αVβ3 is not an abundant receptor on all tumor cells, several tumor cell types that express αVβ3 have been described. Approaches to date have generally targeted the RGD sequence in ligands that stimulate αVβ3 and used antagonists that are binding to this domain to inhibit αVβ3 actions. In the present invention, antagonizing the cysteine loop on αVβ3 provides a unique approach to targeting this receptor as opposed to the RGD binding site and thus may have greater efficacy inhibiting the development of these tumors.

In the treatment of cancers or tumors the antibodies and antigen binding fragments thereof of the present invention may optionally be administered in conjunction with other, different, cytotoxic agents such as chemotherapeutic or antineoplastic compounds or radiation therapy useful in the treatment of the disorders or conditions described herein (e.g., chemotherapeutics or antineoplastic compounds). The other compounds may be administered prior to, concurrently and/or after administration of the antibodies or antigen binding fragments thereof of this invention. As used herein, the word "concurrently" means sufficiently close in time to produce a combined effect (that is, concurrently may be simultaneously, or it may be two or more administrations occurring before or after each other).

As used herein, the phrase "radiation therapy" includes, but is not limited to, x-rays or gamma rays which are delivered from either an externally applied source such as a beam or by implantation of small radioactive sources.

Nonlimiting examples of suitable chemotherapeutic agents which may be administered with the antibodies or antigen binding fragments as described herein include daunomycin, cisplatin, verapamil, cytosine arabinoside, aminopterin, democolcine, tamoxifen, Actinomycin D, Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine, Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxycoformycin, Mitomycin-C, L-Asparaginase, Interferons (especially IFN-α), Etoposide, and Teniposide; Other anti-proliferative cytotoxic agents are navelbene, CPT-11, anastrazole, letrazole, capecitabine, reloxafine, cyclophosphamide, ifosamide, and droloxafine. Additional anti-proliferative cytotoxic agents include, but are not limited to, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin® (trastuzumab). (see, e.g., U.S. Pat. No. 6,537,988; U.S. Pat. No.

6,420,377). Such compounds may be given in accordance with techniques currently known for the administration thereof.

Antibodies

Antibodies and the production thereof are known. See, e.g., U.S. Pat. No. 6,849,719; see also U.S. Pat. Nos. 6,838,282; 6,835,817; 6,824,989.

Antibodies of the invention include antibodies that are modified, i.e., by the covalent attachment of any type of molecule to the antibody such that covalent attachment does not prevent the antibody from specifically binding to its binding site. For example, antibodies of the invention may be modified, e.g., by glycosylation, acetylation, pegylation, phosphorylation, amidation, or with other protecting/blocking groups, proteolytic cleavage, linkage to a cellular ligand or other protein, etc. Any of numerous chemical modifications may be carried out by known techniques, including but not limited to specific chemical cleavage, acetylation, formylation, metabolic synthesis of tunicamycin, etc. Additionally, the antibodies may contain one or more non-classical amino acids.

Monoclonal antibodies can be prepared using a wide variety of techniques including the use of hybridoma, recombinant, and phage display technologies, or a combination thereof. For example, monoclonal antibodies can be produced using hybridoma techniques including those taught, for example, in Harlow et al., *Antibodies: A Laboratory Manual*, (Cold Spring Harbor Laboratory Press, 2nd ed. 1988); and Hammerling et al., *Monoclonal Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and known. Briefly, mice are immunized with an antigen or a cell expressing such antigen. Once an immune response is detected, e.g., antibodies specific for the antigen are detected in the mouse serum, the mouse spleen is harvested and splenocytes isolated. The splenocytes are then fused by known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide or antigen of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CHI domain of the heavy chain.

For example, antibodies can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include but are not limited to those disclosed in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described above, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art.

Examples of techniques which can be used to produce single-chain Fvs and antibodies include those described in U.S. Pat. Nos. 4,946,778 and 5,258,498; Huston et al. *Methods in Enzymology* 203:46-88 (1991); Shu et al. *PNAS* 90:7995-7999 (1993); and Skerra et al. *Science* 240:1038-1040 (1988).

For some uses, including in vivo use of antibodies in humans and in vitro detection assays, it may be preferable to use chimeric, deimmunized, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison. *Science* 229:1202 (1985); Oi et al. *BioTechniques* 4:214 (1986); Gillies et al. (1989) *J. Immunol. Methods* 125:191-202; U.S. Pat. Nos. 5,807,715; 4,816,567; and 4,816,397, all of which are incorporated herein by reference in their entireties.

The term "humanized" as used herein refers to antibodies from non-human species whose amino acid sequences have been modified to increase their similarity to antibody variants produced naturally in humans. Thus, humanized antibodies are antibody molecules from a non-human species antibody that binds the desired antigen, having one or more complementarity determining regions (CDRs) from the non-human species and framework regions from a human immunoglobulin molecule. Often, framework residues in the human framework regions will be substituted with the corresponding residue from the donor antibody to alter, preferably to improve, antigen binding and/or reduce immunogenicity of the humanized antibody in a subject. These framework substitutions are identified by methods well known in the art, e.g., by modeling of the interactions of the CDR and framework residues to identify framework residues important for antigen binding and/or immunogenicity and sequence comparison to identify unusual framework residues at particular positions. (See, e.g., Queen et al. U.S. Pat. No. 5,585,089; Riechmann et al. *Nature* 332:323 (1988), which are incorporated herein by reference in their entireties.) Antibodies can be humanized using a variety of techniques known in the art including, for example, CDR-grafting (see, e.g., U.S. Pat. Nos. 5,225,539; 5,530,101; and 5,585,089), veneering or resurfacing (see, e.g., EP Patent No. 592,106; EP Patent No. 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332). A detailed description of the production and characterization of the humanized monoclonal antibodies of the present invention is provided in the Examples section herein.

Completely human antibodies are desirable for therapeutic treatment, diagnosis, and/or detection of human subjects. Human antibodies can be made by a variety of methods known in the art including phage display methods described above using antibody libraries derived from human immunoglobulin sequences. See, e.g., U.S. Pat. Nos. 4,444,887 and 4,716,111.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,413,923; 5,625,126; 5,633,425; 5,569,825; 5,661,016; 5,545,806; 5,814,318 and 5,939,598.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-1diotype antibodies that "mimic" polypeptides of the invention using techniques well known to those skilled in the art. (See, e.g., Greenspan & Bona, *FASEB J.* 7(5):437-444; (1989) and Nissinoff, *J. Immunol.* 147(8):2429-2438 (1991)). For example antibodies which bind to and competitively inhibit polypeptide multimerization and/or binding of a polypeptide of the invention to a ligand can be used to generate anti-1diotypes that "mimic" the polypeptide multimerization and/or binding domain and, as a consequence, bind to and neutralize polypeptide and/or its ligand. Such neutralizing anti-1diotypes or Fab fragments of such anti-1diotypes can be used in therapeutic regimens to neutralize polypeptide ligand. For example, such anti-1diotypic antibodies can be used to bind a polypeptide of the invention and/or to bind its ligands/receptors, and thereby block its biological activity.

The invention further provides polynucleotides comprising a nucleotide sequence encoding an antibody or portion thereof of the invention as described above. The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which involves the synthesis of overlapping oligonucleotides containing portions of the sequence encoding the antibody, annealing and ligation of those oligonucleotides, and then amplification of the ligated oligonucleotides by PCR. Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Implants

Active compounds of the invention, particularly antibodies or antigen binding fragments thereof as described above, may be coupled to or conjugated to implants or implantable medical devices in accordance with known techniques for carrying out the methods described herein, or for combating problems associated with the implant such as stenosis and restenosis. See, e.g., U.S. Pat. Nos. 6,786,922; 6,746,686; 6,718,208; 6,617,142; 6,352,832; and 6,238,872. Any implant can be so utilized, including but not limited to stents (e.g., vascular stents), electrodes, catheters, leads, implantable pacemaker or cardioverter housings, joints, screws, rods, ophthalmic implants (including, but not limited to, intraocular lens implants, glaucoma implants or drainage implants, and punctal implants or plugs), etc. The implants may be of any suitable material, including but not limited to organic polymers (including stable or inert polymers and biodegradable polymers), metals such as stainless steel and titanium, inorganic materials such as silicon, and composites thereof.

The present invention is explained in greater detail in the following non-limiting examples.

EXAMPLE 1

DNA Synthesis

Cells were plated at a density of $2.5 \times 10^4/cm^2$ in 96-well tissue culture plates and grown for 5 days without a medium change. They were rinsed once with serum-free DMEM and serum starved by incubating with DMEM plus 0.2% platelet poor plasma (PPP) for 24 h. The cells were then exposed to IGF-1 plus any treatment and incubated at 37° C. for 24 h, and the amount of [$^3$H]thymidine incorporated into DNA was determined as described in: Imai and Clemmons ("Roles of Phosphatidylinositol 3-Kinase and Mitogen-Activated Protein Kinase Pathways in Stimulation of Vascular Smooth Muscle Cell Migration and Deoxyriboncleic Acid Synthesis by Insulin-Like Growth Factor 1" *Endocrinology* 140:4228-4235 (1999)).

EXAMPLE 2

Peptide Synthesis

Peptides were synthesized using FMOC chemistry on a Rainin Multiple Peptide synthesizer. Activation of FMOC amino acids and acylation utilized HATU in the presence of a base (N methyl morpholine). Upon completion of acylation, the FMOC protecting group was removed with 20% piperidine in dimethylformamide. After synthesis, the peptide was removed from the resin and deprotected by treatment with 95% trifluoroacetic acid containing appropriate organic scavengers.

Cleaved, deprotected peptides were precipitated in cold ether, resuspended in a dilute TFA/acetonitrile mix, and purified by high performance liquid chromatography on a reverse phase resin with an increasing acetonitrile gradient.

Quality control of the peptide product was assessed by analytical HPLC and by matrix assisted laser desorption ionization time-of-flight mass spectrometry. Purified peptide was lyophilized and stored at –20° C.

EXAMPLE 3

Preparation of Peptide for Immunization

In order to prepare an antibody of this invention, a synthetic peptide was prepared.

The peptide was synthesized using FMOC chemistry using a Rainin multiple peptide synthesizer. Activation of FMCO amino acids and acylation utilizes HTAU in the presence of a base (n-methylmorpholine). Upon completion of acylation, the FMOC protecting group was removed with 20% piperidine in dimethylformamide. After synthesis, the peptide was removed from the resin and deprotected by treatment with 95% triflouroacetic acid containing appropriate organic scavengers. Cleaved and deprotected peptide was then precipitated with cold ether and resuspended in dilute TFA/acetonitrile and purified by high performance liquid chromatography on a reverse phase resin and eluted with an increasing acetonitrile gradient. The quality of the peptide product was assessed by analytical HPLC and by matrix assisted laser desorption ionization time-of-flight mass spectrometry. The purified peptide was then lyophilized and stored at –20 C. The mass of eluting peptide was verified as containing the correct amino acids by comparison to the known masses in the database.

The β3 cysteine loop peptide (CYDMKTTC) (SEQ ID NO:29) was conjugated to Imject Maleimide Activated Mariculture Keyhole Limpet Hemocyanin (Pierce, Rockford, Ill.). 0.7 mg, 1.2 mg and 2.1 mg amounts of peptide were weighed and each was dissolved separately before addition to KLH in 500 mcl of 0.03M $NaH_2PO_4$, pH 7.2 containing 0.9M sodium chloride. 2 mg of maleimide activated KLH was dissolved in 500 mcl of distilled water. 0.7 mg of dissolved peptide was then added to the KLH solution and incubated at room temperature for 20 min. An additional tube containing 0.7 mg of peptide dissolved in buffer and added to the same KLH solution was incubated again for 25 min at room temperature. 1.2 mg and 2.1 mg of peptide were sequentially added to the KLH solution and further incubated for 1 hr intervals after each addition, at room temperature. The peptide conjugate was removed and dialyzed 24 hr against 2 L of 0.083M sodium $H_2PO_4$, pH 7.2, 0.9M NaCl with one exchange. The total 4.7 mg of peptide/KLH conjugate was divided into 5 equal aliquots, lyophylized and frozen at –20° C. for later use.

EXAMPLE 4

Production and Screening of Monoclonal Antibodies

Immunization.

Pathogen-free BALB/c mice were utilized for immunization. The conjugated cysteine loop peptide (CYDMKTTC; SEQ ID NO:29) described above was mixed with emulsified mouse RIBI (MPL+TDDTM emulsion) adjuvant and 300 mcg of the emulsified antigen injected intraperitoneally. The injections were repeated at three week intervals, twice. Antibody titers were determined by withdrawing 50-100 mcl of blood from the tail vein at these three week intervals. The titer was determined by testing the reactivity of the mouse serum for immobilized β3 antigen. In mice in which sufficient antibody titer was obtained after six weeks, the mice were sacrificed and the spleens and lymph nodes removed for fusion to myeloma cells for hybridoma formation.

Hybridoma Formation.

Two mice were selected for spleen harvest. These mice were boosted a third time with 300 mcg of antigen then sacrificed four days later. Blood and spleen were collected. Spleen cells were harvested and fused with 63-AGA.65 (ATCCCRL-1580) cells using a 50% PEG solution. These fused cells were then plated in a 96 well plate at $1 \times 10^5$ cells per well in HAT selection medium. After 12-14 days the fusion plates or clones were fed in HT media. Medium was collected for screening by ELISA to identify desired hybridoma cells.

ELISA Materials.

The ELISA was carried out with the following materials:
96 well Immulon IV plates (Fisher Cat #14-245-153)
1× coating buffer (0.05M carbonate/bicarbonate buffer pH 9.6 Sigma Cat # C3041)
2% BSA in PBS (Blocking Buffer)
0.5% BSA in PBS (ELISA Buffer)
0.05% Tween PBS (Wash buffer)
DEA Developer
The DEA Developer (for 500 ml) was produced from 4.8 ml of 85% Diethanolamine (Fisher Cat # D45); 0.25 ml of 1M $MgCl_2$; and pNPP tablets (Sigma Cat # N2765). To prepare the developer, DEA was dissolved in 400 ml of sterile water and pH was adjusted to 10 with HCl and NaOH. MgCl$_2$ was added. The volume was adjusted to 500 ml. Storage was at 4° C. The developer was wrapped in foil to protect from light. Immediately before use 1 tablet of pNPP was added to 20 ml of buffer.

The secondary antibody was goat anti mouse IgG alkaline phosphatase conjugate (Jackson Immunoresearch Cat #115-055-164).

Peptide at 1 mg/ml in PBS.

ELISA Method.

With materials prepared as described above, ELISA screening of monoclonal antibodies produced as described herein was carried out to isolate and provide a monoclonal antibody of the present invention as follows:

1. Coat plates with 50 µl/well of peptide in coating buffer at concentration of 5 µg/ml at 4° C. overnight.
2. Wash plates with 0.05% Tween.
3. Block plates with 200 µl/well blocking buffer overnight at 4° C.
4. Repeat step 2.
5. Add primary antibody (test antibody) at 40 µl/well (Supernatants) or 50 µl/well (serum dilutions) and incubate for 1 hour at room temperature.
6. Wash plates with 0.05% Tween in PBS.
7. Add 50 µl/well of secondary antibody at 1:2000 dilution and incubate at room temperature for 1 hour.
8. Wash plates with 0.05% Tween in PBS.
9. Add 50 µl/well of DEA developer and allow to incubate.
10. Read in spectrophotometer at 405 nm.

A mouse monoclonal antibody produced according to the protocols set forth herein is described in Maile et al. ("A monoclonal antibody against αVβ3 integrin inhibits development of atherosclerotic lesions in diabetic pigs" *Science Translational Medicine* 2(18):18ra11 (2010)) and in U.S. Pat. Nos. 7,723,483; 8,187,595; and 8,206,706.

EXAMPLE 5

Preparation of Humanized Monoclonal Antibody that Binds to the C-Loop of αVβ3 Integrins Objectives.

The objective was to generate humanized antibodies from the murine monoclonal antibody produced according to Example 4 using Composite Human Antibody™ technology. This report details work performed in which the heavy and light chain V region (VH and Vκ) sequences of the HLMC antibody have been determined and Composite Human Antibodies™ have been produced. Segments of human V region sequence were sourced from unrelated human antibody sequence databases. Each selected sequence segment, as well as the junctions between segments were tested for the potential to bind to MHC class II using iTope™ analysis, and all final Composite Human Antibody™ sequence variants were designed to avoid T cell epitopes. Composite Human Antibody™ V region genes were generated using synthetic oligonucleotides encoding combinations of the human sequence segments. These were then cloned into vectors containing human constant regions, and antibodies were produced and tested for binding to target antigen by fluorescence activated cell sorting (FACS) analysis in comparison to the corresponding chimeric antibody with matched human constant regions.

Design of Composite Human Antibody™ Variable Region Sequences.

Structural models of the murine HLMC antibody V regions were produced using Swiss Protein Database (PDB) and analyzed in order to identify important "constraining" amino acids in the V regions that were likely to be essential for the binding properties of the antibody. Residues contained within the CDRs (using both Kabat and Chothia definitions) together with a number of framework residues were considered to be important.

From the above analysis, it was considered that composite human sequences of HLMC could be created with a wide latitude of alternatives outside of CDRs but with only a narrow menu of possible alternative residues within the CDR sequences. Preliminary analysis indicated that corresponding sequence segments from several human antibodies could be combined to create CDRs similar or identical to those in the murine sequences. For regions outside of and flanking the CDRs, human sequence segments representing a wide selection were identified as possible components of the novel Composite Human Antibody™ variable regions.

Design of Variants.

Based upon the above analysis, a large preliminary set of sequence segments that could be used to create HLMC Composite Human Antibody variants was selected and analyzed using iTope™ technology for in silico analysis of peptide binding to human MHC class II alleles, and using the T cell epitope database' (TCED™) of known antibody sequence-related T cell epitopes. Sequence segments that were identified as significant non-human germline binders to human MHC class II, or that scored significant hits against the TCED™ were discarded. This resulted in a reduced set of segments, and combinations of these were again analyzed, as above, to ensure that the junctions between segments did not contain potential T cell epitopes. Selected segments were then combined to produce heavy and light chain variable region sequences for synthesis. For HLMC, five heavy chains and three light chains were constructed with sequences as set forth in the Sequence Listing.

Construction, Expression and Purification of Variant Antibodies.

All variant Composite Human Antibody VH and Vә region genes for HLMC were synthesized using a series of overlapping oligonucleotides that were annealed, ligated and polymerase chain reaction (PCR) amplified to give full length synthetic V regions. The assembled variants were then cloned directly into a pANT expression vector system for IgG1 heavy chains and kappa light chains.

All combinations of composite IgG1 heavy and light chains (i.e., a total of 15 pairings) were stably transfected into NS0 cells via electroporation and selected using 200 nM methotrexate (MTX) (Sigma Cat. No. M8407). MTX resistant colonies for each construct were tested for IgG expression levels using IgG1 ELISA and the best expressing lines were selected and frozen under liquid nitrogen. Successful transfection and clone selection were achieved for all variants although, due to slow growth, two variants, VH1/Vκ1 and VH4/Vκ2, were not taken to the protein purification stage in this study.

Thirteen IgG1 variants for HLMC were purified from NS0 cell culture supernatants on a Protein A sepharose column (GE Healthcare Cat. No. 110034-93) and quantified by $OD_{280\ nm}$ using an extinction coefficient, c (absorbance of a 1 mg/ml solution of protein) (0.1%)=1.61, calculated based on the amino acid sequence. There was a wide range of antibody concentrations in the cell culture supernatants of the different variants and accordingly yields of purified antibody varied widely, from between 0.2 mg-7 mg. A small sample of each antibody variant was analyzed by reducing SDS-PAGE. Bands corresponding to the predicted sizes of the heavy and light chains were observed with no evidence of significant contamination in any lane although a small proportion of additional higher molecular weight band was observed in some variants.

Binding of the Variant Antibodies to RD Cells Expressing alphaVbeta3 Integrin.

The binding of NS0-derived HLMC Composite Human Antibody™ variants to rhabdomyosarcoma (RD) cells expressing alphaVbeta3 integrin was assessed in a flow cytometry binding assay. Briefly, a subconfluent monolayer of RD cells was prepared and incubated in serum free medium for 24 hours prior to harvest. Cells were harvested, washed in cold PBS, resuspended in cell dissociation buffer (Invitrogen Cat. No. 13151-014) and counted using a hemocytometer. Cells were resuspended into a suitable volume of cold FACS buffer (1% FBS/0.01% sodium azide/PBS) to yield a final cell density of $4 \times 10^6$ cells/ml.

A dilution series of each HLMC variant antibody (20 μg/ml-2.5 μg/ml) was prepared and dispensed into a V-bottomed 96 well plate (Corning Cat. No. 3894) at 50 μl/well. 50 μl of cell suspension was added to each well to give a final concentration range of 10 μg/ml-1.25 μg/ml. The plates were incubated at 4° C. for 1 hour. Cells were washed with FACS buffer, resuspended in 100 μl of secondary antibody (Sigma Cat. No. P8047, goat anti-human IgG (γ chain specific; PE conjugated) and incubated for 1 hour at 4° C. Cells were washed twice, resuspended in a final volume of 175 μl FACS buffer and transferred to FACS tubes. Fluorescence was measured by flow cytometry and data plotted as normalized % positive events (gated in R2).

Figure 1B:
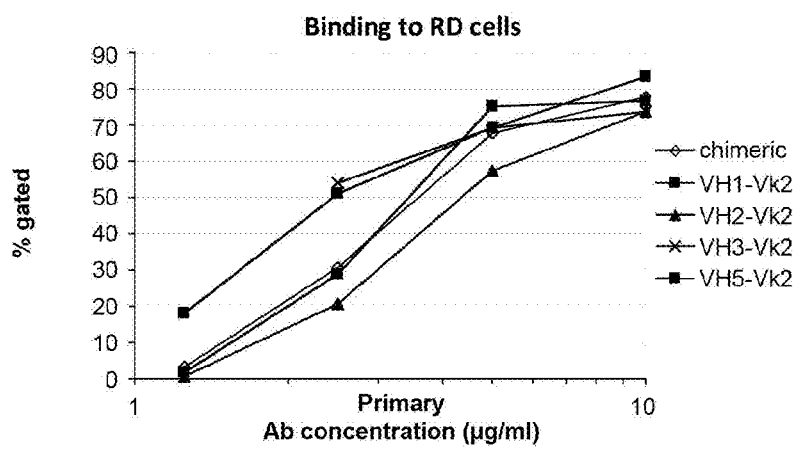
Figure 1C:
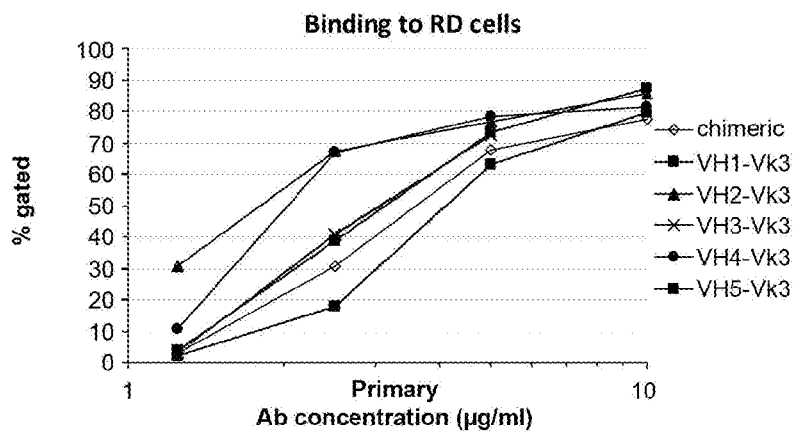

The NS0-derived Composite Human Antibody™ variants had very similar binding profiles to the chimeric (human constant region and mouse variable region) HLMC mAb (FIG. 1). $EC_{50}$ (effective concentration where 50% of cells were gated in R2) values of all 13 variants are shown in Table 1. Relative binding scores for humanized variants were calculated by dividing the $EC_{50}$ of each variant by the $EC_{50}$ of chimeric antibody and these scores are shown in Table 2.

Conclusions.

Composite Human Antibodies™ specific for the heparin binding loop of alphaV beta3 integrin have been constructed from amino acid sequence segments derived entirely from unrelated human antibody variable regions. All CDR and framework regions in the Composite Human Antibody™ variants comprised more than one unrelated human sequence segment (sourced from the human sequence databases), and all Composite Human Antibodies™ were designed specifically to avoid T cell epitopes.

Thirteen candidates were purified and tested and were demonstrated to have, on average, binding within two-fold of the chimeric HLMC. Based on the binding data of the Composite Human Antibodies™, the following antibodies were suggested as lead candidates for further analysis: VH4/Vκ1, VH5/Vκ2, VH3/Vκ3, VH4/Vκ3 and VH5/Vκ3.

EXAMPLE 6

Testing the Monoclonal Antibody for Immunogenicity

Summary.

The objective was to assess the immunogenic potential of fully humanized anti-alphaV/beta3 integrin c-loop antibodies compared to a reference chimeric antibody. Humanized antibodies were generated as described in Example 5. Candidate composite heavy and light chain variable regions (V regions) comprised of multiple, fully human sequence segments were tested using in silico tools for potential T cell epitopes using T Cell Epitope Database (TCED™; Antitope, UK) as well as for the ability to bind to MHC class II using iTope™ analysis. All final Composite Human Antibody™ sequence variants were designed to avoid T cell epitopes in V regions. Confirmation of the lack of immunogenicity in the two lead humanized antibodies (Vh5/Vk2 and Vh4/Vk1) was determined by measuring ex vivo T cell responses against the whole antibody proteins (compared to the chimeric antibody) using the EpiScreen™ time course T cell assay. The results showed that the chimeric antibody has significant immunogenic potential (20% donor response rate), while the fully humanized variants Vh5/Vk2 (5% response rate) and Vh4/Vk1 (0% response rate) have very low potential for immunogenicity. Both humanized variants can therefore be considered to have a low risk of immunogenicity in the clinic.

Introduction.

Immune responses to biological therapeutic agents are wide ranging, and can be directed against agents that are both non-human and human in origin. These responses include those that elicit a weak clinical effect and those that limit efficacy, which can occasionally result in morbidity or even mortality in patients. In particular, serious complications can arise with the production of neutralizing antibodies, especially when they target recombinant self proteins and therefore have the potential to cross react with the patient's own endogenous protein (Lim, 2005). Problems associated with immunogenicity to biologics, especially monoclonal antibodies, have been reduced largely due to advances in molecular biology. There are, however, many recombinant protein biologics that are identical to endogenously expressed human sequences that still elicit potent neutralizing immune responses in patients (Hochuli 1997, Schellekens et at 1997, Namaka et at 2006).

The mechanism by which immunogenicity is triggered remains unclear although the tolerance to self proteins may be broken by a number of factors linked to both the product and the patient (reviewed in Chester et al 2005, Baker and Jones 2007). For the product, these include dose, frequency of administration, route, immunomodulatory capacity of the protein therapeutic, and the formulation (Jaber and Baker 2007). For the patient, factors such as immune competence (i.e., whether the patient is receiving immunosuppressive treatment), a patient's major histocompatibility (MHC) haplotype and intrinsic tolerance to the protein therapeutic will influence immunogenicity. Regardless of how immunogenicity is triggered, one of the single most important factors in the development of an ensuing immune response is the presence of epitopes that are able to effectively stimulate a potent $CD4^+$ T cell response.

A pre-clinical ex vivo T cell assay (EpiScreen™) has been developed, which provides an effective technology for evaluating T cell immunogenicity by quantifying T cell responses to protein therapeutics. EpiScreen™ time course T cell assays provide a format in which the immunogenicity of whole proteins can be assessed. Using a cohort of community blood donors carefully selected based on MHC haplotypes, purified therapeutic proteins are tested for T cell immunogenicity in vitro. This technology has been used successfully to compare protein variants for the potential to induce an immune response in vivo (Jones et at 2004, Jones et at 2005). These studies show that the EpiScreen™ assay provides an ideal screening technology due to the high degree of sensitivity along with the robust nature of the assay which allows an accurate pre-clinical assessment of the potential for immunogenicity of biologics.

In the present study, three antibodies were assessed for immunogenic potential using EpiScreen™ time course T cell assays. The antibodies tested were a chimeric antibody (HMLC) and two fully-humanized antibodies generated using Composite Human Antibody™ technology, Vh5/Vκ2 and Vh4/Vk1. Bulk cultures were established using CD8+ depleted PBMC, and T cell proliferation as determined by incorporation of [$^3$H]thymidine was measured at various time points after the addition of the samples.

Preparation and Selection of Donor PBMC.

Peripheral blood mononuclear cells (PBMCs) were isolated from healthy community donor buffy coats (from blood drawn within 24 hours) obtained from the UK National Blood Transfusion Service (Addenbrooke's Hospital, Cambridge, UK) and according to approval granted by Addenbrooke's Hospital Local Research Ethics Committee. PBMC were isolated from buffy coats by Lymphoprep (Axis-shield, Dundee, UK) density centrifugation and CD8+ T cells were depleted using CD8+ RosetteSep™ (StemCell Technologies Inc, London, UK). Donors were characterized by identifying HLA-DR haplotypes using an HLA SSP-PCR based tissue-typing kit (Biotest, Solihull, UK). T cell responses to a control antigen (Keyhole Limpet Hemocyanin (KLH), Pierce (Perbio), Northumberland, UK) as well as to control peptides derived from Influenza A and Epstein Barr viruses were also determined. PBMCs were then frozen and stored in liquid nitrogen until required.

A cohort of 20 donors was selected (study cohort VSC01) to best represent the number and frequency of HLA-DR allotypes expressed in the world population. Analysis of the allotypes expressed in the cohort against those expressed in the world population revealed that all major HLA-DR alleles (individual allotypes with a frequency >5% expressed in the world population) were well represented. Four donors responded positively to one or more antibodies.

Purification of Antibodies.

Humanized antibodies Vh5/Vk2 and Vh4/Vk1 were prepared for EpiScreen™ analysis. Chimeric antibody was prepared from a 1 L culture of antibody expressing NS0 cell-line grown to saturation. Supernatants were separated from cells and debris by centrifugation, adjusted to pH 7.4, filter sterilized and run through 1 ml Hi-Trap Mab Select Sure protein A affinity columns (GE Healthcare, Amersham, UK), which had previously been sanitized with 0.5M NaOH and equilibrated into PBS, at a flow rate of 1 ml/min. The columns were washed with 20 ml PBS pH 7.4. Antibody was eluted in 1 ml fractions with 0.1M sodium citrate pH 3.0 and each fraction immediately neutralized with 0.1 ml 1M Tris-HCl. The protein content of each fraction was monitored by UV absorption at 280 nm and protein containing fractions were pooled. The antibody was further purified by size exclusion chromatography using a 16/60 Superdex 5200 column (GE Healthcare, Amersham, UK). The major peak fractions were collected, pooled and buffer exchanged into 200 mM phosphate buffer pH7.0. Purified antibody was then filter sterilized and stored at +4° C. Final concentrations were determined by UV absorption using calculated molar extinction coefficients where A280 1.0=1.51 mg/ml.

Samples from each preparation were compared for purity by overloading silver stained SDS/PAGE. Each of the three test samples was run into a denaturing 4-12% SDS/PAGE gel (Invitrogen, Paisley, UK) alongside molecular weight markers. Gels were then stained for protein using a Deep Silver stain kit (MoBiTec, Gottingen, The Netherlands). Antibody heavy chain (approximately 55 kDa) and light chain (approximately 26 kDa) were detectable for all three preparations and all preparations were highly pure. Endotoxin analysis of all three preparations using an Endosafe®-PTS™ assay (Charles River, Margate, UK) showed endotoxin to be below the limit of detection for this assay (i.e., >0.5 Eu/ml) and within the tolerances of the EpiScreen assay.

Preparation of Samples.

Test samples (chimeric: 0.69 mg/mL; Vh5/Vκ2: 2.05 mg/mL; VH4/Vκ1: 0.506 mg/mL) were prepared and stored at +4° C. Samples were diluted in AIM-VR culture medium (Invitrogen, Paisley, UK) and the final assay concentration was 50 μg/ml. KLH was used as a reproducibility control and stored at −20° C. as a 10 mg/ml stock solution in water. For the studies, an aliquot of KLH was thawed immediately before diluting to 400 μg/ml in AIM-VR (final concentration 100 μg/ml).

EpiScreen™ Time Course T Cell Proliferation Assays.

PBMCs from each donor were thawed, counted and viability assessed. Cells were revived in room temperature AIM-VR culture medium, washed and resuspended in AIM-VR to 4-6×10$^6$ PBMC/ml. For each donor, bulk cultures were established in which 1 ml proliferation cell stock was added to the appropriate wells of a 24 well plate. Culture medium (0.5 ml) and 0.5 ml of each diluted test sample were added to the PBMCs to give a final concentration of 50 μg/ml per sample. For each donor, a reproducibility control (cells incubated with 100 μg/ml KLH), and a culture medium only well were also included. Cultures were incubated for a total of 8 days at 37° C. with 5% $CO_2$. On days 5, 6, 7 and 8, the cells in each well were gently resuspended and 3×100 μl aliquots transferred to each well of a round bottomed 96 well plate. The cultures were pulsed with 0.75 μCi [$^3$H]thymidine (PerkinElmer, Buckinghamshire, UK) in 100 μl AIM-VR culture medium and incubated for a further 18 hours before harvesting onto filter mats (Perkin Elmer) using a TomTec Mach III cell harvester. Counts per minute (cpm) for each well were determined by Meltilex™ (Perkin Elmer®) scintillation counting on a 1450 MicrobetaWallac-Trilux Liquid Scintillation Counter (Perkin Elmer®) in paralux, low background counting.

EpiScreen™ Data Analysis.

For proliferation assays, an empirical threshold of a stimulation index (SI) equal to or greater than 2 (SI≥2.0) has been previously established whereby samples inducing proliferative responses above this threshold are deemed positive (where included, borderline SIs≥1.90 are highlighted). Extensive assay development and previous studies have shown that this is the minimum signal to noise threshold allowing maximum sensitivity without detecting large numbers of false positive responses. For proliferation data sets (n=3), positive responses were defined by statistical and empirical thresholds:

1. Significance (p<0.05) of the response by comparing cpm of test wells against medium control wells using unpaired two sample student's t-test.
2. SI equal to or greater than 2 (SI≥2.0). In addition, intra-assay variation was assessed by calculating the CVs and SDs of the raw data from replicate cultures.

Results.

The three antibodies were tested against a cohort of 20 healthy donors using EpiScreen™ time course T cell assay in order to determine the relative risk of immunogenicity. The samples were tested at a final concentration of 50 μg/mL based on previous studies showing that this saturating concentration is sufficient to stimulate detectable antibody-specific T cell responses.

In order to assess the immunogenic potential of each sample, the EpiScreen™ time course T cell assay was used with analysis of proliferation to measure T cell activation. Since the samples had not been previously assessed in a PBMC-based assay, an initial assessment of any gross toxic effect of the samples on PBMC viability was determined. Cell viabilities were calculated using trypan blue dye exclusion of PBMC 7 days after culture with the test samples. It was clear that the test samples did not significantly affect the viability of the cells since PBMC from medium alone cultures had a mean viability similar to that of the test samples and KLH treated cells.

Screening of samples using EpiScreen™ T cell proliferation assay of CD4+ T cell responses induced by the test samples and the positive control, KLH. Two antibodies induced positive responses using a stimulation index (SI) ≥2.0, p<0.05 threshold in at least one donor in the proliferation assay. The overall immunogenic potency of the test samples was determined based on the magnitude (SI) of the response along with the frequency (%) of responding donors in the study cohort. The test samples induced positive proliferation responses in donors ranging from 5% to 20% of the study cohort. The test sample associated with the highest proliferation response was the chimeric antibody, which induced a positive response in 20% of the study cohort (responding donors: 3, 8, 12, and 19). The humanized antibody Vh5/Vk2 stimulated a response in 1 of the 20 donors (5% of the study cohort) and Vh4/Vk1 failed to stimulate any responses in any of the donors. Results with the control antigen KLH show that there was a good correlation between positive and negative results in repeat studies Test 1 and VSC01, which indicates a high level of reproducibility in the assay. In addition, all the basal cpms for the control wells were above the minimum threshold for the assay of 150 cpm. Donors with basal (untreated control) cpm below this threshold are normally excluded from further analysis.

Analysis of the magnitude (SI) of positive T cell proliferation responses using SI≥2.0 shows that the mean magnitude for the chimeric antibody (SI=2.23) was lower than for Vh5/Vk2 (SI=3.25). However, since there was only one positive response against Vh5/Vk2, the immunogenic potential remains very low.

The overall timing of the proliferative responses can provide information as to the potential type of T cell response (naive or recall). Maximal T cell proliferation detected on day 5 indicates that existing T cell precursor frequencies are high whereas maximal proliferation on day 8 indicates a low existing T cell precursor frequency. A high immunogenic potential would be concordant with stimulation of T cells during the early phase of the time course. The number of positive proliferation responses occurring against the samples on each day of the four point time course was summarized using a threshold of SI≥2.0, p<0.05. The results show that T cell responses specific for the chimeric antibody occurred mostly on day 8, and the only positive T cell response to Vh5/Vk2 also occurred on that day, suggesting that existing T cell precursor frequencies were low.

Interpretation of Results.

The proliferation data show that four positive proliferation responses from 20 donors (20%) were detected against the chimeric antibody compared to only one donor response against the fully humanized Vh5/Vk2 antibody (5%) and no responses were detected against the fully humanized Vh4/Vk1 antibody. Table 3 shows a summary of positive proliferation responses against the test antibodies in the T cell time course proliferation assay. Analysis of the dataset from this assay revealed that the ranking of potential for immunogenicity in the clinic is (from highest to lowest); chimeric antibody>Vh5/Vk2≥Vh4/Vk1. An analysis of the positively responding donor haplotypes was performed to evaluate any association between MHC class II allotype and responses to a particular antibody. This was considered possible if the frequency of the allotype within the responding population was double the frequency observed in the study cohort. This analysis was restricted to samples that produced a response in >5% of donors. There were no HLA associations observed in the T cell responses against the chimeric antibody, which was the only test sample to fulfill the criteria of a positive proliferative response in >5% of donors.

Studies were conducted to demonstrate a correlation between the level of immunogenicity observed using the EpiScreen™ assay and the level of immunogenicity (anti-protein therapeutic antibody responses) that has been actually observed in the clinic against a large panel of therapeutic proteins (Baker and Jones, 2007). High levels of immunogenicity were observed in both the clinical data and EpiScreen™ assays for proteins such as Infliximab and Campath, whereas relatively low levels of immunogenicity were observed for proteins such as Xolair, Herceptin, and Avastin. Importantly, the fully humanized Vh5/Vk2 and Vh4/Vk1 antibodies induced responses in <10% of the study cohort which, based on previous experience, is associated with therapeutic proteins with a low risk of clinical immunogenicity. Therefore both the fully humanized Vh5/Vk2 and Vh4/Vk1 antibodies can be considered as clinical candidates with low risk of immunogenicity.

Conclusions.

The EpiScreen™ time course T cell proliferation assay was used to determine the relative potential for clinical immunogenicity of one chimeric and two fully humanized antibodies. The antibodies were compared for their ability to induce CD4$^+$ T cell responses as measured by proliferation against a panel of 20 HLA-typed donors. Positive CD4$^+$ T cell proliferation responses were observed in the EpiScreen™ time course T cell assay against the chimeric antibody and were in the expected range of 15-40%. Frequent and potent T cell responses were observed against the control antigen, KLH, which indicate that the assay functioned as expected. The results show that the chimeric antibody had a significant immunogenic potential (20% response rate), while the fully humanized variants Vh5/Vk2 (5% response rate) and Vh4/Vk1 (0% response rate) have very low immunogenicity potential. Both humanized variants can therefore be considered to have a low risk of immunogenicity in the clinic. Associations between MHC class II allotype and positive responses to the test antibodies were also investigated; however no associations were found.

Previous EpiScreen™ time course T cell assays with a range of biologics have shown a clear correlation between the percentage of donor T cell responses in the EpiScreen™ assay and the level of immunogenicity (anti-protein therapeutic antibody responses) observed in the clinic. High frequency donor responses were observed in EpiScreen™ assays for immunogenic antibodies such as Campath, whereas relatively low frequency donor responses were observed for non-immunogenic antibodies such as Xolair and Herceptin. In general, protein therapeutics that induce <10% positive responses in the EpiScreen™ assay are associated with a low risk of immunogenicity in the clinic. The current study shows that, by comparison to other protein therapeutics tested in EpiScreen™ assays, the data from this study show that Vh5/Vk2 and Vh4/Vk1 fall into the same range as Xolair, Herceptin and Avastin, and would be considered as having a low potential risk of immunogenicity. By comparison the chimeric antibody stimulated 20% of donors to respond in the EpiScreen™ assay and would fall into the same range as more immunogenic antibodies such as Humira and MLN02. Therefore, it was concluded that fully humanized antibodies analyzed in this study exhibit a clinically acceptable profile in the EpiScreen™ immunogenicity assay providing confirmation of reduced immunogenicity as a result of humanization.

EXAMPLE 7

Methods for Testing VPI-2690B Antibody

The purified antibody identified in Example 6 as having reduced immunogenicity, VPI-2690B, which includes the heavy chain variable region VH6 (SEQ ID NO:12) and the light chain variable region Vκ2 (SEQ ID NO:14), was analyzed in several biological test systems and is the antibody described throughout the Examples provided herein. Initially the material was tested using cultured porcine vascular smooth muscle cells and human umbilical vein endothelial cells. Porcine smooth muscle cells or human umbilical vein endothelial cells were seeded at a density of $1 \times 10^5$ cells/well in six well culture plates in DMEM-H (high glucose) with 10% FBS and incubated for 2 to 3 days. The cells were then serum starved overnight in serum free DMEM-H. The medium was then changed to DMEM-H with antibody treatments and incubated for an additional four hours at 37° C. The antibody was tested over a concentration range from 5 ng/ml to 1000 ng/ml and compared with VH5/VK2 antibody. The cells were then directly stimulated with IGF-1 (50 ng/ml) for 5 to 10 min. The cells were then lysed in 300 μL of RIPA. 40 μL of the resulting lysate was loaded onto an SDS 8% polyacrylamide gel and the proteins were separated and then transferred to a poly vinyl difluoride (PVDF) membrane to be immunoblotted for phosphorylated MAP kinase (ERK), phosphorylated AKT, and total MAP kinase (ERK), AKT and beta 3. The remainder of the lysate was immunoprecipitated with an anti-beta three antibody (1 to 100 dilution) and following separation on 8% SDS polyacrylamide gel, it was transferred to a PVDF membrane and immunoblotted with an anti-phosphotyrosine antibody.

After immunoblotting, films were prepared and scanned using a scanning densitometer and then arbitrary density scanning units were obtained to calculate the response of phospho MAP, AKT and beta 3 to antibody treatment. Each treatment is compared basally following exposure to hyperglycemia or to hyperglycemia plus antibody and then each is compared following IGF-1 stimulation.

Figure 2A:
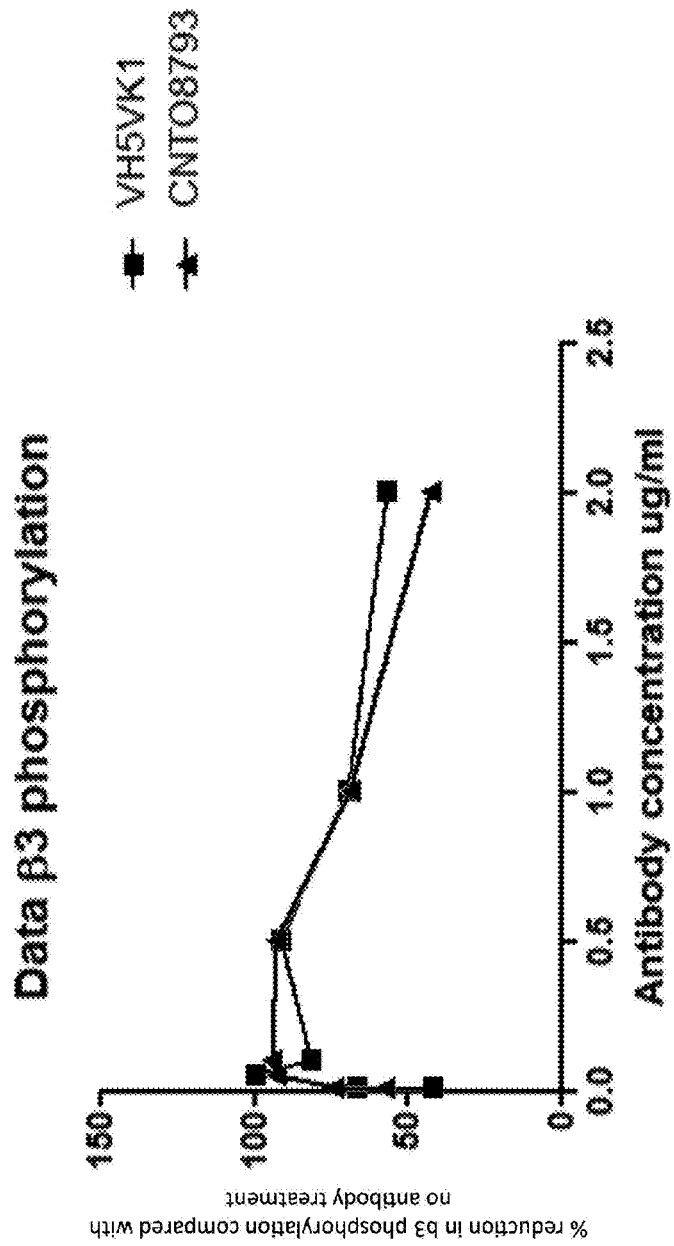
Figure 2B:
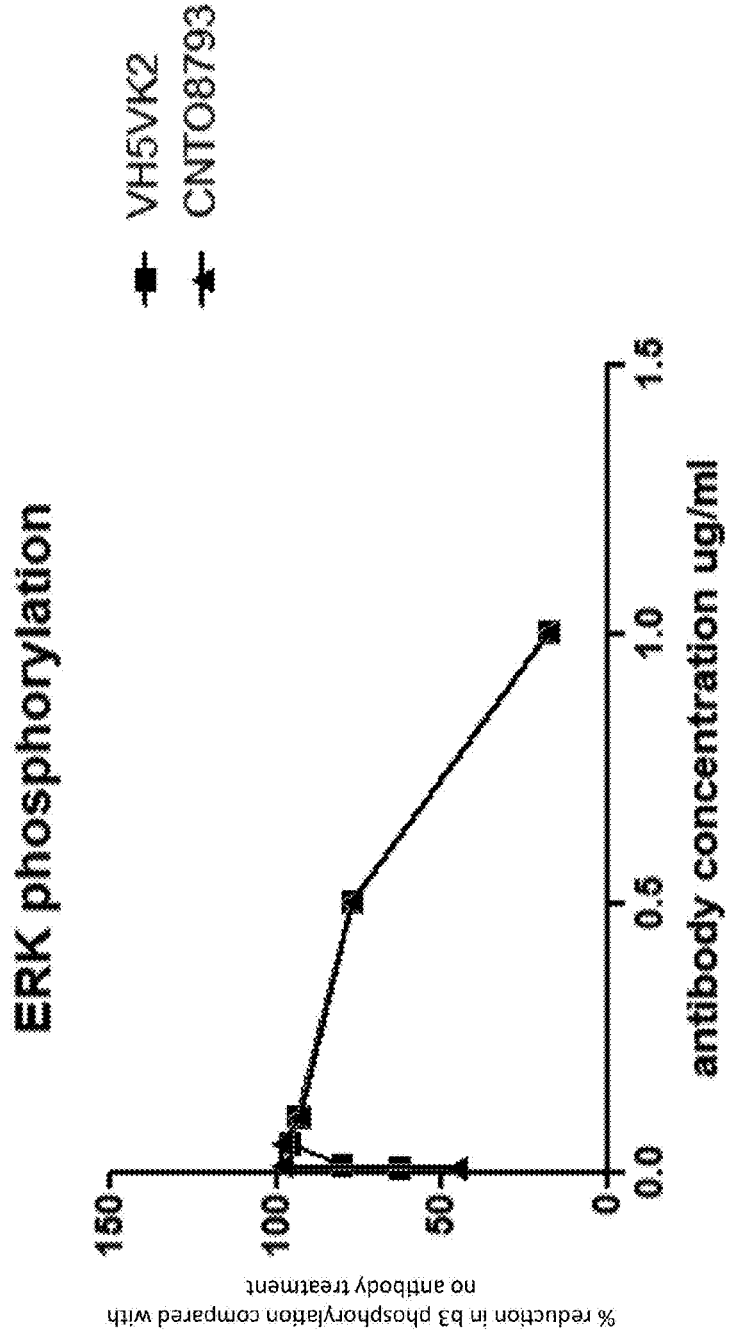
Figure 3A:
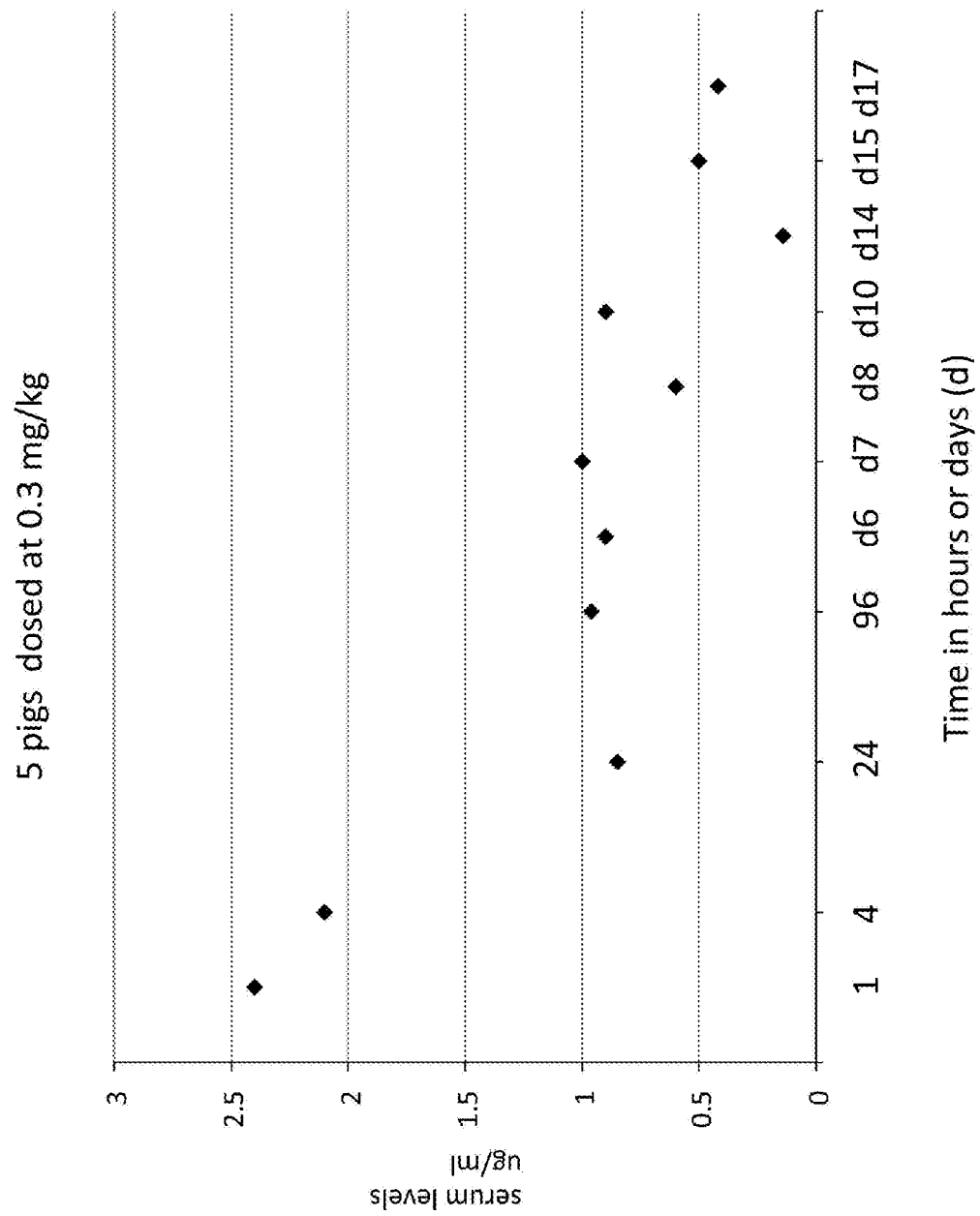
Figure 3B:
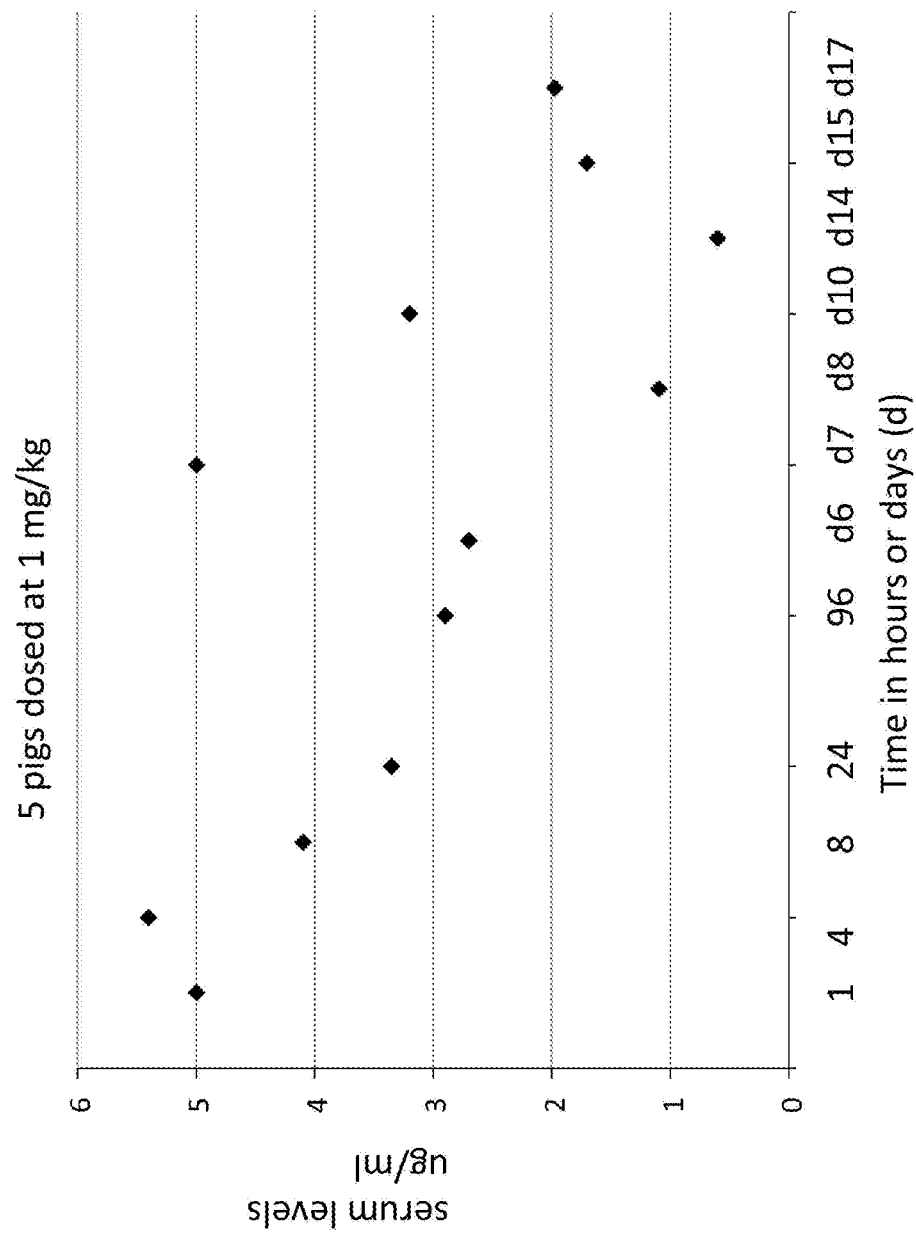
Figure 3C:
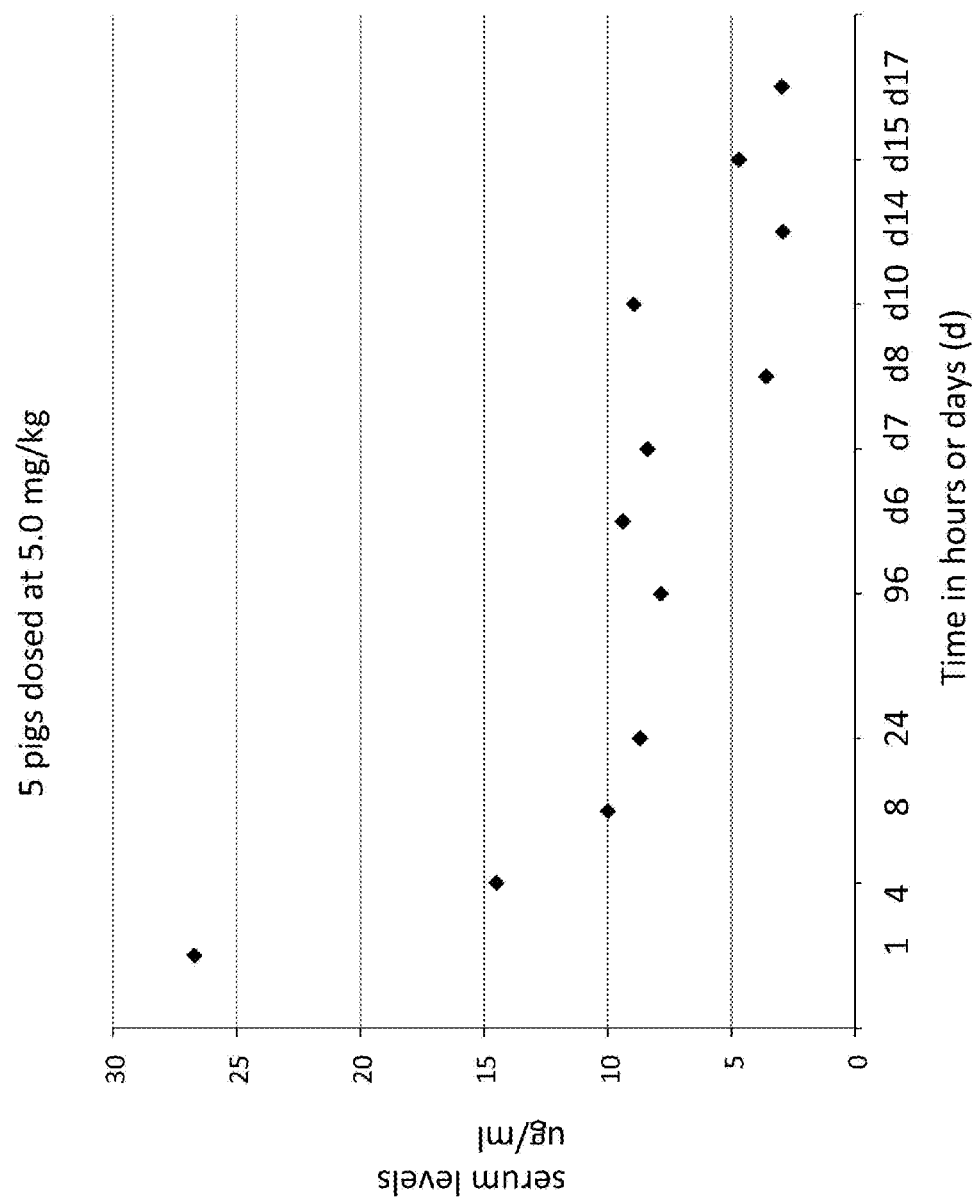

The intensity of the blots that were scanned under basal or IGF-1 stimulatory stimulatory conditions are classified as arbitrary values determined to be zero inhibition. A scan value of zero is assumed equal to 100% inhibition; thus the values for the unknown treatments were calculated as follows (100 minus this scan value of the treatment divided by the scan value of the untreated sample×100=% inhibition). FIG. 2 shows the change in β3 integrin tyrosine phosphorylation (FIG. 2A), AKT serine 473 phosphorylation (FIG. 2B) and MAP kinase (ERK) serine phosphorylation (FIG. 2C).

These data showed that the addition of either antibody between concentrations of 10-500 ng/ml results in inhibition of β3 phosphorylation or IGF-1 stimulated MAP kinase and AKT activation. At concentrations greater than 500 ng/ml, there was a partial reversal of the effect. These results support the conclusion that both forms of the antibody are potent inhibitors of these signaling pathways, which are activated in response to hyperglycemia and IGF-1.

EXAMPLE 8

Testing Pharmacokinetic Profile in Pigs

Normal Yorkshire pigs, average weight 40 kg, were utilized to determine the pharmacokinetic profile of the humanized antibody of this invention. The purified antibody was reconstituted in PBS at a concentration of 50 mg/mL. Three doses were administered to five animals in each dosage group. The antibody was administered subcutaneously. Each animal was anesthetized with ketamine 0.1 mg/kg. After complete anesthesia was achieved one of three dosages was administered. These dosages included 0.3 mg/kg, 1.0 mg/kg and 5.0 mg/kg. Blood was taken at the time intervals shown. Each data point represents determinations from at least two animals. No animal could be bled at all time points due to safety reasons. Following removal of 1 mL of blood it was centrifuged immediately. The serum was removed and the formed elements discarded. Sera were frozen until assay. The ELISA method for determining the drug levels within the serum is as follows. Each well of a 96 well polystyrene microtiter plates is coated over night at 4° C. with a solution of the C-loop antigen conjugated to bovine serum albumin (BSA) in a carbonate/bicarbonate buffer (100 mM; pH 5) at a final concentration of 5 ug/ml. After rinsing the wells with phosphate buffered saline (PBS) each well is then blocked with a solution of 2% BSA in PBS overnight at 4° C. On the day of assay the ELISA assay standards are made by preparing dilutions of a stock solution of VPI-2690B antibody to achieve final concentrations ranging from 1.9 ng/ml to 1.000 ng/ml in ELISA buffer. Serum samples to be tested are diluted 1:20, 1:40 and 1:100 in ELISA buffer. The coated/blocked ELISA plate is rinsed with PBS and the wells filled with 50 ul of standards or samples (each in duplicate). The assay plate was rocked at room temperature for 1 hour. Wells were then washed with PBS+0.1% Tween 20 (3 times in total) and then 100 ul of the alkaline phosphatase labeled anti-human secondary antibody (diluted 1:2000 in ELISA buffer) was added to each well. The plate was again rocked at room temperature for 1 hour. Meanwhile the detection reagent was prepared by dissolving a p-Nitrophenyl Phosphate (Disodium Salt) in a 5M solution of Diethanolamine. The wells were rinsed again with PBS and then 50 ul of detection reagent was added to each well. The color change was allowed to develop and then measured in a microtiter plate reader at 405 nm. The absorbance values for the standard curve samples were plotted against protein concentration and used to calculate the amount of protein in the unknown samples.

FIGS. 3A-D show that there was a dose-dependent increase in the peak blood concentration for each dosage administered. The results show that the half-life of the drug is between seven and 10 days. The half-life was not dosage dependent however the absolute concentrations at the end of the half-life did reflect the initial dosage. It is concluded that the drug is well absorbed from the subcutaneous space and that the serum concentrations reflect the distribution of the drug that would be predicted from an animal of this size and weight and that the half-life will allow at least weekly administration.

EXAMPLE 9

The aim of this study was to characterize the pharmacokinetic-pharmacodynamic (PK/PD) relationship of VPI-2690B by determining the dose response relationship in a pharmacodynamic assay that measures the ability of VPI-2690B to inhibit the αVβ3 biochemical signal transduction pathway in a rodent model of type 1 diabetes (streptozotocin [STZ]-induced diabetes in Sprague Dawley rats). A secondary objective was to determine whether pharmacological efficacy using a renal endpoint could be measured in newly diabetic animals.

All rats were fasted for 4 hours and then given a single intraperitoneal (IP) injection of STZ (50 mg/kg) in vehicle. Sodium citrate and STZ were prepared fresh immediately before injection. Hyperglycemia was confirmed 5 days later using tail vein blood and a Free Style lite glucose meter.

One week after confirmation of hyperglycemia, rats were randomly divided into 1 of 7 groups (0, 0.01, 0.03, 0.1, 0.3, 0.5 or 1 mg/mL VPI-2690B) with 4 rats/group. Rats were then injected (subcutaneously [SC]) with the appropriate dose of VPI-2690B. One week later, the injection of VPI-2690B was repeated.

One week after the second injection, rats were euthanized using pentobarbital (SC; 80 mg/kg). Once under anesthesia, the abdomen was opened and urine collected by syringe from the bladder. The thorax was then opened and the heart nicked, blood was collected and the rat perfused with PBS via an injection into the heart. The kidneys were removed and dissected free of peri-nephretic fat and flash frozen in liquid nitrogen before being stored at −80° C. for future analysis. Urine was centrifuged (13,000 revolutions per minute [RPM] for 15 minutes at 4° C.) and supernatant frozen at −20° C. until later analysis.

Blood was left to clot and then centrifuged (13,000 RPM for 15 minutes at 4° C.) and the resulting serum removed and stored at −20° C. for later analysis.

At a later time point, a section of flash frozen kidney was homogenized in radioimmunoprecipitation assay buffer (RIPA). The homogenates were centrifuged 13,000×g for 10 minutes to clear debris.

Equal amounts of kidney homogenate (2 mg/sample) were immunoprecipitated with an anti-β3 antibody using a 1:500 dilution (R2949). The proteins in the immunoprecipitate were separated by sodium dodecyl sulfate-polyacrylamide gel electrophoresis (SDS-PAGE). After transfer to Immobilon P, it was immunoblotted with anti-phosphotyrosine antibody at a 1:1500 dilution. Protein concentrations in all lysates were assessed using the Bicinchoninic Acid Assay (BCA) kit from Pierce Protein Biology Products.

The films were digitized by scanning at 300 dpi on a DuoScan (Agfa). The scans of individual gels were converted to tif files in Photoshop. The tif files were analyzed with ImageJ using the Gel Analyzer Tool in ImageJ. This tool reports the results in arbitrary units.

NephratII was used to measure urine albumin in rats. This assay is a competitive binding assay; sample and anti-rat albumin antibody-HRP conjugate are added to an albumin-coated well. The antibody binds to the albumin immobilized onto the stationary phase or to the albumin in the fluid phase, hence the notion of competitive binding. After washing, only the antibody-conjugate that has bound to the albumin of the stationary phase will remain in the well. Color intensity in Nephrat is inversely proportional to the logarithm of albumin concentration in the fluid phase.

Urinary creatinine was measured using an Automatic Chemical Analyzer.

96-well immulon plates were coated with 100 μl/well of peptide in coating buffer at concentration of 5 μg/mL at 4° C. overnight (18-20 hours) with rocking Plates were then washed with 0.05% Tween PBS (200 μL/well×3 washes), then blocked with 200 μL/well blocking buffer at 4° C. overnight (18-20 hours) with rocking Plates were again washed with 0.05% Tween PBS (200 μL/well×3 washes).

Standards, controls, and samples (50 μl/well) were added and incubated for 1 hour at room temperature with rocking, and plates were washed with 0.05% Tween PBS (200 μl/well×3 washes). Next, 100 μL/well of HRP labeled secondary antibody 1:200,000 was added and incubated for 1 hour at room temperature with rocking, and then the plates were washed with 0.05% Tween PBS (200 μl/well×3 washes).

Next, 100 μL/well of TMB substrate was added and color was allowed to develop 20 minutes with shaking at room temperature. 100 μL/well of 2M sulfuric acid was then added to stop the reaction.

Finally, plates were shaken for 5 seconds and read in a spectrometer at 450 nm.

The data analyses were run in GraphPad Prism® or in Microsoft Excel® software. Averages and standard errors were calculated in GraphPad Prism® or in Microsoft Excel® software (using the Descriptive Statistics in the Data Analysis tool).

Mean body weight and glucose level data for study animals by treatment group at the start and end of the study are presented in Table 5. There were no meaningful differences between the 7 different groups, and VPI-2690B had no effect on either body weight or glucose levels in this study.

Figure 4:
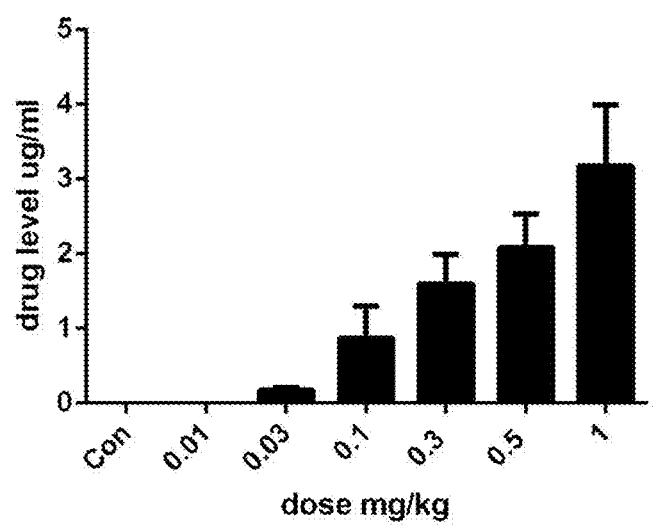
FIG. 4. Mean (±SEM) Levels of VPI-2690B Measured in Serum 7 days after the second injection at time of necropsy by Treatment Group.

Mean levels of VPI-2690B measured in serum on Day 8 and on Day 15 (at the time of necropsy, 7 days after the second injection) are presented in Table 6. In general, the animals had similar or higher levels of VPI-2690B at Day 15 compared to Day 8. The dose-concentration curve at necropsy is shown in FIG. 4. A dose-dependent increase in serum drug levels was observed.

Figure 5:
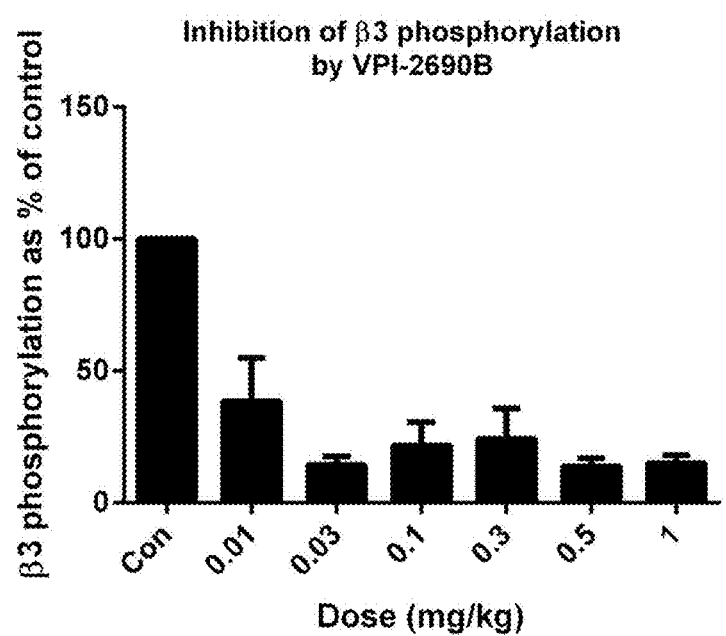
FIG. 5. Mean (±SEM) β3 Phosphorylation (Presented as Percent of Control) in Kidney Lysates by Treatment Group.

Mean β3 phosphorylation measured in kidney lysates at the end of treatment is shown in Table 7 and presented graphically in FIG. 5. There was a dose dependent decrease in β3 phosphorylation in the kidneys of animals treated with VPI-2690B compared with control (untreated) animals. There was no evidence of a reversing dose response, as was seen in vitro. A dose of 0.03 mg/kg VPI-2690B appears to be maximally active in this in vivo pharmacodynamic assay.

In order to define the PK/PD relationship and understand the parameters of target engagement for VPI-2690B, the current study examines the phosphorylation state of β3 integrin (a biochemical measure of activation of the αVβ3 pathway), which is the molecular target of the antibody, in the target organ, the kidney. Because the relevant physiological endpoints of improvements in renal function require chronic treatment with VPI-2690B, the pharmacodynamic readout was performed at necropsy, after 14 days of exposure to drug. Therefore, β3 phosphorylation is not a circulating measure of acute target engagement, but rather is a measure of chronic target engagement in the target organ.

Figure 6:
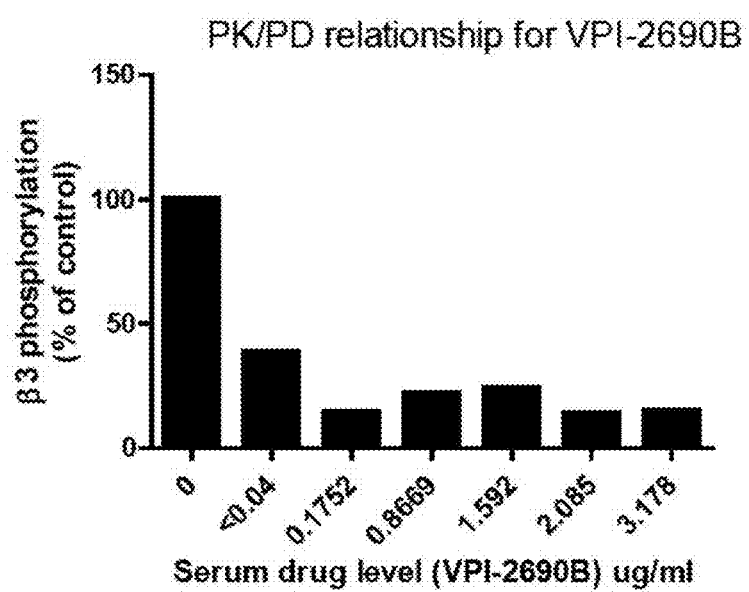
FIG. 6. PK/PD relationship for VPI-2690B.

Fourteen days was chosen as the optimal time to define the PK/PD relationship. The trough circulating drug levels, measured at the end of the study, the same time that the PD measurement was taken, thus can be used to define the relevant PK/PD relationship for target engagement and biochemical activity of the antibody in vivo (FIG. 6). As indicated above, a dose of 0.03 mg/kg VPI-2690B achieved maximal inhibition in this in vivo pharmacodynamic assay. This dose corresponded to circulating drug level of 0.175 µg/mL at the same time point. VPI-2690B was partially active in this PD assay at a dose of 0.01 mg/kg, which corresponded to a drug level <0.04 µg/mL (the LLOQ for the assay).

Figure 7:
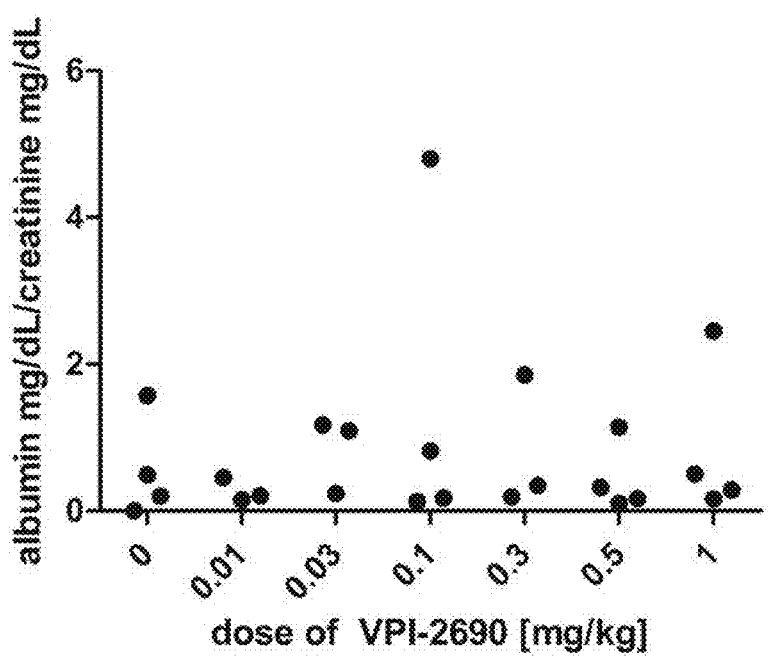
FIG. 7. Albuminuria in Individual Study Animals at necropsy by Treatment Group.

Levels of urinary albumin measured in individual animals as the ratio of albumin (mg/dL)/creatinine (mg/dL) at the end of the study are presented in FIG. 7. There were no consistent differences between groups observed. Previous efficacy studies in this model with albuminuria as an end point have been performed after 4-20 weeks of diabetes. The current study was shortened to 3 weeks to avoid the development of anti-drug antibodies, which have been observed in the rat after 3 or more weekly doses of VPI-2690B and have the potential to confound the PK/PD analysis. It appears that 3 weeks of diabetes was insufficient to see a significant increase in proteinuria; and therefore the impact of VPI-2690B treatment on this parameter could not be assessed in this study.

The PK/PD relationship of VPI-2690B was determined in the rat, using the phosphorylation state of β3 integrin, which is the molecular target of the antibody, in the target organ, the kidney, as the PD endpoint. Because the relevant physiological endpoints of improvements in renal function require chronic treatment with VPI-2690B, the PK/PD relationship was determined after chronic (14 days) dosing, with both the drug levels and the β3 phosphorylation being measured 7 days after the last injection. VPI-2690B exhibited full PD activity when administered to rats at a dose of 0.03 mg/kg, corresponding to a drug level of 0.175 µg/mL. VPI-2690B was partially active in this PD assay at a dose of 0.01 mg/kg, which corresponded to a drug level <0.04 µg/mL (the LLOQ for the assay). The PD dose-response curve was monophasic, reaching a plateau at high doses, and did not return to baseline even at very high concentrations of the drug. Thus, circulating concentrations of VPI-2690B of ~0.2 mg/mL would be expected to be associated with pharmacodynamic activity of the drug in vivo, corresponding to biochemical inhibition of the target αVβ3 signaling pathway in the kidney.

EXAMPLE 10

The objectives of this study were to characterize the binding affinity of VPI-2690B to a) determine the binding affinity of VPI-2690B at different stages of development against peptide antigen (human, monkey, rat and mouse comparison); b) determine the binding affinity of VPI-2690B for monkey and rat compared with human; and c) determine the binding affinity of VPI-against native human β3 in normal and high glucose conditions and also to characterize the dose-response relationship between VPI-2690B binding to native αVβ3 and its potency in blocking signal transduction.

Plates were coated with 100 µl/well of appropriate C-loop peptide conjugate in coating buffer at concentration of 5 µg/ml at 4° C. overnight (18-20 hours) with rocking Plates were then washed with 0.05% Tween PBS (200 µl/well×3 washes), then blocked with 200 µl/well blocking buffer at 4° C. overnight (18-20 hours) with rocking. Then the washing step was repeated.

The standard curve (1.95 ng/mL-2000 ng/mL) (50 µl/well) created from each of the test article preparations being tested was added to duplicate wells of the plate and incubated for 1 hour at room temperature with rocking. The plates were then washed again with 0.05% Tween PBS (200 µl/well×3 washes). Next, 100 µl/well of HRP-labeled goat anti-secondary antibody (1:200,000 dilution in ELISA buffer) was added and incubated for 2 hours at room temperature with rocking. The plates were washed with 0.05% Tween PBS (200 µl/well×3 washes). Then 100 µl/well of TMB substrate was added and color was allowed to develop for 20 minutes with shaking at room temperature. Sulfuric acid (100 µl/well of 2M sulfuric acid) was added to stop the reaction. The plates were then shaken for 5 seconds. The plates were read at 450 nm on a Molecular Devices SPECTRA MAX Plus instrument. GraphPad Prism was used to fit the data in the equation for log (agonist) vs. response—variable slope (four parameters).

Maintenance of Chinese Hamster Ovary Cell Lines. Cells were passaged at 80~90% confluency and maintained in αMEM medium, supplemented with 5% FBS and 0.8 mg/mL Geneticin.

Maintenance of Human Umbilical Vein Endothelial Cells. Cells were passaged at 8090% confluency and maintained in MCDB 131 medium supplemented with endothelial growth medium (EGM) SingleQuot Kit and 1×L-Glutamine.

Method to Create Cell Line Expressing Human, Monkey or Rat β3. The human (Huβ3) and rat integrin β3 (RAβ3) constructs were obtained as described; the monkey integrin β3 (MOβ3) construct was produced by site-directed mutagenesis using the human β3 construct as the template, based on the sequence of predicted *Callithrix jacchus* integrin (Accession #: XM_002748126).

CHO-K1 cells were plated in 6-well plate at a confluency of ~50%. The next day, 3 µg of deoxyribonucleic acid (DNA) construct (human, monkey or rat) were mixed with 250 µL of Opti-MEM and then combined with a mixture of 9 µl of lipofectamine 2000 and 250 µl of Optim-MEM. The mixture was incubated at room temperature for 30 minutes. The mixture was then added to the cell monolayers, drop by drop, and the cells returned to the incubator.

Four hours later the transfection mixture was aspirated, the cells were rinsed one time with DPBS. The monolayers were then re-seeded in a 10-cm dish. The following day the culture medium was replaced with fresh medium containing Geneticin (final concentration 1.6 mg/mL). The medium (with Geneticin at 1.6 mg/mL) was changed every other day for a total of 10 to 14 days until the cells grew to be confluent. The monolayers were then trypsinized and re-seeded into new dishes for expansion. Cells were maintained in medium containing 0.8 mg/mL Geneticin. Expression of β3 protein was confirmed using western immunoblotting of cell lysates.

Cells were cultured in 10 cm petri dishes until they attained confluence. Culture medium was aspirated and cells washed in ice-cold DPBS once. In each dish, 1 mL of lysis buffer (radio immunoprecipitation assay [RIPA] buffer supplemented with 1×HALT proteinase/phosphatase inhibitors) was added and cells then left on ice for 20 minutes before being collected with scrapers. Lysed cells were then spun down at 12000 g for 15 minutes and supernatants collected.

Cell lysates were subjected to SDS-PAGE analysis. Briefly, about 20 µg of total proteins from each lysate per well were loaded on a 4-15% gradient gel. The gels were run at 200V for 35 minutes in 1× electronic buffer to separate the proteins, which were then transferred to polyvinylidene difluoride (PVDF) membranes (100V, 1 hour). The membranes were blocked in 3% BSA in 1×TBST (tris-buffered saline+Tween) buffer and blotted with in house rabbit anti-integrin β3 antibody (1:2000 in 1.5% BSA) at room temperature for 1 hour. After being washed in 1×TBST for 10 minutes×3 times, the membranes were further incubated with secondary antibody (Ab) (anti-rabbit antibody, 1:20,000 in 1×TBST) at room temperature for 1 hour.

The membranes were washed in 1×TBST for 10 minutes×3 times, and followed by 1×TBS for 10 minutes. SuperSignal West Pico Chemiluminescent Substrate was used to detect the signals.

Figure 8:
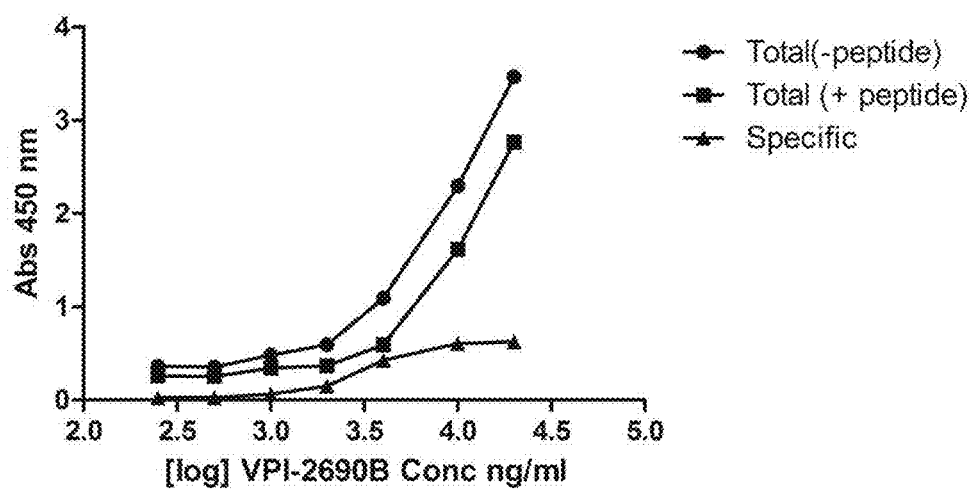
FIG. 8. VPI-2690B binding to CHO-K1 Cells Expressing Human β3 (CHO-Hub3). Graph shows total binding of VPI-2690B (− peptide) binding in the presence of the C-loop antigen peptide (+ peptide) and the calculated specific binding [(binding−peptide)−(binding+peptide)].
Figure 9:
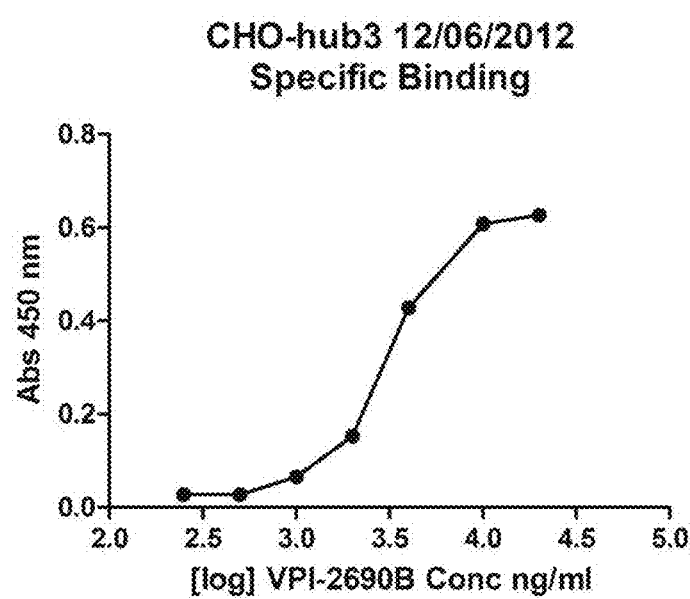
FIG. 9. VPI-2690B Binding to CHO-K1 Cells Expressing Human β3 (CHO-Hub3). Graph shows the calculated specific binding [(binding−peptide)−(binding+peptide)].

The method reported here was used for data shown in Table 9, FIG. 8, and FIG. 9.

The 96-well plates were coated with poly-d-lysine (0.1 mg/mL) for 30 minutes at room temperature and then rinsed with distilled water and dried at room temperature for 2 hours.

CHO cells (expressing appropriate (33) were seeded at 1250 cells/well and cultured in growth medium for 4 days.

On the day of assay, 2 stock solutions of VPI-2690B were prepared at 2 mg/mL in SFM. To one tube, C-loop peptide was added at a final concentration of 53.3 μM (200-fold molar excess of peptide). Serial dilutions of each of the two stock tubes of VPI2690B were prepared in SFM and incubated at room temperature for 1 hour. Diluted VPI-2690B+/−C-loop peptide were added in triplicate to the cells in the 96-well plates and incubated with cells for 1 hour at 37° C.

Cells were washed with DPBST twice and DPBS twice (manually) before fixing the cells using 3.7% formaldehyde in 1×PBS at room temperature for 20 minutes. The cells were then washed with DPBS 3 times using a plate washer with manifold at the vertical position at a setting of 350. Wells were then blocked by adding 200 μL of blocking buffer (1% casein) at room temperature for 1 hour with moderate shaking Plates were washed again using DPBS 3 times and then HRP-conjugated secondary at 1:4000 dilution) and incubated at 37° C. for 1 hour. Plates were washed manually ×2 with DPBST and then 3 times with DPBS (with plate washer). TMB substrate was then added and the reaction was allowed to proceed for 20 minutes before stopping the reaction with 2M $H_2SO_4$. The plates were read at 450 nm on a Molecular Devices SPECTRA MAX Plus instrument.

Figure 10:
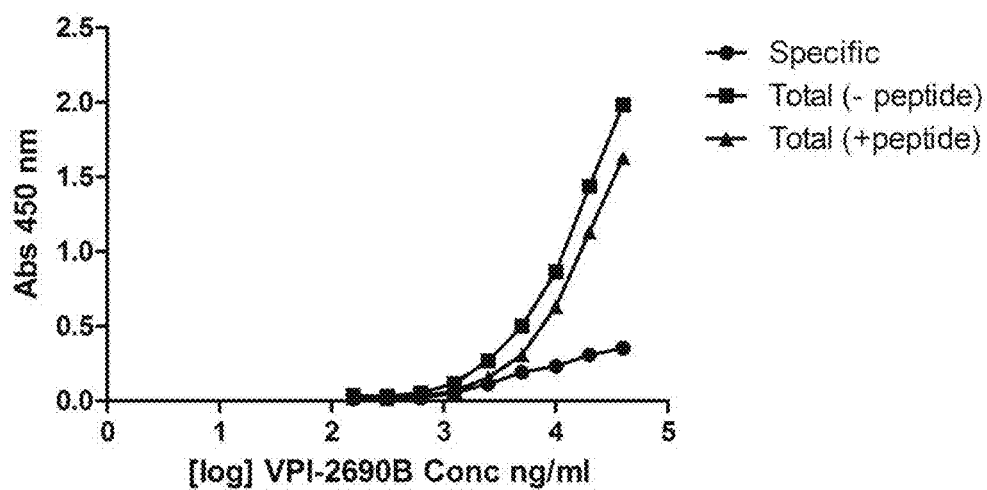
FIG. 10. VPI-2690B Binding to Human Umbilical Vein Endothelial Cells Cultured in High Glucose Conditions. Graph shows total binding of VPI-2690B (− peptide) binding in the presence of the C-loop antigen peptide (+ peptide) and the calculated specific binding [(binding−peptide)−(binding+peptide)].
Figure 11:
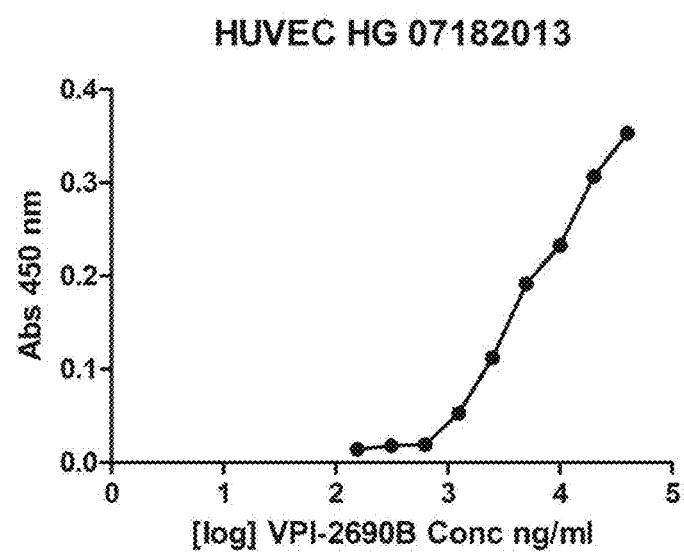
FIG. 11. VPI-2690B Binding to Human Umbilical Vein Endothelial Cells Cultured in High Glucose Conditions. Graph shows the calculated specific binding [(binding−peptide)−(binding+peptide)].

The method reported here was used for data shown in Table 10, FIG. 10, and FIG. 11.

HUVEC cells were seeded into 96-well plates at 100 μL/well, with about 1500 cells/well. Cells were further cultured in the 96-well plates in growth medium (supplemented with 25 mM D-Glucose if required) for 3 to 4 days before the cell-base ELISA (cELISA) was performed.

Two stock solutions of VPI-2690B were prepared at 2 mg/mL in 1% Casein. To one tube, C-loop peptide was added at a final concentration of 53.3 uM (200-fold molar excess of peptide). Serial dilutions of each of the 2 stock tubes of VPI-2690B were prepared in 1% Casein and incubated at room temperature for 1 hour. Diluted VPI-2690B+/−C-loop peptide was added in triplicate to the cells in the 96-well plates and incubated with cells for 1 hour in a cold room at 4° C. After being washed with washing buffer, cells were fixed in Formalin (3.7%) and blocked in 1% Casein. Cells were further incubated with HRP conjugated secondary Ab (1:2000 dilution) at room temperature for 1 hour. Plates were then washed and TMB substrate added. After 20 minutes, the stop buffer was added. The plates were read at 450 nm on a Molecular Devices SPECTRA MAX Plus instrument.

Figure 12:
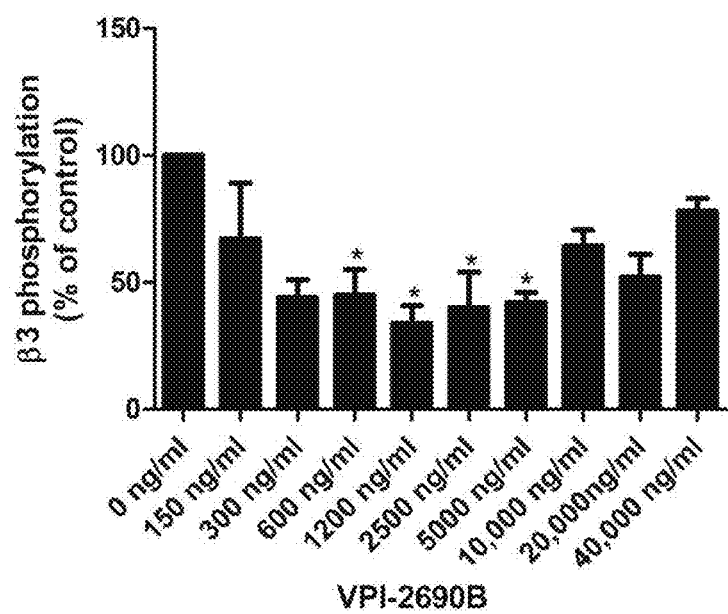
FIG. 12. VPI-2690B Dose Response of β3 Phosphorylation in Human Umbilical Vein Endothelial Cells under High Glucose Conditions. Graph shows the percent reduction in 133 phosphorylation following treatment with VPI-2690B compared with control (no treatment).

The Method described here was used for data shown in FIG. 12 and Table 11.

Cells were plated in 6-cm dishes (3×10^5/dish) in growth medium+25 mM glucose. Cells reached confluence over 3 days. On Day 2, growth medium was replaced with fresh medium+25 mM glucose and cells kept culturing for overnight. On Day 3, growth medium was aspirated and cells rinsed once with SFM (MCDB 131). VPI-2690 diluted in SFM supplemented with 2 5 mM glucose was then added to get the appropriate final concentration (from 156 ng/ml to 40000 ng/ml).

Plates were returned to 37° C. incubator for 30 minutes. At the end of the incubation, plates were removed from the incubator, SFM aspirated, cultures rinsed with ice-cold PBS and 300 μL of RIPA was added to each dish. After 20 minutes on ice, RIPA+cell lysate scraped was from each plate and transferred into 1.5 mL microcentrifuge tubes and centrifuged at 13000 rpm×15 minutes. The clarified supernatant was transferred into new tubes and stored at −80° C. before further analysis.

Equal amounts of lysate (15 μg) were mixed with 2× sample buffer and heated to 95 C for 5 minutes before being separated on a 4-15% SDS-PAGE gel (200V, 40 minutes).

Proteins were then transferred to PVDF (100V, 60 minutes) in 1× transfer buffer with 10% MeOH. Membranes were then blocked in 3% BSA at room temp for 2 hours before incubating overnight with anti-phosphor β3 antibody (1:3000 1.5% BSA) in a cold room at 4 C. The next day, membranes were washed using 1×TBST, 10 minutes for 3 times before incubating with secondary Ab (anti-rabbit, 1:20,000 in 1.5% BSA) at room temp for 1 hour. The membranes were then washed with 1×TBST, 10 minutes for 3 times, and then 1×TBS for 10 minutes before detection with a Thermo Scientific SuperSignal kit (cat #34080) and exposure to x-ray film for 20 seconds.

The films were digitized by scanning at 600 dpi on a DuoScan. The scans of individual gels were converted to tif files in Photoshop. The tif files were analyzed with ImageJ software using the Gel Analyzer Tool in ImageJ. This tool reports the results in arbitrary units.

The affinities of VPI-2690B and related antibodies for the peptide antigen are shown in Table 8. The affinity of the antibody for the human peptide antigen was increased approximately 5-fold during the optimization process, from 1.2 nM for the parent murine monoclonal to 0.28 nM for the final humanized antibody, VPI-2690B. The parent murine monoclonal antibody had a higher affinity for the human peptide than either the rat or mouse. The VH5VK2 intermediate had equal affinities for both human and rat peptides, and VPI-2690B had a higher affinity for human than mouse but equal affinity for human and rat peptide sequences.

The $EC_{50}$ for the human-mouse chimera (comprising the heavy and light chain variable region [VH and VK] of the C-loop mouse monoclonal antibody and the human $IgG_1$ heavy chain and kappa light chain constant region) and the humanized VH5VK2 antibody was measured using the rhabdomyosarcoma cell line by flow cytometry Table 9). The affinity of VPI-2690B for human β3 was measured in CHO cells transfected to express human β3. The $EC_{50}$ (20.33 nM) was comparable to that obtained for the developmental forms.

The relative binding affinity of CHO cells expressing human, monkey, and rat β3 is shown in Table 10, Binding of VPI-2690B to cells expressing human, monkey and rat β3 was comparable (20.33±5.8 vs 22.49±4.7 vs 12.92±1.3, respectively). An example result is shown in FIG. 7, which shows total binding and binding in the presence of the C-loop peptide (non-specific) and FIG. 8 (the difference between the binding in the presence and absence of the peptide i.e., specific) in CHO-HuP3 cells.

The binding affinity of VPI-2690B was measured using HUVEC cells. The $EC_{50}$ values for VPI-2690B binding to human integrin β3 in HUVECs is 11.8±1.3 (mean±SEM, n=4; Table 11). This is comparable to that obtained in the CHO cells expressing human β3.

Since VPI-2690B is being developed to treat diabetic nephropathy, the binding affinity of VPI-2690B for native human β3 in high glucose conditions was also calculated using HUVEC cells. The $EC_{50}$ in high glucose medium is 32.9±4.3 (mean±SEM n=6; Table 11).

Example data are presented in FIG. 10, which shows total binding and binding in the presence of the C-loop peptide, and FIG. 11, which shows the difference between binding in the presence and absence of the peptide (ie, specific binding).

The potency and dose response of VPI-2690B in vitro at reducing β3 phosphorylation was tested by exposing HUVECs, cultured in high glucose, to a range of concentrations of VPI-2690B. VPI-2690B was partially active at 150 ng/mL and fully active in vitro at concentrations between 300 and 600 ng/mL (Table 12 and FIG. 12) resulting in a significant reduction of approximately 45±10.0% of the β3 phosphorylation compared with control at 600 ng/mL [mean±SEM n=3] p<0.05]. This is slightly higher than the lowest serum levels of VPI-2690B that were fully active (200 ng/mL) in vivo. These data suggest that maximal inhibition of β3 phosphorylation occurs at <50% receptor occupancy.

Importantly, VPI-2690B does not stimulate baseline levels of β3 phosphorylation (FIG. 12), indicating that the antibody is a full antagonist of the receptor. The inhibition of β3 phosphorylation by VPI-2690B is dose-responsive at low antibody concentrations and returns toward baseline at high concentrations, suggesting that the bivalency of the antibody may play a role in controlling the phosphorylation state of β3 in intact cells.

The affinity for the human 133 expressed in CHO cells is 20.33 nM, which is within the range of the affinity of VPI-2690B for endogenous human 133 in HUVEC (11.8 nM and 32.9 nM), confirming the relevance of this model of comparing affinity of VPI-2690B for human, rat, and monkey 133.

The affinity for the monkey 133 expressed in CHO cells is 22.49±4.7 nM, which is comparable to human 133 expressed in the same cell type (20.33±5.8) and also comparable to binding to endogenous β3 in HUVEC under the same normal glucose culture conditions (11.8±1.3 nM).

The affinity for the rat β3 expressed in CHO cells is 12.92±1.3 nM, which is comparable to both the human and monkey value.

EXAMPLE 11

The objective of this study was to compare VH5VK2 and VPI-2690B for their ability to inhibit β3 phosphorylation, ERK 1/2, and AKT in porcine smooth muscle cells (SMCs).

Porcine SMCs were isolated from the porcine aortic explants. Briefly, after removal of interstitial tissue and endothelium, small sections of aortic explants were placed directly on the plastic surface of several p100 tissue culture dishes. The explants were covered with 10 mLs of growth medium (Dulbecco's Modified Eagle's Medium [DMEM]) containing 4500 mg/l (25 mM) glucose plus 10% fetal bovine serum and penicillin (1000 U/mL) and streptomycin (160 µg/mL)] referred to as high glucose growth medium (HG-GM). SMCs were observed to have migrated from the explant after 4 to 7 days.

Once SMCs were observed to have migrated from the explant and attached to the surface of the dish, the explants were removed (between 5 and 7 days). At this point, half of the plates were maintained in HG-GM while the remaining half of the plates were maintained in DMEM containing 900 mg/L of glucose (5 mM) plus 10% fetal bovine serum and penicillin and streptomycin (normal glucose growth medium [NG-GM]). SMCs were fed every 3 days with either HG or NG-GM and were passed every 7 days in appropriate medium. SMCs were maintained under these conditions for a further three passages prior to be used for experiments.

All experiments were performed on SMCs between passage 4 and 10. Except where described, SMCs were maintained from passage to passage in medium with the same glucose concentration. Prior to initiation of each experiments confluent monolayers were washed three times in serum free medium and incubated overnight (16-17 hours) in serum free medium containing the glucose concentration equivalent to that in which they had been grown (25 mM glucose=SFM-H or 5 mM glucose=SFM-N). SFM-N was supplemented with mannitol to ensure that any differences observed between the different glucose concentrations were not due to differences in osmolarity.

Porcine smooth muscle cells were seeded using a density of $1 \times 10^5$/well onto six-well culture plates in DMEM-H with 10% FBS, and incubated for 2-3 days. The cells were then serum-starved in serum-free DMEM-H overnight. Two sets of 7 wells were set up for each of the two antibodies being tested. The medium in each well was then changed to DMEM-H alone (well 1 for each set of 7 wells) or antibody treatments (wells 2-6 for each set of 7 wells; 0.005, 0.05, 0.1, 0.5, 1 and 2 µg/mL) and incubated for 4 hours. The cells in one set of 7 wells (no antibody and antibody treatments 2-6) were then directly stimulated with IGF-1 (50 ng/mL) for 10 minutes. The media was then removed from all the wells and the cell monolayers were then lysed in 300 µL of radioimmunoprecipitation assay (RIPA) buffer. Forty µL of the resulting lysate are then loaded onto an 8% polyacrylamide gel, separated, and transferred onto a polyvinylidine difluoride (PVDF) membrane to immunoblot for phosphorylated and total ERK 1/2 and AKT and total β3. The remainder of the lysate was immunoprecipitated with an anti-β3 antibody and following separation on an 8% polyacrylamide gel and transfer to a PVDF membrane, immunoblotted with an anti-phosphotyrosine antibody. After immunoblotting, films were scanned and then arbitrary density obtained to then calculate the reduction in pERK, pAKT (in response to insulin-like growth factor 1 [IGF-1]) and pβ3 (basal) with each variant compared with basal or IGF-1 treatment.

To quantify the effect of antibody treatment on basal β3 phosphorylation, western immunoblots were digitized and the intensity of the signal from untreated wells was calculated and then compared with the values obtained in a similar manner corresponding to the wells treated with increasing concentrations of either VPI-2690B or VH5VK2. The relative ability of VPI-2690B and VH5VK2 to inhibit IGF-1 stimulated ERK1/2 and AKT phosphorylation was evaluated in a similar matter, but using the data obtained from the wells containing cells treated with IGF-1 following antibody stimulation. Raw data and a summary of inhibition of IGF-stimulated β3 phosphorylation of AKT, ERK and basal β3 phosphorylation by VH5VK2 and VPI-2690B are presented in Table 13 and Table 14, respectively. Data are presented graphically in FIG. 13.

Figure 13:
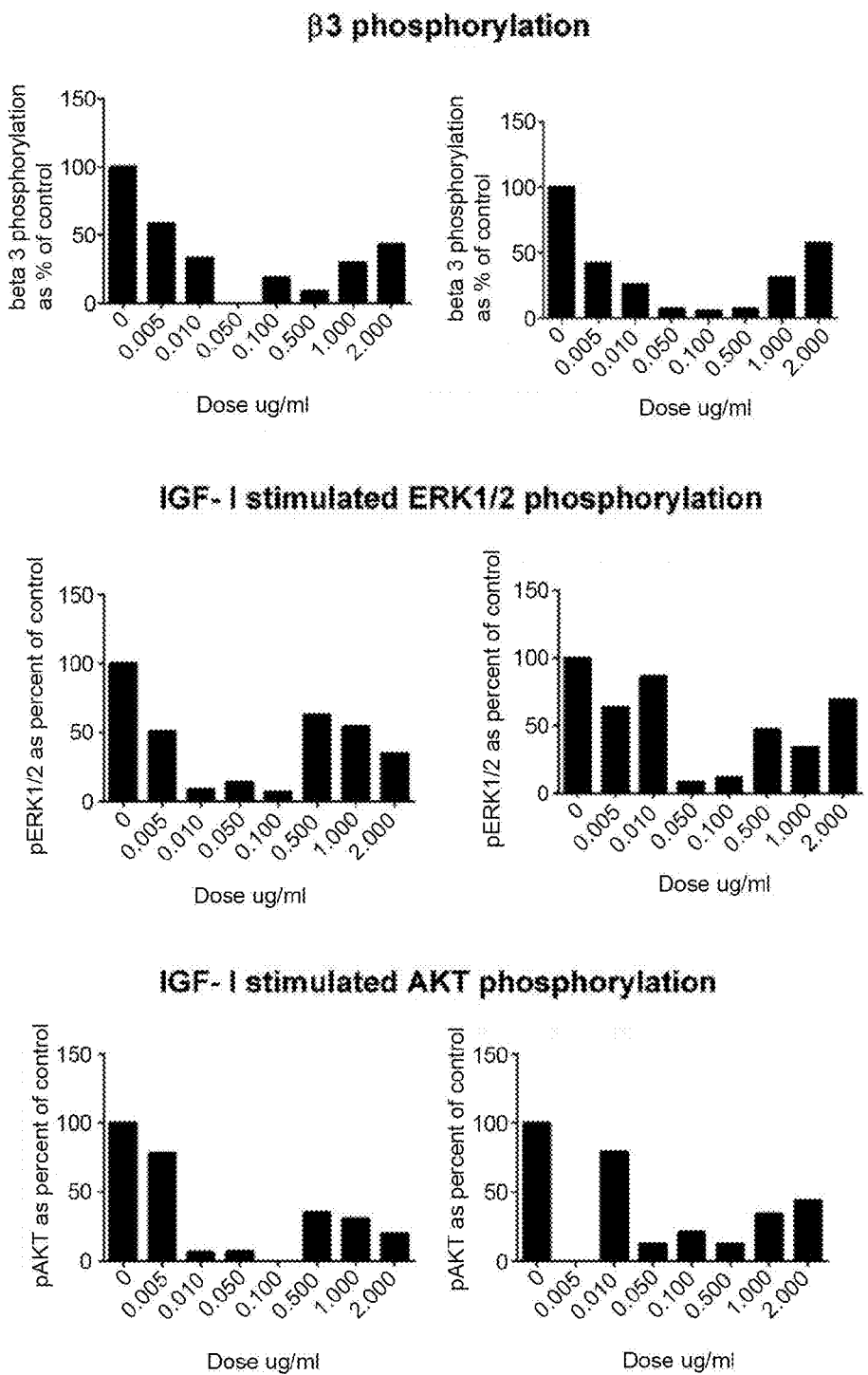
FIG. 13. Inhibition of IGF-1-Stimulated Phosphorylation of AKT, ERK, and Basal β3 Phosphorylation by VH5VK2 and VPI-2690B.

FIG. 13 and Table 14 summarize the β3 phosphorylation data with the pAKT and pERK data. The "max inhibitory" column shows the concentration at which the antibody variants were maximally effective at inhibiting IGF-1-stimulated ERK and AKT phosphorylation and basal β3 phosphorylation. The "% inhibition" column shows the ability (expressed as a % where complete inhibition=100%) of the maximally inhibitory antibody concentration to inhibit each of the parameters tested.

VH5VK2 was maximally inhibitory between 0.01 and 0.5 µg/mL. Similarly, VPI-2690B was maximally inhibitory between 0.05 and 0.1 µg/mL.

Both VPI-2690B and VH5VK2 were able to exert a significant inhibition of all 3 parameters studied, consistent with the calculated $EC_{50}$ and efficacy in vivo.

The inhibition of β3 phosphorylation by both VH5VK2 and VPI-2690B is dose-responsive at low antibody concentrations and returns toward baseline at high concentrations, suggesting that the bivalency of the antibody may play a role in controlling the phosphorylation state of β3 in intact cells.

The foregoing is illustrative of the present invention, and is not to be construed as limiting thereof. The invention is defined by the following claims, with equivalents of the claims to be included therein.

Applicants specifically intend that all patents, patent publications and nonpatent references cited herein be incorporated herein by reference in their entirety.

TABLE 1

Binding of purified antibody variants to RD cells that express $α_Vβ_3$

| Heavy chain variant | Light chain variant | | |
|---|---|---|---|
| | Vκ1 | Vκ2 | Vκ3 |
| VH1 | N/D | 5.43 | 4.08 |
| VH2 | 4.55 | 4.92 | 3.70 |
| VH3 | 4.85 | 47.38 | 3.13 |
| VH4 | 3.12 | N/D | 2.03 |
| VH5 | 4.42 | 3.43 | 3.15 |

$EC_{50}$ values (nM) of NS0-derived Composite Human Antibody™ variants. In the same assay, chimeric IgG1 had a calculated $EC_{50}$ of 3.58 nM.

TABLE 2

Binding of purified antibody variants to RD cells that express $α_Vβ_3$

| Heavy chain variant | Light chain variant | | |
|---|---|---|---|
| | Vκ1 | Vκ2 | Vκ3 |
| VH1 | N/D | 1.52 | 1.14 |
| VH2 | 1.27 | 1.37 | 1.03 |
| VH3 | 1.35 | 13.22 | 0.87 |

TABLE 2-continued

Binding of purified antibody variants to RD cells that express $α_Vβ_3$

| Heavy chain variant | Light chain variant | | |
|---|---|---|---|
| | Vκ1 | Vκ2 | Vκ3 |
| VH4 | 0.87 | N/D | 0.57 |
| VH5 | 1.23 | 0.96 | 0.88 |

Relative binding scores of NS0-derived Composite Human Antibody™ variants obtained by dividing $EC_{50}$ values of variant by the $EC_{50}$ of chimeric HLMC. A relative binding score >1.0 indicates improved binding of the variant compared to chimeric. Antibodies highlighted in bold are recommended as lead candidates based on the relative binding to RD cells.

TABLE 3

T cell proliferative response to various forms of the antibody

| | Mean Sl ± SD | % Response |
|---|---|---|
| Chimeric | 2.46 ± 0.25 | 20 |
| Vh5/Vk2 | 3.25 | 5 |
| Vh4/Vk1 | — | 0 |
| KLH | 4.08 ± 0.46 | 65 |

Table 3. Summary of the magnitude (+SD) of positive T cell proliferation responses Sl≥2.0, p<0.05 against test antibodies. The mean Sl was calculated from the average of all positive donor responses observed during the entire time course (days 5-8).

TABLE 4

Amino acid sequences and corresponding sequence identifiers

| Amino Acid Sequence | SEQ ID NO |
|---|---|
| LCDR1 | 1 |
| LCDR2 | 2 |
| LCDR3 | 3 |
| HCDR1 | 4 |
| HCDR2 | 5 |
| HCDR3 | 6 |
| VH1 | 7 |
| VH2 | 8 |
| VH3 | 9 |
| VH4 | 10 |
| VH5 | 11 |
| VH6 | 12 |
| Vκ1 | 13 |
| Vκ2 | 14 |
| Vκ3 | 15 |
| Vκ2 and constant region | 16 |
| VH6 and constant region | 17 |
| Mouse Vκ | 18 |
| Vκ2 substitutions | 19 |
| Mouse VH | 20 |
| VH6 substitutions | 21 |
| Vκ1 and constant region | 22 |
| Vκ3 and constant region | 23 |
| VH1 and constant region | 24 |
| VH2 and constant region | 25 |
| VH3 and constant region | 26 |
| VH4 and constant region | 27 |
| VH5 and constant region | 28 |
| Vκ1 substitutions | 39 |
| Vκ3 substitutions | 40 |
| VH1 substitutions | 41 |
| VH2 substitutions | 42 |
| VH3 substitutions | 43 |
| VH4 substitutions | 44 |
| VH5 substitutions | 45 |

TABLE 5

Mean Body Weight and Glucose Levels at Start and End of the Study by Treatment Group

| Variable | | VPI-2690B Dose (mg/kg) | | | | | | |
|---|---|---|---|---|---|---|---|---|
| | | 0 | 0.01 | 0.03 | 0.1 | 0.3 | 0.5 | 1 |
| Start weight (grams) | Mean | 260.8 | 283.8 | 268.3 | 261 | 253.5 | 277.5 | 265.3 |
| | SD | 16.07 | 54.61 | 7.365 | 8.602 | 16.05 | 13.77 | 5.62 |
| End weight (grams) | Mean | 309.8 | 291 | 323.5 | 300.5 | 287.8 | 331.3 | 310 |
| | SD | 32.04 | 17.66 | 14.27 | 25.38 | 6.449 | 13.96 | 34.55 |
| Starting glucose (mg/dL) | Mean | 234.5 | 262.3 | 285 | 268.5 | 267.8 | 260.5 | 289.5# |
| | SD | 18.77 | 29.07 | 48.9 | 82.19 | 44.42 | 38.65 | 27.2 |
| Ending glucose (mg/dL)* | Mean | 353.3 | 403.5 | 368.5 | 378.8 | 358.8 | 436 | 396.3 |
| | SD | 17.9 | 82.08 | 108.7 | 81.99 | 46.24 | 67.88 | 99.71 |

*not fasting
Abbreviation:
SD = standard deviation;
$p < 0.05$ vs untreated control group.

TABLE 6

VPI-2690B levels (in ug/ml) in serum measured in serum on Day 8
(30 minutes before second injection)

| | Con | 0.01 | 0.03 | 0.1 | 0.3 | 0.5 | 1 |
|---|---|---|---|---|---|---|---|
| R1 | <LOQ | <LOQ | 0.199551 | 0.651367 | 1.328981 | 0.853122 | 1.33867 |
| R2 | <LOQ | <LOQ | 0.135142 | | 1.572269 | 2.531982 | 2.566546 |
| R3 | <LOQ | <LOQ | 0.152336 | 0.531295 | 1.307642 | 1.70441 | 3.294116 |
| R4 | <LOQ | <LOQ | 0.093545 | 0.451015 | 1.6088 | 2.345218 | 2.361622 |
| Mean | 0 | 0 | 0.1451 | 0.5446 | 1.454 | 1.859 | 2.39 |
| Std. Deviation | 0 | 0 | 0.04387 | 0.1008 | 0.1581 | 0.7583 | 0.8072 |
| Std. Error | 0 | 0 | 0.02194 | 0.05822 | 0.07906 | 0.3791 | 0.4036 |

VPI-2690B levels (in ug/ml) in serum measured in serum on Day 15
(at necropsy 7 days after second injection)

| dose mg/kg | Con | 0.01 | 0.03 | 0.1 | 0.3 | 0.5 | 1 |
|---|---|---|---|---|---|---|---|
| R1 | <LOQ | <LOQ | 0.237532 | 0.059008 | 1.499907 | 0.776928 | 0.77163 |
| R2 | <LOQ | <LOQ | 0.14165 | 0.649752 | 0.610261 | 2.275514 | 3.988542 |
| R3 | <LOQ | <LOQ | 0.221744 | 0.655034 | 1.69012 | 2.49016 | 4.329474 |
| R4 | <LOQ | <LOQ | 0.099979 | 2.103948 | 2.567192 | 2.795438 | 3.620796 |
| Mean | 0 | 0 | 0.1752 | 0.8669 | 1.592 | 2.085 | 3.178 |
| Std. Deviation | 0 | 0 | 0.06541 | 0.8708 | 0.8027 | 0.8974 | 1.63 |
| Std. Error | 0 | 0 | 0.03271 | 0.4354 | 0.4013 | 0.4487 | 0.8149 |

R = rat
LOQ = Limit of quantification (0.04 ug/ml)

TABLE 7

β3 phosphorylation as % of control versus dose (mg/kg)

| | Con | 0.01 | 0.03 | 0.1 | 0.3 | 0.5 | 1 |
|---|---|---|---|---|---|---|---|
| Mean | 100 | 38.4 | 14.31 | 21.72 | 24.24 | 13.65 | 14.88 |
| Std. Deviation | 0 | 16.52 | 3.264 | 8.889 | 11.49 | 3.291 | 3.129 |
| Std. Error | 0 | 8.262 | 1.632 | 4.444 | 5.744 | 2.327 | 2.213 |
| p Vs control | | 0.01 | 0.001 | 0.002 | 0.003 | 0.02 | 0.02 |

TABLE 8

Affinities of VPI-2690B and Related Antibodies for the Peptide Antigen

| Antibody Name | Description | $K_d$ for Peptide Antigen (nM) | | |
|---|---|---|---|---|
| | | Human n = 3 | Rat n = 3 | Mouse n = 3 |
| C-loop | parent murine monoclonal IgG1 | 1.2 ± 0.1 | 16.0 ± 9.0 | 6.7 ± 2.0 |
| VH5VK2 | humanized monoclonal IgG1 | 0.21 ± 0.04 | 0.18 ± 0.15 | ND |
| VPI-2690B | optimized humanized monoclonal IgG1 | 0.28 ± 0.03 | 0.25 ± 0.03 | 2.7 ± 0.3 |

Abbreviations: IGg = immunoglobulin g; Kd = dissociation constant; ND = not determined
Note:
Values shown are mean ± SD

TABLE 9

EC$_{50}$s for the Human-Mouse Chimera, VH5VK2, and VPI-2690B Binding to Native Human β3

| Antibody Name | Cell | Method | EC$_{50}$ for Binding to Native Human β3 (nM) |
|---|---|---|---|
| C-loop chimera | Binding to rhabdomysarcoma cells | Flow cytometry | 24 [1] |
| VH5VK2 | Binding to rhabdomyosarcoma cells | Flow cytometry | 18 [2] |
| VPI-2690B | CHO-K1 - Huβ3 | Cell based ELISA | 20.33 ± 5.8* |

[1] Binding of C-loop human-mouse chimera to human rhabdomyosarcoma cells
[2] Binding of VH5VK2 to human rhabdomyosarcoma cells
*mean ± SEM;
N = 3 assays

TABLE 10

Relative Binding of Chinese Hamster Ovary Cells Expressing Human, Monkey, and Rat β3 to VPI-2690B

| | EC$_{50}$ (nM) | | |
|---|---|---|---|
| | Human (N = 3) | Monkey (N = 3) | Rat (N = 3) |
| VPI-2690B | 20.33 ± 5.8 | 22.49 ± 4.7 | 12.92 ± 1.3 |

Note:
Values shown are mean ± standard error of the mean

TABLE 11

Median Effective Concentration for VPI-2690B binding to Human Integrin β3 in Human Umbilical Vein Endothelial Cells under Normal and High Glucose Conditions

| Glucose Concentration for Cell Culture | EC$_{50}$ nM | N |
|---|---|---|
| NG (5 mM/L) | 11.8 ± 1.3 | 4 |
| HG (25 mM/L) | 32.9 ± 4.3 | 6 |

Abbreviations: HG = high glucose; NG = normal glucose; EC$_{50}$ = median effective concentration; SEM = standard error of the mean.
Note:
Values shown are mean ± SEM

TABLE 12

VPI-2690B Dose Response of β3 Phosphorylation in Human Umbilical Vein Endothelial Cells under High Glucose Conditions

| Concentration of VPI-2690B (ng/ml) | β3 Phosphorylation Compared with Control (mean ± SD) | N | p-Value versus Control |
|---|---|---|---|
| 150 | 67 ± 3.1 | 2 | 0.2 |
| 300 | 51 ± 7.0 | 2 | 0.2 |
| 600 | 45 ± 17.5 | 3 | 0.02 |
| 1200 | 34 ± 12.4 | 3 | 0.01 |
| 2500 | 40 ± 25.4 | 3 | 0.05 |
| 5000 | 42 ± 8.2 | 3 | 0.02 |
| 10000 | 64 ± 10.9 | 3 | 0.06 |
| 20000 | 52 ± 15.9 | 3 | 0.06 |
| 40000 | 79 ± 10.1 | 3 | 0.2 |

Abbreviation: SD = standard deviation

TABLE 13

Inhibition of IGF-1-Stimulated, ERK ½, and AKT Phosphorylation and Basal β3 Phosphorylation by VH5VK2 and VPI-2690B-Raw Data

| Antibody | VH5VK2 | | | VPI-2690B | | |
|---|---|---|---|---|---|---|
| Concentration (µg/mL) | Scan Units | % of control | % reduction | Scan Units | % of control | % reduction |
| AKT-Treated (Control Scan Unit [AKT no antibody] = 10080) | | | | | | |
| 2 | 2023 | 20.1 | 79.9 | 4467 | 44.3 | 55.7 |
| 1 | 3109 | 30.8 | 69.2 | 3467 | 34.4 | 65.67 |
| 0.5 | 3600 | 35.7 | 64.2 | 1233 | 12.2 | 87.8 |
| 0.1 | ND | ND | ND | 2120 | 21.0 | 78.98 |
| 0.05 | 689 | 6.8 | 93.2 | 1240 | 12.3 | 87.7 |
| 0.01 | 643 | 6.4 | 93.6 | 7972 | 79.1 | 20.9 |
| 0.005 | 7900 | 78.4 | 21.6 | ND | ND | ND |
| ERK-Treated (Control Scan Unit [ERK no antibody] = 12140) | | | | | | |
| 2 | 4160 | 34 | 66 | 8415 | 69.3 | 30.7 |
| 1 | 6570 | 54.1 | 45.9 | 4168 | 34.3 | 65.7 |
| 0.5 | 7597 | 62.6 | 37.49 | 5758 | 47.4 | 52.6 |
| 0.1 | 818 | 6.7 | 93.3 | 1325 | 10.9 | 89.10 |
| 0.05 | 1665 | 13.7 | 86.3 | 1007 | 8.3 | 91.8 |
| 0.01 | 1028 | 8.5 | 91.5 | 1684 | 13.9 | 86.1 |
| 0.005 | 6130 | 50.5 | 49.5 | 7684 | 63.3 | 36.7 |
| β3-Untreated (Control Scan Unit [β3 no antibody] = 16184) | | | | | | |
| 2 | 6931 | 42.9 | 57.2 | 9247 | 57.3 | 42.9 |
| 1 | 4843 | 29.9 | 70.1 | 4968 | 30.7 | 69.3 |
| 0.5 | 1409 | 8.7 | 91.3 | 1147 | 7.1 | 92.9 |
| 0.1 | 2962 | 18.3 | 81.7 | 814 | 5.0 | 94.5 |
| 0.05 | ND | ND | ND | 1150 | 7.1 | 92.9 |
| 0.01 | 5316 | 32.89 | 67.19 | 4113 | 25.49 | 74.6 |
| 0.005 | 9397 | 58.1 | 41.9 | 6764 | 41.8 | 58.2 |

AKT = protein kinase B alpha; ERK = extracellular signal related kinase; ND = not done.

TABLE 14

Calculated Maximum Inhibitory Concentration and Maximum Percent Inhibition of β3 Phosphorylation and IGF-1 stimulated ERK1/2 and AKT by VH5VK2 and VPI-2690B

|  | ERK ½ | | AKT | | pβ3 | |
| --- | --- | --- | --- | --- | --- | --- |
|  | Max inhibitory concentration (µg/mL) | Max % inhibition | Max inhibitory concentration (µg/mL) | Max % inhibition | Max inhibitory concentration (µg/mL) | Max % inhibition |
| VH5VK2 | 0.01 | 91 | 0.01 | 93 | 0.5 | 92 |
| VPI-2690B | 0.05 | 92 | 0.05 | 87 | 0.1 | 93 |

AKT = protein kinase B alpha; ERK = extracellular signal related kinase; Max = maximum

---

That which is claimed is:

1. An isolated polynucleotide comprising a nucleic acid sequence that encodes a polypeptide comprising a light chain variable region of an antibody or antigen binding fragment that binds the $\alpha_v\beta_3$ integrin cysteine loop (C-loop) domain of SEQ ID NO: 29, wherein the light chain variable region comprises:
    (a) a light chain complementary determining region 1 (LCDR1) of SEQ ID NO: 1;
    (b) a LCDR2 of SEQ ID NO: 2; and
    (c) a LCDR3 of SEQ ID NO: 3.

2. The isolated polynucleotide of claim 1, wherein the polypeptide comprises a sequence selected from the group consisting of: SEQ ID NO: 13, SEQ ID NO: 14, SEQ ID NO: 15, SEQ ID NO: 16, SEQ ID NO: 22, SEQ ID NO: 23, and SEQ ID NO: 47.

3. The isolated polynucleotide of claim 2, wherein the polypeptide comprises SEQ ID NO: 14.

4. The isolated polynucleotide of claim 3, wherein the polynucleotide further comprises a nucleic acid sequence that encodes a polypeptide comprising SEQ ID NO: 11, and wherein the polynucleotide encodes a Fv fragment or scFv.

5. The isolated polynucleotide of claim 3, wherein the polynucleotide further comprises a nucleic acid sequence that encodes a polypeptide comprising SEQ ID NO: 12, and wherein the polynucleotide encodes a Fv fragment or scFv.

6. A vector comprising the polynucleotide of claim 3 and a polynucleotide comprising a nucleic acid sequence that encodes a polypeptide comprising SEQ ID NO: 11, wherein the vector encodes a Fv fragment or scFv.

7. An isolated host cell comprising the vector of claim 6.

8. A vector comprising the polynucleotide of claim 3 and a polynucleotide comprising a nucleic acid sequence that encodes a polypeptide comprising SEQ ID NO: 12, wherein the vector encodes a Fv fragment or scFv.

9. An isolated host cell comprising the vector of claim 8.

10. The isolated polynucleotide of claim 2, wherein the polypeptide comprises SEQ ID NO: 16.

11. The isolated polynucleotide of claim 2, wherein the polypeptide comprises SEQ ID NO: 47.

12. The isolated polynucleotide of claim 1, wherein the polynucleotide comprises a sequence selected from the group consisting of: SEQ ID NO: 36, SEQ ID NO: 37, SEQ ID NO: 38, and SEQ ID NO: 46.

13. The isolated polynucleotide of claim 12, wherein the polynucleotide comprises SEQ ID NO: 37.

14. The isolated polynucleotide of claim 13, wherein the polynucleotide further comprises SEQ ID NO: 34, and wherein the polynucleotide encodes a Fv fragment or scFv.

15. The isolated polynucleotide of claim 13, wherein the polynucleotide further comprises SEQ ID NO: 35, and wherein the polynucleotide encodes a Fv fragment or scFv.

16. A vector comprising the polynucleotide of claim 13 and a polynucleotide comprising a nucleic acid sequence comprising SEQ ID NO: 34, wherein the vector encodes a Fv fragment or scFv.

17. An isolated host cell comprising the vector of claim 16.

18. A vector comprising the polynucleotide of claim 13 and a polynucleotide comprising a nucleic acid sequence comprising SEQ ID NO: 35, wherein the vector encodes a Fv fragment or scFv.

19. An isolated host cell comprising the vector of claim 18.

20. The isolated polynucleotide of claim 12, wherein the polynucleotide comprises SEQ ID NO: 46.

21. The isolated polynucleotide of claim 1, wherein the polynucleotide further comprises a nucleic acid sequence that encodes a polypeptide comprising a heavy chain variable region, wherein the heavy chain variable region comprises:
 (a) a heavy chain complementary determining region 1 (HCDR1) of SEQ ID NO: 4;
 (b) a HCDR2 of SEQ ID NO: 5; and
 (c) a HCDR3 of SEQ ID NO: 6, and
 wherein the polynucleotide encodes a Fv fragment or single-chain Fv (scFv).

22. A vector comprising the polynucleotide of claim 1.

23. An isolated host cell comprising the vector of claim 22.

24. An isolated polynucleotide comprising a nucleic acid sequence that encodes a polypeptide comprising a heavy chain variable region of an antibody or antigen binding fragment that binds the $\alpha_v\beta_3$ integrin cysteine loop (C-loop) domain of SEQ ID NO: 29, wherein the polypeptide comprises a sequence selected from the group consisting of: SEQ ID NO: 7, SEQ ID NO: 8, SEQ ID NO: 9, SEQ ID NO: 10, SEQ ID NO: 11, SEQ ID NO: 12, SEQ ID NO: 17, SEQ ID NO: 24, SEQ ID NO: 25, SEQ ID NO: 26, SEQ ID NO: 27, SEQ ID NO: 28, and SEQ ID NO: 49.

25. The isolated polynucleotide of claim 24, wherein the polypeptide comprises SEQ ID NO: 11.

26. The isolated polynucleotide of claim 24, wherein the polypeptide comprises SEQ ID NO: 12.

27. The isolated polynucleotide of claim 24, wherein the polypeptide comprises SEQ ID NO: 28.

28. The isolated polynucleotide of claim 24, wherein the polypeptide comprises SEQ ID NO: 17.

29. The isolated polynucleotide of claim 24, wherein the polypeptide comprises SEQ ID NO: 49.

30. The isolated polynucleotide of claim 24, wherein the polynucleotide comprises a sequence selected from the group consisting of: SEQ ID NO: 30, SEQ ID NO: 31, SEQ ID NO: 32, SEQ ID NO: 33, SEQ ID NO: 34, SEQ ID NO: 35, and SEQ ID NO: 48.

31. The isolated polynucleotide of claim 30, wherein the polynucleotide comprises SEQ ID NO: 34.

32. The isolated polynucleotide of claim 30, wherein the polynucleotide comprises SEQ ID NO: 35.

33. The isolated polynucleotide of claim 30, wherein the polynucleotide comprises SEQ ID NO: 48.

34. A vector comprising the polynucleotide of claim 24.

35. An isolated host cell comprising the vector of claim 34.

* * * * *

SEQUENCE LISTING

```
<160> NUMBER OF SEQ ID NOS: 49

<210> SEQ ID NO 1
<211> LENGTH: 17
<212> TYPE: PRT
<213> ORGANISM: Artificial
<220> FEATURE:
<223> OTHER INFORMATION: Light chain complementarity determining region

<400> SEQUENCE: 1

Lys Ser Ser Gln Ser Leu Leu Tyr Ser Ser Asn Gln Lys Asn Tyr Leu
1               5                   10                  15
Ala

<210> SEQ ID NO 2
<211> LENGTH: 7
<212> TYPE: PRT
<213> ORGANISM: Artificial
<220> FEATURE:
<223> OTHER INFORMATION: Light chain complementarity determining region

<400> SEQUENCE: 2

Trp Ala Ser Thr Arg Glu Ser
1               5

<210> SEQ ID NO 3
<211> LENGTH: 9
<212> TYPE: PRT
<213> ORGANISM: Artificial
<220> FEATURE:
<223> OTHER INFORMATION: Light chain complementarity determining region

<400> SEQUENCE: 3

Lys Gln Tyr Tyr Thr Tyr Pro Leu Thr
1               5

<210> SEQ ID NO 4
<211> LENGTH: 5
<212> TYPE: PRT
<213> ORGANISM: Artificial
<220> FEATURE:
<223> OTHER INFORMATION: Heavy chain variable region sequence

<400> SEQUENCE: 4

Asn Ser Trp Met Asn
1               5

<210> SEQ ID NO 5
<211> LENGTH: 16
```

-continued

```
<212> TYPE: PRT
<213> ORGANISM: Artificial
<220> FEATURE:
<223> OTHER INFORMATION: Heavy chain variable region sequence

<400> SEQUENCE: 5

Ile Phe Pro Gly Asp Gly Asp Thr Asn Tyr Asn Gly Lys Phe Lys Gly
1               5                   10                  15

<210> SEQ ID NO 6
<211> LENGTH: 13
<212> TYPE: PRT
<213> ORGANISM: Artificial
<220> FEATURE:
<223> OTHER INFORMATION: Heavy chain complementarity determining region

<400> SEQUENCE: 6

Trp Gly Leu Thr Arg Asp Arg Arg Leu Tyr Leu Asp Tyr
1               5                   10

<210> SEQ ID NO 7
<211> LENGTH: 122
<212> TYPE: PRT
<213> ORGANISM: Artificial
<220> FEATURE:
<223> OTHER INFORMATION: Heavy chain variable region sequence

<400> SEQUENCE: 7

Gln Ala Gln Leu Val Gln Ser Gly Pro Glu Leu Lys Lys Pro Gly Ala
1               5                   10                  15

Ser Val Lys Val Ser Cys Lys Ala Ser Gly Tyr Leu Phe Ser Asn Ser
                20                  25                  30

Trp Met Asn Trp Val Lys Gln Arg Pro Gly Ala Gly Leu Glu Trp Ile
            35                  40                  45

Gly Arg Ile Phe Pro Gly Asp Gly Asp Thr Asn Tyr Asn Gly Lys Phe
        50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Ser Ala Val Tyr Phe Cys
                85                  90                  95

Ala Arg Trp Gly Leu Thr Arg Asp Arg Arg Leu Tyr Leu Asp Tyr Trp
            100                 105                 110

Gly Gln Gly Thr Thr Val Thr Val Ser Ser
        115                 120

<210> SEQ ID NO 8
<211> LENGTH: 122
<212> TYPE: PRT
<213> ORGANISM: Artificial
<220> FEATURE:
<223> OTHER INFORMATION: Heavy chain variable region sequence

<400> SEQUENCE: 8

Gln Ala Gln Leu Val Gln Ser Gly Pro Glu Val Lys Lys Pro Gly Ala
1               5                   10                  15

Ser Val Lys Val Ser Cys Lys Ala Ser Gly Tyr Leu Phe Ser Asn Ser
                20                  25                  30

Trp Met Asn Trp Val Lys Gln Arg Pro Gly Ala Gly Leu Glu Trp Ile
            35                  40                  45

Gly Arg Ile Phe Pro Gly Asp Gly Asp Thr Asn Tyr Asn Gly Lys Phe
        50                  55                  60
```

```
Lys Gly Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Trp Gly Leu Thr Arg Asp Arg Arg Leu Tyr Leu Asp Tyr Trp
                100                 105                 110

Gly Gln Gly Thr Thr Val Thr Val Ser Ser
            115                 120
```

<210> SEQ ID NO 9
<211> LENGTH: 122
<212> TYPE: PRT
<213> ORGANISM: Artificial
<220> FEATURE:
<223> OTHER INFORMATION: Heavy chain variable region sequence

<400> SEQUENCE: 9

```
Gln Ala Gln Leu Val Gln Ser Gly Ala Glu Val Lys Lys Pro Gly Ala
 1               5                  10                  15

Ser Val Lys Val Ser Cys Lys Ala Ser Gly Tyr Leu Phe Ser Asn Ser
                 20                  25                  30

Trp Met Asn Trp Val Lys Gln Arg Arg Gly Ala Gly Leu Glu Trp Ile
                 35                  40                  45

Gly Arg Ile Phe Pro Gly Asp Gly Asp Thr Asn Tyr Asn Gly Lys Phe
         50                  55                  60

Lys Gly Arg Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Trp Gly Leu Thr Arg Asp Arg Arg Leu Tyr Leu Asp Tyr Trp
                100                 105                 110

Gly Gln Gly Thr Thr Val Thr Val Ser Ser
            115                 120
```

<210> SEQ ID NO 10
<211> LENGTH: 122
<212> TYPE: PRT
<213> ORGANISM: Artificial
<220> FEATURE:
<223> OTHER INFORMATION: Heavy chain variable region sequence

<400> SEQUENCE: 10

```
Gln Ala Gln Leu Val Gln Ser Gly Ala Glu Val Lys Lys Pro Gly Ala
 1               5                  10                  15

Ser Val Lys Val Ser Cys Lys Ala Ser Gly Tyr Leu Phe Ser Asn Ser
                 20                  25                  30

Trp Met Asn Trp Val Lys Gln Arg Arg Gly Ala Gly Leu Glu Trp Ile
                 35                  40                  45

Gly Arg Ile Phe Pro Gly Asp Gly Asp Thr Asn Tyr Asn Gly Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Trp Gly Leu Thr Arg Asp Arg Arg Leu Tyr Leu Asp Tyr Trp
                100                 105                 110

Gly Gln Gly Thr Thr Val Thr Val Ser Ser
            115                 120
```

<210> SEQ ID NO 11
<211> LENGTH: 122
<212> TYPE: PRT
<213> ORGANISM: Artificial
<220> FEATURE:
<223> OTHER INFORMATION: Heavy chain variable region sequence

<400> SEQUENCE: 11

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Arg Gly Ala Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Thr Arg Asp Arg Arg Leu Tyr Leu Asp Tyr Trp
            100                 105                 110

Gly Gln Gly Thr Thr Val Thr Val Ser Ser
            115                 120

<210> SEQ ID NO 12
<211> LENGTH: 122
<212> TYPE: PRT
<213> ORGANISM: Artificial
<220> FEATURE:
<223> OTHER INFORMATION: Heavy chain variable region sequence

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Arg Gly Ala Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Leu Thr Arg Asp Arg Arg Leu Tyr Leu Asp Tyr Trp
            100                 105                 110

Gly Gln Gly Thr Thr Val Thr Val Ser Ser
            115                 120

<210> SEQ ID NO 13
<211> LENGTH: 113
<212> TYPE: PRT
<213> ORGANISM: Artificial
<220> FEATURE:
<223> OTHER INFORMATION: Light chain variable region sequence

<400> SEQUENCE: 13

-continued

Asp Ile Val Met Thr Gln Ser Pro Asp Ser Leu Val Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Ser Gly Gln
        35                  40                  45

Ala Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Tyr Tyr Thr Tyr Pro Leu Thr Phe Gly Gln Gly Thr Lys Leu Glu Ile
                100                 105                 110

Lys

<210> SEQ ID NO 14
<211> LENGTH: 113
<212> TYPE: PRT
<213> ORGANISM: Artificial
<220> FEATURE:
<223> OTHER INFORMATION: Light chain variable region sequence

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Tyr Tyr Thr Tyr Pro Leu Thr Phe Gly Gln Gly Thr Lys Leu Glu Ile
                100                 105                 110

Lys

<210> SEQ ID NO 15
<211> LENGTH: 113
<212> TYPE: PRT
<213> ORGANISM: Artificial
<220> FEATURE:
<223> OTHER INFORMATION: Light chain variable region sequence

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
                65                  70                  75                  80
Ile Ser Ser Leu Gln Ala Glu Asp Val Ala Val Tyr Tyr Cys Lys Gln
                    85                  90                  95
Tyr Tyr Thr Tyr Pro Leu Thr Phe Gly Gln Gly Thr Lys Leu Glu Ile
                    100                 105                 110
Lys
```

<210> SEQ ID NO 16
<211> LENGTH: 220
<212> TYPE: PRT
<213> ORGANISM: Artificial
<220> FEATURE:
<223> OTHER INFORMATION: Light chain sequence

<400> SEQUENCE: 16

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Ser
                    20                  25                  30
Ser Asn Gln Lys Asn Tyr Leu Ala Trp Tyr Gln Gln Lys Pro Gly Gln
                    35                  40                  45
Ala Pro Arg Leu Leu Ile Tyr Trp Ala Ser Thr Arg Glu Ser Gly Val
                50                  55                  60
Pro Asp Arg Phe Thr Gly Ser Gly Ser Gly Thr Asp Phe Thr Leu Thr
65                  70                  75                  80
Ile Ser Ser Leu Gln Ala Glu Asp Val Ala Val Tyr Tyr Cys Lys Gln
                    85                  90                  95
Tyr Tyr Thr Tyr Pro Leu Thr Phe Gly Gln Gly Thr Lys Leu Glu Ile
                    100                 105                 110
Lys Arg Thr Val Ala Ala Pro Ser Val Phe Ile Phe Pro Pro Ser Asp
                    115                 120                 125
Glu Gln Leu Lys Ser Gly Thr Ala Ser Val Val Cys Leu Leu Asn Asn
                130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                    165                 170                 175
Ser Thr Tyr Ser Leu Ser Ser Thr Leu Thr Leu Ser Lys Ala Asp Tyr
                    180                 185                 190
Glu Lys His Lys Val Tyr Ala Cys Glu Val Thr His Gln Gly Leu Ser
                    195                 200                 205
Ser Pro Val Thr Lys Ser Phe Asn Arg Gly Glu Cys
                210                 215                 220
```

<210> SEQ ID NO 17
<211> LENGTH: 452
<212> TYPE: PRT
<213> ORGANISM: Artificial
<220> FEATURE:
<223> OTHER INFORMATION: Heavy chain sequence

<400> SEQUENCE: 17

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Leu Phe Ser Asn Ser
                    20                  25                  30
Trp Met Asn Trp Val Lys Gln Arg Arg Gly Ala Gly Leu Glu Trp Ile
```

```
            35                  40                  45
Gly Arg Ile Phe Pro Gly Asp Gly Asp Thr Asn Tyr Asn Gly Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Trp Gly Leu Thr Arg Asp Arg Arg Leu Tyr Leu Asp Tyr Trp
            100                 105                 110
Gly Gln Gly Thr Thr Val Thr Val Ser Ser Ala Ser Thr Lys Gly Pro
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                 245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                 325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                 405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
            450
```

<210> SEQ ID NO 18
<211> LENGTH: 113
<212> TYPE: PRT
<213> ORGANISM: Artificial
<220> FEATURE:
<223> OTHER INFORMATION: Light chain variable region sequence

<400> SEQUENCE: 18

Asp Ile Val Met Ser Gln Ser Pro Ser Ser Leu Val Val Ser Val Gly
1               5                   10                  15

Glu Lys Val Thr Met Ser Cys Lys Ser Gln Ser Leu Leu Tyr Ser
            20                  25                  30

Ser Asn Gln Lys Asn Tyr Leu Ala Trp Tyr Gln Gln Lys Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Lys Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 19
<211> LENGTH: 113
<212> TYPE: PRT
<213> ORGANISM: Artificial
<220> FEATURE:
<223> OTHER INFORMATION: Light chain variable region sequence
<220> FEATURE:
<221> NAME/KEY: MISC_FEATURE
<222> LOCATION: (5)..(5)
<223> OTHER INFORMATION: Xaa can be S or T
<220> FEATURE:
<221> NAME/KEY: MISC_FEATURE
<222> LOCATION: (9)..(9)
<223> OTHER INFORMATION: Xaa can be S or D
<220> FEATURE:
<221> NAME/KEY: MISC_FEATURE
<222> LOCATION: (12)..(12)
<223> OTHER INFORMATION: Xaa can be V or A
<220> FEATURE:
<221> NAME/KEY: MISC_FEATURE
<222> LOCATION: (15)..(15)
<223> OTHER INFORMATION: Xaa can be V or L
<220> FEATURE:
<221> NAME/KEY: MISC_FEATURE
<222> LOCATION: (18)..(18)
<223> OTHER INFORMATION: Xaa can be K or R
<220> FEATURE:
<221> NAME/KEY: MISC_FEATURE
<222> LOCATION: (19)..(19)
<223> OTHER INFORMATION: Xaa can be V or A
<220> FEATURE:
<221> NAME/KEY: MISC_FEATURE
<222> LOCATION: (21)..(21)
<223> OTHER INFORMATION: Xaa can be M or I
<220> FEATURE:
<221> NAME/KEY: MISC_FEATURE
<222> LOCATION: (22)..(22)
<223> OTHER INFORMATION: Xaa can be S or N
<220> FEATURE:
<221> NAME/KEY: MISC_FEATURE
<222> LOCATION: (46)..(46)
<223> OTHER INFORMATION: Xaa can be S or P
<220> FEATURE:
<221> NAME/KEY: MISC_FEATURE
<222> LOCATION: (49)..(49)
<223> OTHER INFORMATION: Xaa can be S or A
<220> FEATURE:
<221> NAME/KEY: MISC_FEATURE
<222> LOCATION: (51)..(51)
<223> OTHER INFORMATION: Xaa can be K or R
<220> FEATURE:
<221> NAME/KEY: MISC_FEATURE
<222> LOCATION: (84)..(84)
<223> OTHER INFORMATION: Xaa can be V or L
<220> FEATURE:
<221> NAME/KEY: MISC_FEATURE
<222> LOCATION: (85)..(85)
<223> OTHER INFORMATION: Xaa can be K or Q
<220> FEATURE:
<221> NAME/KEY: MISC_FEATURE
<222> LOCATION: (89)..(89)
<223> OTHER INFORMATION: Xaa can be L or V
<220> FEATURE:
<221> NAME/KEY: MISC_FEATURE
<222> LOCATION: (99)..(99)
<223> OTHER INFORMATION: Xaa can be S or T
<220> FEATURE:
<221> NAME/KEY: MISC_FEATURE
<222> LOCATION: (106)..(106)
<223> OTHER INFORMATION: Xaa can be A or Q
<220> FEATURE:
<221> NAME/KEY: MISC_FEATURE
<222> LOCATION: (112)..(112)
<223> OTHER INFORMATION: Xaa can be L or I

<400> SEQUENCE: 19

Asp Ile Val Met Xaa Gln Ser Pro Xaa Ser Leu Xaa Val Ser Xaa Gly
1               5                   10                  15

Glu Xaa Xaa Thr Xaa Xaa Cys Lys Ser Ser Gln Ser Leu Leu Tyr Ser
            20                  25                  30

Ser Asn Gln Lys Asn Tyr Leu Ala Trp Tyr Gln Gln Lys Xaa Gly Gln
        35                  40                  45

Xaa Pro Xaa Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Lys Gln
                85                  90                  95

Tyr Tyr Xaa Tyr Pro Leu Thr Phe Gly Xaa Gly Thr Lys Leu Glu Xaa
            100                 105                 110

Lys

<210> SEQ ID NO 20
<211> LENGTH: 122
<212> TYPE: PRT
<213> ORGANISM: Artificial
<220> FEATURE:
<223> OTHER INFORMATION: Heavy chain variable region sequence

<400> SEQUENCE: 20

Gln Ala Gln Leu Gln Gln Ser Gly Pro Glu Leu Val Lys Pro Gly Ala
1               5                   10                  15

Ser Val Glu Ile Ser Cys Lys Ala Ser Gly Tyr Leu Phe Ser Asn Ser
            20                  25                  30

Trp Met Asn Trp Val Lys Gln Arg Pro Gly Lys Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr

```
                65                  70                  75                  80
Met Gln Leu Asn Ser Leu Thr Ser Glu Asp Ser Ala Val Tyr Phe Cys
                    85                  90                  95

Ala Arg Trp Gly Leu Thr Arg Asp Arg Arg Leu Tyr Leu Asp Tyr Trp
                100                 105                 110

Gly Gln Gly Thr Thr Leu Thr Val Ser Ser
        115                 120
```

```
<210> SEQ ID NO 21
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (2)..(2)
<223> OTHER INFORMATION: Xaa can be A or V
<220> FEATURE:
<221> NAME/KEY: MISC_FEATURE
<222> LOCATION: (5)..(5)
<223> OTHER INFORMATION: Xaa can be Q or V
<220> FEATURE:
<221> NAME/KEY: MISC_FEATURE
<222> LOCATION: (9)..(9)
<223> OTHER INFORMATION: Xaa can be P or A
<220> FEATURE:
<221> NAME/KEY: MISC_FEATURE
<222> LOCATION: (11)..(11)
<223> OTHER INFORMATION: Xaa can be L or V
<220> FEATURE:
<221> NAME/KEY: MISC_FEATURE
<222> LOCATION: (12)..(12)
<223> OTHER INFORMATION: Xaa can be V or K
<220> FEATURE:
<221> NAME/KEY: MISC_FEATURE
<222> LOCATION: (19)..(19)
<223> OTHER INFORMATION: Xaa can be E or K
<220> FEATURE:
<221> NAME/KEY: MISC_FEATURE
<222> LOCATION: (20)..(20)
<223> OTHER INFORMATION: Xaa can be I or V
<220> FEATURE:
<221> NAME/KEY: MISC_FEATURE
<222> LOCATION: (41)..(41)
<223> OTHER INFORMATION: Xaa can be P or R
<220> FEATURE:
<221> NAME/KEY: MISC_FEATURE
<222> LOCATION: (43)..(43)
<223> OTHER INFORMATION: Xaa can be K or A
<220> FEATURE:
<221> NAME/KEY: MISC_FEATURE
<222> LOCATION: (67)..(67)
<223> OTHER INFORMATION: Xaa can be K or R
<220> FEATURE:
<221> NAME/KEY: MISC_FEATURE
<222> LOCATION: (68)..(68)
<223> OTHER INFORMATION: Xaa can be A to V
<220> FEATURE:
<221> NAME/KEY: MISC_FEATURE
<222> LOCATION: (70)..(70)
<223> OTHER INFORMATION: Xaa can be L or I
<220> FEATURE:
<221> NAME/KEY: MISC_FEATURE
<222> LOCATION: (76)..(76)
<223> OTHER INFORMATION: Xaa can be S or T
<220> FEATURE:
<221> NAME/KEY: MISC_FEATURE
<222> LOCATION: (82)..(82)
<223> OTHER INFORMATION: Xaa can be Q or E
<220> FEATURE:
<221> NAME/KEY: MISC_FEATURE
<222> LOCATION: (84)..(84)
<223> OTHER INFORMATION: Xaa can be N or S
<220> FEATURE:
```

```
<221> NAME/KEY: MISC_FEATURE
<222> LOCATION: (87)..(87)
<223> OTHER INFORMATION: Xaa can be T or R
<220> FEATURE:
<221> NAME/KEY: MISC_FEATURE
<222> LOCATION: (91)..(91)
<223> OTHER INFORMATION: Xaa can be S or T
<220> FEATURE:
<221> NAME/KEY: MISC_FEATURE
<222> LOCATION: (95)..(95)
<223> OTHER INFORMATION: Xaa can be F or Y
<220> FEATURE:
<221> NAME/KEY: MISC_FEATURE
<222> LOCATION: (118)..(118)
<223> OTHER INFORMATION: Xaa can be L or V

<400> SEQUENCE: 21

Gln Xaa Gln Leu Xaa Gln Ser Gly Xaa Glu Xaa Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Xaa Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Xaa Thr Xaa Thr Ala Asp Lys Ser Xaa Ser Thr Ala Tyr
65                  70                  75                  80

Met Xaa Leu Xaa Ser Leu Xaa Ser Glu Asp Xaa Ala Val Tyr Xaa Cys
            85                  90                  95

Ala Arg Trp Gly Leu Thr Arg Asp Arg Arg Leu Tyr Leu Asp Tyr Trp
            100                 105                 110

Gly Gln Gly Thr Thr Xaa Thr Val Ser Ser
        115                 120

<210> SEQ ID NO 22
<211> LENGTH: 220
<212> TYPE: PRT
<213> ORGANISM: Artificial
<220> FEATURE:
<223> OTHER INFORMATION: Light chain sequence

<400> SEQUENCE: 22

Asp Ile Val Met Thr Gln Ser Pro Asp Ser Leu Val Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Ser Gly Gln
        35                  40                  45

Ala Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
            85                  90                  95

Tyr Tyr Thr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140
```

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 23
<211> LENGTH: 220
<212> TYPE: PRT
<213> ORGANISM: Artificial
<220> FEATURE:
<223> OTHER INFORMATION: Light chain sequence

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Tyr Tyr Thr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 24
<211> LENGTH: 452
<212> TYPE: PRT
<213> ORGANISM: Artificial
<220> FEATURE:
<223> OTHER INFORMATION: Heavy chain sequence

<400> SEQUENCE: 24

Gln Ala Gln Leu Val Gln Ser Gly Pro Glu Leu Lys Lys Pro Gly Ala
1               5                   10                  15

```
Ser Val Lys Val Ser Cys Lys Ala Ser Gly Tyr Leu Phe Ser Asn Ser
            20                  25                  30
Trp Met Asn Trp Val Lys Gln Arg Pro Gly Ala Gly Leu Glu Trp Ile
        35                  40                  45
Gly Arg Ile Phe Pro Gly Asp Gly Asp Thr Asn Tyr Asn Gly Lys Phe
    50                  55                  60
Lys Gly Arg Ala Thr Ile Thr Ala Asp Lys Ser Thr Ser Thr Ala Tyr
65                  70                  75                  80
Met Glu Leu Ser Ser Leu Arg Ser Glu Asp Ser Ala Val Tyr Phe Cys
                85                  90                  95
Ala Arg Trp Gly Leu Thr Arg Asp Arg Arg Leu Tyr Leu Asp Tyr Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
```

Met His Glu Ala Leu His Asn His Tyr Thr Gln Lys Ser Leu Ser Leu
            435                 440                 445

Ser Pro Gly Lys
    450

<210> SEQ ID NO 25
<211> LENGTH: 452
<212> TYPE: PRT
<213> ORGANISM: Artificial
<220> FEATURE:
<223> OTHER INFORMATION: Heavy chain sequence

<400> SEQUENCE: 25

Gln Ala Gln Leu Val Gln Ser Gly Pro Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Pro Gly Ala Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Trp Gly Leu Thr Arg Asp Arg Arg Leu Tyr Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

```
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 26
<211> LENGTH: 452
<212> TYPE: PRT
<213> ORGANISM: Artificial
<220> FEATURE:
<223> OTHER INFORMATION: Heavy chain sequence

<400> SEQUENCE: 26

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Arg Gly Ala Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Trp Gly Leu Thr Arg Asp Arg Arg Leu Tyr Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 27
<211> LENGTH: 452
<212> TYPE: PRT
<213> ORGANISM: Artificial
<220> FEATURE:
<223> OTHER INFORMATION: Heavy chain sequence

<400> SEQUENCE: 27

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Gly Ala Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
            85                  90                  95

Ala Arg Trp Gly Leu Thr Arg Asp Arg Arg Leu Tyr Leu Asp Tyr Trp
        100                 105                 110

Gly Gln Gly Thr Thr Val Thr Val Ser Ser Ala Ser Thr Lys Gly Pro
    115                 120                 125

Ser Val Phe Pro Leu Ala Pro Ser Ser Lys Ser Thr Ser Gly Gly Thr
    130                 135                 140

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 28
<211> LENGTH: 452
<212> TYPE: PRT
<213> ORGANISM: Artificial
<220> FEATURE:
<223> OTHER INFORMATION: Heavy chain sequence

<400> SEQUENCE: 28

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Leu Phe Ser Asn Ser
            20                  25                  30

Trp Met Asn Trp Val Lys Gln Arg Arg Gly Ala Gly Leu Glu Trp Ile
        35                  40                  45
```

```
Gly Arg Ile Phe Pro Gly Asp Gly Asp Thr Asn Tyr Asn Gly Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Gly Leu Thr Arg Asp Arg Arg Leu Tyr Leu Asp Tyr Trp
             100                 105                 110

Gly Gln Gly Thr Thr Val Thr Val Ser Ser Ala Ser Thr Lys Gly Pro
         115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
 145             150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Lys Val Glu Pro Lys Ser
 210                 215                 220

Cys Asp Lys Thr His Thr Cys Pro Pro Cys Pro Ala Pro Glu Leu Leu
 225             230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
 290                 295                 300

Tyr Arg Val Val Ser Val Leu Thr Val Leu His Gln Asp Trp Leu Asn
 305             310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Asp Glu Leu Thr Lys Asn Gln Val
         355                 360                 365

Ser Leu Thr Cys Leu Val Lys Gly Phe Tyr Pro Ser Asp Ile Ala Val
 370                 375                 380

Glu Trp Glu Ser Asn Gly Gln Pro Glu Asn Asn Tyr Lys Thr Thr Pro
 385             390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
         435                 440                 445

Ser Pro Gly Lys
 450
```

```
<210> SEQ ID NO 29
<211> LENGTH: 8
<212> TYPE: PRT
<213> ORGANISM: Artificial
<220> FEATURE:
<223> OTHER INFORMATION: Cysteine loop peptide sequence

<400> SEQUENCE: 29

Cys Tyr Asp Met Lys Thr Thr Cys
1               5

<210> SEQ ID NO 30
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 30
caggctcagc tggtgcagtc tggacctgag ctgaagaagc ctggggcctc agtgaaggtt     60
tcctgcaagg cttctggcta tttattcagt aactcctgga tgaactgggt gaaacagagg    120
cctggagcgg tcttgagtg gattggacgg attttcctg gagatggaga tactaactac     180
aatgggaagt tcaagggccg ggccacaatc actgcagaca atccaccag cacagcctac    240 atggaactca gcagcctgag atctgaggac tctgcggtct atttctgtgc aagatgggga    300
cttaccaggg accgaagact ttaccttgac tattgggggcc aaggcaccac tgtcacagtc    360
tcctca                                                               366

<210> SEQ ID NO 31
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 31
caggctcagc tggtgcagtc tggacctgag gtgaagaagc ctggggcctc agtgaaggtt     60
tcctgcaagg cttctggcta tttattcagt aactcctgga tgaactgggt gaaacagagg    120
cctggagcgg tcttgagtg gattggacgg attttcctg gagatggaga tactaactac     180
aatgggaagt tcaagggccg ggccacaatc actgcagaca atccaccag cacagcctac    240 atggaactca gcagcctgag atctgaggac actgcggtct atttctgtgc aagatgggga    300
cttaccaggg accgaagact ttaccttgac tattgggggcc aaggcaccac tgtcacagtc    360
tcctca                                                               366

<210> SEQ ID NO 32
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 32
caggctcagc tggtgcagtc tggagctgag gtgaagaagc ctggggcctc agtgaaggtt     60
tcctgcaagg cttctggcta tttattcagt aactcctgga tgaactgggt gaaacagagg    120
cgtggagcgg tcttgagtg gattggacgg attttcctg gagatggaga tactaactac     180
aatgggaagt tcaagggccg ggccacaatc actgcagaca atccaccag cacagcctac    240 atggaactca gcagcctgag atctgaggac actgcggtct atttctgtgc aagatgggga    300
```

```
cttaccaggg accgaagact ttaccttgac tattggggcc aaggcaccac tgtcacagtc    360
tcctca                                                               366

<210> SEQ ID NO 33
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 33
caggctcagc tggtgcagtc tggagctgag gtgaagaagc ctggggcctc agtgaaggtt    60
tcctgcaagg cttctggcta tttattcagt aactcctgga tgaactgggt gaaacagagg   120
cgtggagcgg gtcttgagtg gattggacgg attttcctg gagatggaga tactaactac    180
aatgggaagt tcaagggccg ggtcacaatc actgcagaca atccaccag cacagcctac    240 atggaactca gcagcctgag atctgaggac actgcggtct atttctgtgc aagatgggga   300
cttaccaggg accgaagact ttaccttgac tattggggcc aaggcaccac tgtcacagtc   360
tcctca                                                               366

<210> SEQ ID NO 34
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 34
caggctcagc tggtgcagtc tggagctgag gtgaagaagc ctggggcctc agtgaaggtt    60
tcctgcaagg cttctggcta tttattcagt aactcctgga tgaactgggt gaaacagagg   120
cgtggagcgg gtcttgagtg gattggacgg attttcctg gagatggaga tactaactac    180
aatgggaagt tcaagggccg ggtcacaatc actgcagaca atccaccag cacagcctac    240 atggaactca gcagcctgag atctgaggac actgcggtct attactgtgc aagatgggga   300
cttaccaggg accgaagact ttaccttgac tattggggcc aaggcaccac tgtcacagtc   360
tcctca                                                               366

<210> SEQ ID NO 35
<211> LENGTH: 366
<212> TYPE: DNA
<213> ORGANISM: Artificial
<220> FEATURE:
<223> OTHER INFORMATION: Heavy chain variable region coding sequence

<400> SEQUENCE: 35
caggtgcagc tggtgcagtc tggagctgag gtgaagaagc ctgggcctc agtgaaggtt     60 tcctgcaagg cttctggcta tttattcagt aactcctgga tgaactgggt gaaacagagg   120
cgtggagcgg gtcttgagtg gattggacgg attttcctg gagatggaga tactaactac    180
aatgggaagt tcaagggccg ggtcacaatc actgcagaca atccaccag cacagcctac    240 atggaactca gcagcctgag atctgaggac actgcggtct attactgtgc aagatgggga   300
cttaccaggg accgaagact ttaccttgac tattggggcc aaggcaccac tgtcacagtc   360
tcctca                                                               366

<210> SEQ ID NO 36
```

```
<211> LENGTH: 339
<212> TYPE: DNA
<213> ORGANISM: Artificial
<220> FEATURE:
<223> OTHER INFORMATION: Light chain variable region coding sequence

<400> SEQUENCE: 36
gacattgtga tgacacagtc tccagattcc ctagttgtgt cacttggaga gagggcaact    60
attaactgca agtccagtca gagccttttta tatagtagca atcaaaagaa ctatttggcc   120
tggtaccagc agaaatcagg gcaggctcct agactgctga tttactgggc atccactagg   180
gaatctgggg tccctgatcg cttcacaggc agtggatctg gacagattt cactctcacc    240 atcagcagtc tgcaggctga agacgtggca gtttattact gtaagcagta ttatacgtat   300
cctctcacgt tcggtcaggg gaccaagctg gagattaaa                          339

<210> SEQ ID NO 37
<211> LENGTH: 339
<212> TYPE: DNA
<213> ORGANISM: Artificial
<220> FEATURE:
<223> OTHER INFORMATION: Light chain variable region coding sequence

<400> SEQUENCE: 37
gacattgtga tgacacagtc tccagattcc ctagctgtgt cacttggaga gagggcaact    60
attaactgca agtccagtca gagccttttta tatagtagca atcaaaagaa ctatttggcc   120
tggtaccagc agaaaccagg gcaggctcct agactgctga tttactgggc atccactagg   180
gaatctgggg tccctgatcg cttcacaggc agtggatctg gacagattt cactctcacc    240 atcagcagtc tgcaggctga agacgtggca gtttattact gtaagcagta ttatacgtat   300
cctctcacgt tcggtcaggg gaccaagctg gagattaaa                          339

<210> SEQ ID NO 38
<211> LENGTH: 339
<212> TYPE: DNA
<213> ORGANISM: Artificial
<220> FEATURE:
<223> OTHER INFORMATION: Light chain variable region coding sequence

<400> SEQUENCE: 38
gacattgtga tgacacagtc tccagattcc ctagctgtgt cacttggaga gagggcaact    60
attaactgca agtccagtca gagccttttta tatagtagca atcaaaagaa ctatttggcc   120
tggtaccagc agaaaccagg gcaggctcct agactgctga tttactgggc atccactagg   180
gaatctgggg tccctgatcg cttctcaggc agtggatctg gacagattt cactctcacc    240 atcagcagtc tgcaggctga agacgtggca gtttattact gtaagcagta ttatacgtat   300
cctctcacgt tcggtcaggg gaccaagctg gagattaaa                          339

<210> SEQ ID NO 39
<211> LENGTH: 113
<212> TYPE: PRT
<213> ORGANISM: Artificial
<220> FEATURE:
<223> OTHER INFORMATION: Light chain variable region sequence
<220> FEATURE:
<221> NAME/KEY: MISC_FEATURE
<222> LOCATION: (5)..(5)
<223> OTHER INFORMATION: Xaa may be S or T
<220> FEATURE:
<221> NAME/KEY: MISC_FEATURE
<222> LOCATION: (9)..(9)
<223> OTHER INFORMATION: Xaa may be S or D
```

```
<220> FEATURE:
<221> NAME/KEY: MISC_FEATURE
<222> LOCATION: (15)..(15)
<223> OTHER INFORMATION: Xaa may be V or L
<220> FEATURE:
<221> NAME/KEY: MISC_FEATURE
<222> LOCATION: (18)..(18)
<223> OTHER INFORMATION: Xaa may be K or R
<220> FEATURE:
<221> NAME/KEY: MISC_FEATURE
<222> LOCATION: (19)..(19)
<223> OTHER INFORMATION: Xaa may be V or A
<220> FEATURE:
<221> NAME/KEY: MISC_FEATURE
<222> LOCATION: (21)..(21)
<223> OTHER INFORMATION: Xaa may be M or I
<220> FEATURE:
<221> NAME/KEY: MISC_FEATURE
<222> LOCATION: (22)..(22)
<223> OTHER INFORMATION: Xaa may be S or N
<220> FEATURE:
<221> NAME/KEY: MISC_FEATURE
<222> LOCATION: (49)..(49)
<223> OTHER INFORMATION: Xaa may be S or A
<220> FEATURE:
<221> NAME/KEY: MISC_FEATURE
<222> LOCATION: (51)..(51)
<223> OTHER INFORMATION: Xaa may be K or R
<220> FEATURE:
<221> NAME/KEY: MISC_FEATURE
<222> LOCATION: (84)..(84)
<223> OTHER INFORMATION: Xaa may be V or L
<220> FEATURE:
<221> NAME/KEY: MISC_FEATURE
<222> LOCATION: (85)..(85)
<223> OTHER INFORMATION: Xaa may be K or Q
<220> FEATURE:
<221> NAME/KEY: MISC_FEATURE
<222> LOCATION: (89)..(89)
<223> OTHER INFORMATION: Xaa may be L or V
<220> FEATURE:
<221> NAME/KEY: MISC_FEATURE
<222> LOCATION: (99)..(99)
<223> OTHER INFORMATION: Xaa may be S or T
<220> FEATURE:
<221> NAME/KEY: MISC_FEATURE
<222> LOCATION: (106)..(106)
<223> OTHER INFORMATION: Xaa may be A to Q
<220> FEATURE:
<221> NAME/KEY: MISC_FEATURE
<222> LOCATION: (112)..(112)
<223> OTHER INFORMATION: Xaa may be L to I

<400> SEQUENCE: 39

Asp Ile Val Met Xaa Gln Ser Pro Xaa Ser Leu Val Val Ser Xaa Gly
1               5                   10                  15

Glu Xaa Xaa Thr Xaa Xaa Cys Lys Ser Ser Gln Ser Leu Leu Tyr Ser
            20                  25                  30

Ser Asn Gln Lys Asn Tyr Leu Ala Trp Tyr Gln Gln Lys Ser Gly Gln
        35                  40                  45

Xaa Pro Xaa Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Lys Gln
                85                  90                  95

Tyr Tyr Xaa Tyr Pro Leu Thr Phe Gly Xaa Gly Thr Lys Leu Glu Xaa
            100                 105                 110

Lys
```

```
<210> SEQ ID NO 40
<211> LENGTH: 113
<212> TYPE: PRT
<213> ORGANISM: Artificial
<220> FEATURE:
<223> OTHER INFORMATION: Light chain variable region sequence
<220> FEATURE:
<221> NAME/KEY: MISC_FEATURE
<222> LOCATION: (5)..(5)
<223> OTHER INFORMATION: Xaa may be S or T
<220> FEATURE:
<221> NAME/KEY: MISC_FEATURE
<222> LOCATION: (9)..(9)
<223> OTHER INFORMATION: Xaa may be S or D
<220> FEATURE:
<221> NAME/KEY: MISC_FEATURE
<222> LOCATION: (12)..(12)
<223> OTHER INFORMATION: Xaa may be V or A
<220> FEATURE:
<221> NAME/KEY: MISC_FEATURE
<222> LOCATION: (15)..(15)
<223> OTHER INFORMATION: Xaa may be V or L
<220> FEATURE:
<221> NAME/KEY: MISC_FEATURE
<222> LOCATION: (18)..(18)
<223> OTHER INFORMATION: Xaa may be K or R
<220> FEATURE:
<221> NAME/KEY: MISC_FEATURE
<222> LOCATION: (19)..(19)
<223> OTHER INFORMATION: Xaa may be V or A
<220> FEATURE:
<221> NAME/KEY: MISC_FEATURE
<222> LOCATION: (21)..(21)
<223> OTHER INFORMATION: Xaa may be M or I
<220> FEATURE:
<221> NAME/KEY: MISC_FEATURE
<222> LOCATION: (22)..(22)
<223> OTHER INFORMATION: Xaa may be S to N
<220> FEATURE:
<221> NAME/KEY: MISC_FEATURE
<222> LOCATION: (46)..(46)
<223> OTHER INFORMATION: Xaa may be S or P
<220> FEATURE:
<221> NAME/KEY: MISC_FEATURE
<222> LOCATION: (49)..(49)
<223> OTHER INFORMATION: Xaa may be S or A
<220> FEATURE:
<221> NAME/KEY: MISC_FEATURE
<222> LOCATION: (51)..(51)
<223> OTHER INFORMATION: Xaa may be K to R
<220> FEATURE:
<221> NAME/KEY: MISC_FEATURE
<222> LOCATION: (69)..(69)
<223> OTHER INFORMATION: Xaa may be T or S
<220> FEATURE:
<221> NAME/KEY: MISC_FEATURE
<222> LOCATION: (84)..(84)
<223> OTHER INFORMATION: Xaa may be V to L
<220> FEATURE:
<221> NAME/KEY: MISC_FEATURE
<222> LOCATION: (85)..(85)
<223> OTHER INFORMATION: Xaa may be K or Q
<220> FEATURE:
<221> NAME/KEY: MISC_FEATURE
<222> LOCATION: (89)..(89)
<223> OTHER INFORMATION: Xaa may be L or V
<220> FEATURE:
<221> NAME/KEY: MISC_FEATURE
<222> LOCATION: (99)..(99)
<223> OTHER INFORMATION: Xaa may be S or T
<220> FEATURE:
<221> NAME/KEY: MISC_FEATURE
<222> LOCATION: (106)..(106)
<223> OTHER INFORMATION: Xaa may be A or Q
<220> FEATURE:
<221> NAME/KEY: MISC_FEATURE
<222> LOCATION: (112)..(112)
<223> OTHER INFORMATION: Xaa may be L or I
```

-continued

```
<400> SEQUENCE: 40

Asp Ile Val Met Xaa Gln Ser Pro Xaa Ser Leu Xaa Val Ser Xaa Gly
1               5                   10                  15

Glu Xaa Xaa Thr Xaa Xaa Cys Lys Ser Ser Gln Ser Leu Leu Tyr Ser
            20                  25                  30

Ser Asn Gln Lys Asn Tyr Leu Ala Trp Tyr Gln Gln Lys Xaa Gly Gln
        35                  40                  45

Xaa Pro Xaa Leu Leu Ile Tyr Trp Ala Ser Thr Arg Glu Ser Gly Val
    50                  55                  60

Pro Asp Arg Phe Xaa Gly Ser Gly Ser Gly Thr Asp Phe Thr Leu Thr
65                  70                  75                  80

Ile Ser Ser Xaa Xaa Ala Glu Asp Xaa Ala Val Tyr Tyr Cys Lys Gln
                85                  90                  95

Tyr Tyr Xaa Tyr Pro Leu Thr Phe Gly Xaa Gly Thr Lys Leu Glu Xaa
            100                 105                 110

Lys

<210> SEQ ID NO 41
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (5)..(5)
<223> OTHER INFORMATION: Xaa may be Q or V
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (19)..(19)
<223> OTHER INFORMATION: Xaa may be E or K
<220> FEATURE:
<221> NAME/KEY: MISC_FEATURE
<222> LOCATION: (20)..(20)
<223> OTHER INFORMATION: Xaa may be I or V
<220> FEATURE:
<221> NAME/KEY: MISC_FEATURE
<222> LOCATION: (43)..(43)
<223> OTHER INFORMATION: Xaa may be K or A
<220> FEATURE:
<221> NAME/KEY: MISC_FEATURE
<222> LOCATION: (67)..(67)
<223> OTHER INFORMATION: Xaa may be K or R
<220> FEATURE:
<221> NAME/KEY: MISC_FEATURE
<222> LOCATION: (70)..(70)
<223> OTHER INFORMATION: Xaa may be L or I
<220> FEATURE:
<221> NAME/KEY: MISC_FEATURE
<222> LOCATION: (76)..(76)
<223> OTHER INFORMATION: Xaa may be S or T
<220> FEATURE:
<221> NAME/KEY: MISC_FEATURE
<222> LOCATION: (82)..(82)
<223> OTHER INFORMATION: Xaa may be Q or E
<220> FEATURE:
<221> NAME/KEY: MISC_FEATURE
<222> LOCATION: (84)..(84)
<223> OTHER INFORMATION: Xaa may be N or S
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (118)..(118)
```

<223> OTHER INFORMATION: Xaa may be L or V

<400> SEQUENCE: 41

```
Gln Ala Gln Leu Xaa Gln Ser Gly Pro Glu Leu Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Pro Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Ala Thr Xaa Thr Ala Asp Lys Ser Xaa Ser Thr Ala Tyr
65                  70                  75                  80

Met Xaa Leu Xaa Ser Leu Xaa Ser Glu Asp Ser Ala Val Tyr Phe Cys
        85                  90                  95

Ala Arg Trp Gly Leu Thr Arg Asp Arg Arg Leu Tyr Leu Asp Tyr Trp
            100                 105                 110

Gly Gln Gly Thr Thr Xaa Thr Val Ser Ser
            115                 120
```

<210> SEQ ID NO 42
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (5)..(5)
<223> OTHER INFORMATION: Xaa can be Q or V
<220> FEATURE:
<221> NAME/KEY: MISC_FEATURE
<222> LOCATION: (11)..(11)
<223> OTHER INFORMATION: Xaa can be L or V
<220> FEATURE:
<221> NAME/KEY: MISC_FEATURE
<222> LOCATION: (12)..(12)
<223> OTHER INFORMATION: Xaa can be V or K
<220> FEATURE:
<221> NAME/KEY: MISC_FEATURE
<222> LOCATION: (19)..(19)
<223> OTHER INFORMATION: Xaa can be E or K
<220> FEATURE:
<221> NAME/KEY: MISC_FEATURE
<222> LOCATION: (20)..(20)
<223> OTHER INFORMATION: Xaa can be I or V
<220> FEATURE:
<221> NAME/KEY: MISC_FEATURE
<222> LOCATION: (43)..(43)
<223> OTHER INFORMATION: Xaa can be K or A
<220> FEATURE:
<221> NAME/KEY: MISC_FEATURE
<222> LOCATION: (67)..(67)
<223> OTHER INFORMATION: Xaa can be K or R
<220> FEATURE:
<221> NAME/KEY: MISC_FEATURE
<222> LOCATION: (70)..(70)
<223> OTHER INFORMATION: Xaa can be L or I
<220> FEATURE:
<221> NAME/KEY: MISC_FEATURE
<222> LOCATION: (76)..(76)
<223> OTHER INFORMATION: Xaa can be S or T
<220> FEATURE:
<221> NAME/KEY: MISC_FEATURE
<222> LOCATION: (82)..(82)
<223> OTHER INFORMATION: Xaa can be Q or E
<220> FEATURE:
<221> NAME/KEY: MISC_FEATURE
<222> LOCATION: (84)..(84)
<223> OTHER INFORMATION: Xaa can be N or S

```
<220> FEATURE:
<221> NAME/KEY: MISC_FEATURE
<222> LOCATION: (87)..(87)
<223> OTHER INFORMATION: Xaa can be T or R
<220> FEATURE:
<221> NAME/KEY: MISC_FEATURE
<222> LOCATION: (91)..(91)
<223> OTHER INFORMATION: Xaa can be S or T
<220> FEATURE:
<221> NAME/KEY: MISC_FEATURE
<222> LOCATION: (118)..(118)
<223> OTHER INFORMATION: Xaa can be L or V

<400> SEQUENCE: 42

Gln Ala Gln Leu Xaa Gln Ser Gly Pro Glu Xaa Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Pro Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Ala Thr Xaa Thr Ala Asp Lys Ser Xaa Ser Thr Ala Tyr
65                  70                  75                  80

Met Xaa Leu Xaa Ser Leu Xaa Ser Glu Asp Xaa Ala Val Tyr Phe Cys
            85                  90                  95

Ala Arg Trp Gly Leu Thr Arg Asp Arg Arg Leu Tyr Leu Asp Tyr Trp
            100                 105                 110

Gly Gln Gly Thr Thr Xaa Thr Val Ser Ser
        115                 120

<210> SEQ ID NO 43
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (5)..(5)
<223> OTHER INFORMATION: Xaa can be Q or V
<220> FEATURE:
<221> NAME/KEY: MISC_FEATURE
<222> LOCATION: (9)..(9)
<223> OTHER INFORMATION: Xaa can be P or A
<220> FEATURE:
<221> NAME/KEY: MISC_FEATURE
<222> LOCATION: (11)..(11)
<223> OTHER INFORMATION: Xaa can be L or V
<220> FEATURE:
<221> NAME/KEY: MISC_FEATURE
<222> LOCATION: (12)..(12)
<223> OTHER INFORMATION: Xaa can be V or K
<220> FEATURE:
<221> NAME/KEY: MISC_FEATURE
<222> LOCATION: (19)..(19)
<223> OTHER INFORMATION: Xaa can be E or K
<220> FEATURE:
<221> NAME/KEY: MISC_FEATURE
<222> LOCATION: (20)..(20)
<223> OTHER INFORMATION: Xaa can be I or V
<220> FEATURE:
<221> NAME/KEY: MISC_FEATURE
<222> LOCATION: (41)..(41)
<223> OTHER INFORMATION: Xaa can be P or R
<220> FEATURE:
<221> NAME/KEY: MISC_FEATURE
<222> LOCATION: (43)..(43)
<223> OTHER INFORMATION: Xaa can be K or A
<220> FEATURE:
```

<220> FEATURE:
<221> NAME/KEY: MISC_FEATURE
<222> LOCATION: (67)..(67)
<223> OTHER INFORMATION: Xaa can be K or R
<220> FEATURE:
<221> NAME/KEY: MISC_FEATURE
<222> LOCATION: (70)..(70)
<223> OTHER INFORMATION: Xaa can be L or I
<220> FEATURE:
<221> NAME/KEY: MISC_FEATURE
<222> LOCATION: (76)..(76)
<223> OTHER INFORMATION: Xaa can be S or T
<220> FEATURE:
<221> NAME/KEY: MISC_FEATURE
<222> LOCATION: (82)..(82)
<223> OTHER INFORMATION: Xaa can be Q or E
<220> FEATURE:
<221> NAME/KEY: MISC_FEATURE
<222> LOCATION: (84)..(84)
<223> OTHER INFORMATION: Xaa can be N or S
<220> FEATURE:
<221> NAME/KEY: MISC_FEATURE
<222> LOCATION: (87)..(87)
<223> OTHER INFORMATION: Xaa can be T or R
<220> FEATURE:
<221> NAME/KEY: MISC_FEATURE
<222> LOCATION: (91)..(91)
<223> OTHER INFORMATION: Xaa can be S or T
<220> FEATURE:
<221> NAME/KEY: MISC_FEATURE
<222> LOCATION: (118)..(118)
<223> OTHER INFORMATION: Xaa can be L or V

<400> SEQUENCE: 43

Gln Ala Gln Leu Xaa Gln Ser Gly Xaa Glu Xaa Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Xaa Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Ala Thr Xaa Thr Ala Asp Lys Ser Xaa Ser Thr Ala Tyr
65                  70                  75                  80

Met Xaa Leu Xaa Ser Leu Xaa Ser Glu Asp Xaa Ala Val Tyr Phe Cys
            85                  90                  95

Ala Arg Trp Gly Leu Thr Arg Asp Arg Arg Leu Tyr Leu Asp Tyr Trp
        100                 105                 110

Gly Gln Gly Thr Thr Xaa Thr Val Ser Ser
    115                 120

<210> SEQ ID NO 44
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (5)..(5)
<223> OTHER INFORMATION: Xaa can be Q or V
<220> FEATURE:
<221> NAME/KEY: MISC_FEATURE
<222> LOCATION: (9)..(9)
<223> OTHER INFORMATION: Xaa can be P or A
<220> FEATURE:
<221> NAME/KEY: MISC_FEATURE
<222> LOCATION: (11)..(11)
<223> OTHER INFORMATION: Xaa can be L or V
<220> FEATURE:
<221> NAME/KEY: MISC_FEATURE

```
<222> LOCATION: (12)..(12)
<223> OTHER INFORMATION: Xaa can be V or K
<220> FEATURE:
<221> NAME/KEY: MISC_FEATURE
<222> LOCATION: (19)..(19)
<223> OTHER INFORMATION: Xaa can be E or K
<220> FEATURE:
<221> NAME/KEY: MISC_FEATURE
<222> LOCATION: (20)..(20)
<223> OTHER INFORMATION: Xaa can be I or V
<220> FEATURE:
<221> NAME/KEY: MISC_FEATURE
<222> LOCATION: (41)..(41)
<223> OTHER INFORMATION: Xaa can be P or R
<220> FEATURE:
<221> NAME/KEY: MISC_FEATURE
<222> LOCATION: (43)..(43)
<223> OTHER INFORMATION: Xaa can be K or A
<220> FEATURE:
<221> NAME/KEY: MISC_FEATURE
<222> LOCATION: (67)..(67)
<223> OTHER INFORMATION: Xaa can be K or R
<220> FEATURE:
<221> NAME/KEY: MISC_FEATURE
<222> LOCATION: (68)..(68)
<223> OTHER INFORMATION: Xaa can be A to V
<220> FEATURE:
<221> NAME/KEY: MISC_FEATURE
<222> LOCATION: (70)..(70)
<223> OTHER INFORMATION: Xaa can be L or I
<220> FEATURE:
<221> NAME/KEY: MISC_FEATURE
<222> LOCATION: (76)..(76)
<223> OTHER INFORMATION: Xaa can be S or T
<220> FEATURE:
<221> NAME/KEY: MISC_FEATURE
<222> LOCATION: (82)..(82)
<223> OTHER INFORMATION: Xaa can be Q or E
<220> FEATURE:
<221> NAME/KEY: MISC_FEATURE
<222> LOCATION: (84)..(84)
<223> OTHER INFORMATION: Xaa can be N or S
<220> FEATURE:
<221> NAME/KEY: MISC_FEATURE
<222> LOCATION: (87)..(87)
<223> OTHER INFORMATION: Xaa can be T or R
<220> FEATURE:
<221> NAME/KEY: MISC_FEATURE
<222> LOCATION: (91)..(91)
<223> OTHER INFORMATION: Xaa can be S or T
<220> FEATURE:
<221> NAME/KEY: MISC_FEATURE
<222> LOCATION: (118)..(118)
<223> OTHER INFORMATION: Xaa can be L or V

<400> SEQUENCE: 44

Gln Ala Gln Leu Xaa Gln Ser Gly Xaa Glu Xaa Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Xaa Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Xaa Thr Xaa Thr Ala Asp Lys Ser Xaa Ser Thr Ala Tyr
65                  70                  75                  80

Met Xaa Leu Xaa Ser Leu Xaa Ser Glu Asp Xaa Ala Val Tyr Phe Cys
                85                  90                  95

Ala Arg Trp Gly Leu Thr Arg Asp Arg Arg Leu Tyr Leu Asp Tyr Trp
            100                 105                 110

Gly Gln Gly Thr Thr Xaa Thr Val Ser Ser
```

115                 120

<210> SEQ ID NO 45
<211> LENGTH: 122
<212> TYPE: PRT
<213> ORGANISM: Artificial
<220> FEATURE:
<223> OTHER INFORMATION: Heavy chain variable region sequence
<220> FEATURE:
<221> NAME/KEY: MISC_FEATURE
<222> LOCATION: (5)..(5)
<223> OTHER INFORMATION: Xaa can be Q or V
<220> FEATURE:
<221> NAME/KEY: MISC_FEATURE
<222> LOCATION: (9)..(9)
<223> OTHER INFORMATION: Xaa can be P or A
<220> FEATURE:
<221> NAME/KEY: MISC_FEATURE
<222> LOCATION: (11)..(11)
<223> OTHER INFORMATION: Xaa can be L or V
<220> FEATURE:
<221> NAME/KEY: MISC_FEATURE
<222> LOCATION: (12)..(12)
<223> OTHER INFORMATION: Xaa can be V or K
<220> FEATURE:
<221> NAME/KEY: MISC_FEATURE
<222> LOCATION: (19)..(19)
<223> OTHER INFORMATION: Xaa can be E or K
<220> FEATURE:
<221> NAME/KEY: MISC_FEATURE
<222> LOCATION: (20)..(20)
<223> OTHER INFORMATION: Xaa can be I or V
<220> FEATURE:
<221> NAME/KEY: MISC_FEATURE
<222> LOCATION: (41)..(41)
<223> OTHER INFORMATION: Xaa can be P or R
<220> FEATURE:
<221> NAME/KEY: MISC_FEATURE
<222> LOCATION: (43)..(43)
<223> OTHER INFORMATION: Xaa can be K or A
<220> FEATURE:
<221> NAME/KEY: MISC_FEATURE
<222> LOCATION: (67)..(67)
<223> OTHER INFORMATION: Xaa can be K or R
<220> FEATURE:
<221> NAME/KEY: MISC_FEATURE
<222> LOCATION: (68)..(68)
<223> OTHER INFORMATION: Xaa can be A to V
<220> FEATURE:
<221> NAME/KEY: MISC_FEATURE
<222> LOCATION: (70)..(70)
<223> OTHER INFORMATION: Xaa can be L or I
<220> FEATURE:
<221> NAME/KEY: MISC_FEATURE
<222> LOCATION: (76)..(76)
<223> OTHER INFORMATION: Xaa can be S or T
<220> FEATURE:
<221> NAME/KEY: MISC_FEATURE
<222> LOCATION: (82)..(82)
<223> OTHER INFORMATION: Xaa can be Q or E
<220> FEATURE:
<221> NAME/KEY: MISC_FEATURE
<222> LOCATION: (84)..(84)
<223> OTHER INFORMATION: Xaa can be N or S
<220> FEATURE:
<221> NAME/KEY: MISC_FEATURE
<222> LOCATION: (87)..(87)
<223> OTHER INFORMATION: Xaa can be T or R
<220> FEATURE:
<221> NAME/KEY: MISC_FEATURE
<222> LOCATION: (91)..(91)
<223> OTHER INFORMATION: Xaa can be S or T
<220> FEATURE:
<221> NAME/KEY: MISC_FEATURE
<222> LOCATION: (95)..(95)
<223> OTHER INFORMATION: Xaa can be F or Y
<220> FEATURE:
<221> NAME/KEY: MISC_FEATURE

```
<222> LOCATION: (118)..(118)
<223> OTHER INFORMATION: Xaa can be L or V

<400> SEQUENCE: 45

Gln Ala Gln Leu Xaa Gln Ser Gly Xaa Glu Xaa Xaa Lys Pro Gly Ala
1               5                   10                  15

Ser Val Xaa Xaa Ser Cys Lys Ala Ser Gly Tyr Leu Phe Ser Asn Ser
            20                  25                  30

Trp Met Asn Trp Val Lys Gln Arg Xaa Gly Xaa Gly Leu Glu Trp Ile
        35                  40                  45

Gly Arg Ile Phe Pro Gly Asp Gly Asp Thr Asn Tyr Asn Gly Lys Phe
    50                  55                  60

Lys Gly Xaa Xaa Thr Xaa Thr Ala Asp Lys Ser Xaa Ser Thr Ala Tyr
65                  70                  75                  80

Met Xaa Leu Xaa Ser Leu Xaa Ser Glu Asp Xaa Ala Val Tyr Xaa Cys
            85                  90                  95

Ala Arg Trp Gly Leu Thr Arg Asp Arg Arg Leu Tyr Leu Asp Tyr Trp
            100                 105                 110

Gly Gln Gly Thr Thr Xaa Thr Val Ser Ser
            115                 120

<210> SEQ ID NO 46
<211> LENGTH: 723
<212> TYPE: DNA
<213> ORGANISM: Artificial
<220> FEATURE:
<223> OTHER INFORMATION: Complete light chain coding sequence

<400> SEQUENCE: 46
atggagacac attctcaggt ctttgtatac atgttgctgt ggttgtctgg tgtcgaggga    60
gacatcgtga tgacccagag ccccgacagc ctggccgtca gctgggcga gcgcgccacc   120
atcaactgca agagcagcca gagcctgctg tacagcagca accagaagaa ctacctggcc   180
tggtaccagc agaagcccgg ccaggccccc cgcctgctga tctactgggc cagcacccgc   240
gagagcggcg tgcccgaccg cttcaccggc agcggcagcg gcaccgactt caccctgacc   300
atcagcagcc tgcaggccga ggacgtggcc gtgtactact gcaagcagta ctacacctac   360
cccctgacct tcggccaggg caccaagctg gagatcaagc gtacggtggc tgcaccatct   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga aacacaaagt ctacgcctgc   660
gaagtcaccc atcagggcct gagctcgccc gtcacaaaga gcttcaacag gggagagtgt   720
tag                                                                 723

<210> SEQ ID NO 47
<211> LENGTH: 240
<212> TYPE: PRT
<213> ORGANISM: Artificial
<220> FEATURE:
<223> OTHER INFORMATION: Complete light chain sequence

<400> SEQUENCE: 47

Met Glu Thr His Ser Gln Val Phe Val Tyr Met Leu Leu Trp Leu Ser
1               5                   10                  15

Gly Val Glu Gly Asp Ile Val Met Thr Gln Ser Pro Asp Ser Leu Ala
```

```
                20                  25                  30
Val Ser Leu Gly Glu Arg Ala Thr Ile Asn Cys Lys Ser Gln Ser
             35                  40                  45

Leu Leu Tyr Ser Ser Asn Gln Lys Asn Tyr Leu Ala Trp Tyr Gln Gln
 50                  55                  60

Lys Pro Gly Gln Ala Pro Arg Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Leu Gln Ala Glu Asp Val Ala Val Tyr
            100                 105                 110

Tyr Cys Lys Gln Tyr Tyr Thr Tyr Pro Leu Thr Phe Gly Gln Gly Thr
            115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240
```

<210> SEQ ID NO 48
<211> LENGTH: 1416
<212> TYPE: DNA
<213> ORGANISM: Artificial
<220> FEATURE:
<223> OTHER INFORMATION: Complete heavy chain coding sequence

<400> SEQUENCE: 48

```
atggcttggg tgtggacctt gctattcctg atggcagctg cccaaagtat acaggcccag      60
gtgcagctgg tgcagagcgg cgccgaggtg aagaagcccg cgccagcgt gaaggtcagc      120
tgcaaggcca gcggctacct gttcagcaac agctggatga actgggtgaa gcagcgccgc     180
ggcgccggcc tggagtggat cggccgcatc ttccccggcg acggcgacac caactacaac     240
ggcaagttca agggccgcgt gaccatcacc gccgacaaga gcaccagcac cgcctacatg     300
gagctgagca gcctgcgcag cgaggacacc gccgtgtact actgcgcccg ctggggcctg     360
acccgcgacc gccgcctgta cctggactac tggggccagg gcaccaccgt gaccgtcagc     420
agcgcctcca ccaagggccc atcggtcttc cccctggcac cctcctccaa gagcacctct     480
gggggcacag cggccctggg ctgcctggtc aaggactact cccccgaacc ggtgacggtg     540
tcgtggaact caggcgccct gaccagcggc gtgcacacct tcccggctgt cctacagtcc     600
tcaggactct actccctcag cagcgtggtg accgtgccct ccagcagctt gggcacccag     660
acctacatct gcaacgtgaa tcacaagccc agcaacacca aggtggacaa gaaagttgag     720
cccaaatctt gtgacaaaac tcacacatgc ccaccgtgcc cagcacctga actcctgggg    780
ggaccgtcag tcttcctctt ccccccaaaa cccaaggaca cctcatgat ctcccggacc     840
```

```
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc   1020
aaggagtaca agtgcaaggt ctccaacaaa gccctcccag ccccatcga gaaaaccatc    1080 tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tacagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaatga                              1416
```

<210> SEQ ID NO 49
<211> LENGTH: 471
<212> TYPE: PRT
<213> ORGANISM: Artificial
<220> FEATURE:
<223> OTHER INFORMATION: Complete heavy chain sequence

<400> SEQUENCE: 49

```
Met Ala Trp Val Trp Thr Leu Leu Phe Leu Met Ala Ala Ala Gln Ser
1               5                   10                  15

Ile Gln Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Leu Phe
        35                  40                  45

Ser Asn Ser Trp Met Asn Trp Val Lys Gln Arg Arg Gly Ala Gly Leu
    50                  55                  60

Glu Trp Ile Gly Arg Ile Phe Pro Gly Asp Gly Asp Thr Asn Tyr Asn
65                  70                  75                  80

Gly Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Leu Thr Arg Asp Arg Leu Tyr Leu
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
```

-continued

```
                260                 265                 270
Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
    450                 455                 460

Leu Ser Leu Ser Pro Gly Lys
465                 470
```